United States Patent
Schiltz et al.

(10) Patent No.: US 9,688,637 B2
(45) Date of Patent: Jun. 27, 2017

(54) 3-AMIDOBENZAMIDES AND USES THEREOF FOR INCREASING CELLULAR LEVELS OF A3G AND OTHER A3 FAMILY MEMBERS

(71) Applicant: Northwestern University, Evanston, IL (US)

(72) Inventors: Gary E. Schiltz, Naperville, IL (US); Chisu Song, Naperville, IL (US); Richard T. D'Aquila, Chicago, IL (US); Meejeon Roh, Naperville, IL (US)

(73) Assignee: Northwestern Universtiy, Evanston, IL (US)

( * ) Notice: Subject to any disclaimer, the term of this patent is extended or adjusted under 35 U.S.C. 154(b) by 0 days.

(21) Appl. No.: 14/832,508

(22) Filed: Aug. 21, 2015

(65) Prior Publication Data
US 2016/0052870 A1 Feb. 25, 2016

Related U.S. Application Data

(60) Provisional application No. 62/040,237, filed on Aug. 21, 2014.

(51) Int. Cl.
| | | |
|---|---|---|
| *C07D 217/06* | (2006.01) | |
| *C07D 317/66* | (2006.01) | |
| *C07D 309/08* | (2006.01) | |
| *C07D 307/24* | (2006.01) | |
| *C07C 271/28* | (2006.01) | |
| *C07C 311/08* | (2006.01) | |
| *C07C 275/42* | (2006.01) | |
| *C07D 317/68* | (2006.01) | |
| *C07D 213/81* | (2006.01) | |
| *C07D 213/82* | (2006.01) | |
| *C07D 295/16* | (2006.01) | |
| *C07C 311/14* | (2006.01) | |
| *C07D 213/75* | (2006.01) | |
| *C07C 271/16* | (2006.01) | |
| *C07C 237/44* | (2006.01) | |
| *C07D 495/04* | (2006.01) | |

(52) U.S. Cl.
CPC .......... *C07D 217/06* (2013.01); *C07C 237/44* (2013.01); *C07C 271/16* (2013.01); *C07C 271/28* (2013.01); *C07C 275/42* (2013.01); *C07C 311/08* (2013.01); *C07C 311/14* (2013.01); *C07D 213/75* (2013.01); *C07D 213/81* (2013.01); *C07D 213/82* (2013.01); *C07D 295/16* (2013.01); *C07D 307/24* (2013.01); *C07D 309/08* (2013.01); *C07D 317/66* (2013.01); *C07D 317/68* (2013.01); *C07D 495/04* (2013.01); *C07C 2101/02* (2013.01); *C07C 2101/04* (2013.01); *C07C 2101/08* (2013.01); *C07C 2101/14* (2013.01); *C07C 2103/74* (2013.01)

(58) Field of Classification Search
None
See application file for complete search history.

(56) References Cited

FOREIGN PATENT DOCUMENTS

| CN | 102206172 | 5/2011 |
|---|---|---|
| WO | 9932433 | 7/1999 |
| WO | 0055120 | 9/2000 |
| WO | 2008002576 | 1/2008 |

OTHER PUBLICATIONS

Abrahams, M.R. et al., Rapid, complex adaptation of transmitted HIV-1 full-length genomes in subtype C-infected individuals with differing disease progression. AIDS, 2013; 27(4): 507-18.
Argyris EG, Acheampong E, et al. The interferon-induced expression of APOBEC3G in human blood-brain barrier exerts a potent intrinsic immunity to block HIV-1 entry to central nervous system. Virology. 2007; 367(2): 440-51.
Bello D, Webber MM, Kleinman HK, Wartinger DD, Rhim JS. Androgen responsive adult human prostatic epithelial cell lines immortalized by human papillomavirus 18. Carcinogenesis. Jun. 1997;18(6):1215-23.
Bonvin M, Achermann F, et al. Interferon-inducible expression of APOBEC3 editing enzymes in human hepatocytes and inhibition of hepatitis B virus replication. Hepatology. 2006; 43(6): 1364-74.
Burns MB, Leonard B, Harris RS. APOBEC3B: pathological consequences of an innate immune DNA mutator. Biomed J. Mar.-Apr. 2015;38(2):102-10. doi: 10.4103/2319-4170.148904.
Chen K, Huang J, et al. Alpha interferon potently enhances the anti-human immunodeficiency virus type 1 activity of APOBEC3G in resting primary CD4 T cells. J Virol. 2006; 80(15): 7645-57.
Chen H, Wang LW, et al. Interferon-alpha Induces High Expression of APOBEC3G and STAT-1 in Vitro and in Vivo. Int J Mol Sci. 2010; 11(9): 3501-12.
Contreras-Galindo, R., Kaplan, M.H., et al. Characterization of human endogenous retroviral elements in the blood of HIV-1-infected individuals. J Virol 2012; 86: 262-276.
Crow YJ, Rehwinkel J. Aicardi-Goutieres syndrome and related phenotypes: linking nucleic acid metabolism with autoimmunity. Hum Mol Genet. 2009; 18(R2): R130-6.
De Pasquale, M., Kourteva, Y., et al. Lower HIV provirus levels are associated with more APOBEC3G protein in blood resting memory CD4+ T lymphocytes of controllers in vivo. PLOS ONE 2013; 8(10): e76002. doi:10.1371/journal.pone.0076002.
Doitsh G, Cavrois M, et al. Abortive HIV infection mediates CD4 T cell depletion and inflammation in human lymphoid tissue. Cell. 2010; 143(5): 789-801.

(Continued)

*Primary Examiner* — Zinna Northington Davis
(74) *Attorney, Agent, or Firm* — Andrus Intellectual Property Law, LLP

(57) ABSTRACT

Disclosed are novel benzamide compounds and the uses thereof for treating diseases and disorders in a patient in need thereof by increasing cellular levels of A3G and/or other members of the A3 family of proteins in the patient. The disclosed compounds include 3-benzamide compounds that may be administered treat an HIV-1 infection or cancer in a patient.

13 Claims, 12 Drawing Sheets

(56) References Cited

OTHER PUBLICATIONS

Fox EJ, Loeb LA. Lethal mutagenesis: targeting the mutator phenotype in cancer. Semin Cancer Biol. Oct. 2010;20(5):353-9. doi: 10.1016/j.semcancer.2010.10.005.

Gonzalez-Hemandez MJ, Swanson MD, et al. Expression of human endogenous retrovirus type K (HML-2) is activated by the Tat protein of HIV-1. J Virol. 2012; 86(15): 7790-805.

Jiang, J. D.; Davis, A. S.; Middleton, K; Ling, Y. H.; Perez-Soler, R.; Holland, J. F.; Bekesi, J. G., 3-(iodoacetamido)-benzoylurea: A novel cancericidal tubulin ligand that inhibits microtubule polymerization, phosphorylates bcl-2, and induces apoptosis in tumor cells. Cancer Research 1998, 58 (23), 5389-5395.

Jiang M, Strand DW, Fernandez S, He Y, Yi Y, Birbach A, Qiu Q, Schmid J, Tang DG, Hayward SW. Functional remodeling of benign human prostatic tissues in vivo by spontaneously immortalized progenitor and intermediate cells. Stem Cells. Feb. 2010;28(2):344-56. doi: 10.1002/stem.284.

Jin X, Brooks A, Chen H, et al. APOBEC3G/CEMI5 (hA3G) mRNA levels associate inversely with human Immunodeficiency virus viremia. J Virol. 2005; 79(17): 11513-6.

Jin X, Wu H, Smith H. APOBEC3G levels predict rates of progression to AIDS. Retrovirology. 2007; 4: 20.

Jones, R.B., Garrison, K.E., et al. HERV-K-specific T cells eliminate diverse HIV-1/2 and SIV primary isolates. J Clin Invest 2012; 122: 4473-4489.

Jones, R.B., Song, H., et al. LINE-1 Retrotransposable Element DNA Accumulates in HIV-1-infected Cells. J Virol 2013; 87(24): 13307-20.

Kieffer TL, Kwon P, et al. G→A hypermutation in protease and reverse transcriptase regions of human Immunodeficiency virus type 1 residing in resting CD4+ T cells in vivo. J Virol. 2005; 79(3): 1975-80.

Korteva, Y., De Pasquale, et al. APOBEC3G expression and hypermutation are inversely associated with human immunodeficiency virus type 1 (HIV-1) burden in vivo. Virology 2012; 430: 1-9.

Krupp A, McCarthy KR, et al. APOBEC3G polymorphism as a selective barrier to cross-species transmission and emergence of pathogenic SIV and AIDS in a primate host. PLoS Pathog. 2013; 9(10): e1003641.

Land, A.M., Ball, T.B., et al. Human immunodeficiency virus (HIV) type 1 proviral hypermutation correlates with CD4 count in HIV-infected women from Kenya. J Virol 2008; 82: 8172-8182.

Mohanram V, Sköld AE, et al. IFN-α induces APOBEC3G, F, and A in immature dendritic cells and limits HIV-1 spread to CD4+ T cells. J Immunol. 2013 ; 190(7): 3346-53.

Mussil B, Sauermann U, et al. Increased APOBEC3G and APOBEC3F expression is associated with low viral load and prolonged survival in simian immunodeficiency virus infected rhesus monkeys. Retrovirology. 2011; 8: 77.

Nathans R, Cao H, et al. Small-molecule inhibition of HIV-1 Vif. Nat Biotechnol. Oct. 2008; 26(10): 1187-92.

Ormsby, C.E., Sengupta, D., et al. Human endogenous retrovirus expression is inversely associated with chronic immune activation in HIV-1 infection. PLoS One 2012; 7: e41021.

Peng G, Lei KJ, et al. Induction of APOBEC3 family proteins, a defensive maneuver underlying interferon-induced anti-HIV-1 activity. J Exp Med. 2006; 203(1): 41-6.

Sawyer SL, Emerman M, Malik HS. Ancient adaptive evolution of the primate antiviral DNA-editing enzyme APOBEC3G. PLoS Biol. 2004; 2(9): E275.

Simon V, Zennou V, et al. Natural variation in Vif: differential impact on APOBEC3G/3F and a potential role in HIV-1 diversification. PLoS Pathog. 2005; 1(1): e6.

Trapp S, Derby NR, et al. Double-stranded RNA analog poly(I:C) inhibits human immunodeficiency virus amplification in dendritic cells via type I interferon-mediated activation of APOBEC3G. J Virol. 2009; 83(2): 884-95.

Vetter ML, Johnson ME, et al. Differences in APOBEC3G expression in CD4+ T helper lymphocyte subtypes modulate HIV-1 infectivity. PLoS Pathog. 2009; 5(2): e1000292.

Vetter, M.L., and D'Aquila, R.T. Cytoplasmic APOBEC3G restricts incoming Vifpositive human immunodeficiency virus type 1 and increases two-long terminal repeat circle formation in activated T-helper-subtype cells. J Virol 2009; 83: 8646-8654.

Wang FX, Huang J, et al. APOBEC3G upregulation by alpha interferon restricts human immunodeficiency virus type 1 infection in human peripheral plasmacytoid dendritic cells. J Gen Virol. 2008; 89(Pt 3): 722-30.

Wang YJ, Wang X, et al. Expression and regulation of antiviral protein APOBEC3G in human neuronal cells. J Neuroimmunol. 2009; 206(1-2): 14-21.

Wood, N., et al., HIV evolution in early infection: selection pressures, patterns of insertion and deletion, and the impact of APOBEC. PLoS Pathog, 2009. 5(5): e1000414.

The TP53 Web Site, http://p53.free.fr/Database/Cancer_cell_lines/p53_cell_lines.html, Nov. 30, 2015.

International Search Report for International Application No. PCT/US2015/046328 dated Dec. 17, 2015.

Written Opinion of the International Searching Authority for International Application No. PCT/US 2015-046328 dated Dec. 17, 2015.

International Preliminary Report on Patentability for International Application No. PCT/US2015/046328 dated Mar. 2, 2017.

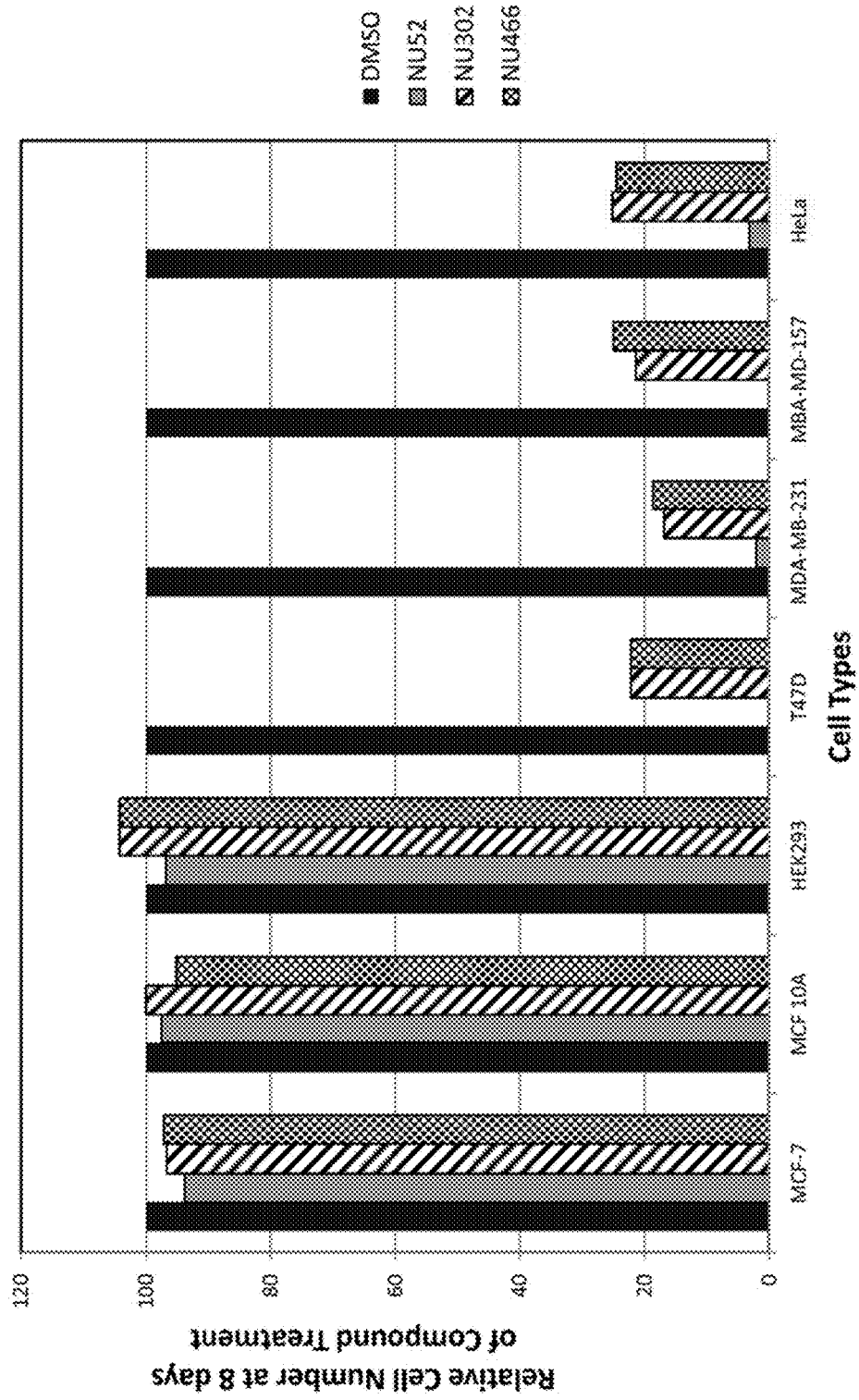

3-AMIDOBENZAMIDES AND USES THEREOF FOR INCREASING CELLULAR LEVELS OF A3G AND OTHER A3 FAMILY MEMBERS

CROSS-REFERENCE TO RELATED PATENT APPLICATIONS

The present application claims the benefit of priority to U.S. Provisional Patent Application No. 62/040,237, filed on Aug. 21, 2015, the content of which is incorporated herein by reference in its entirety.

BACKGROUND

The field of the invention relates to benzamide compounds and therapeutic uses thereof. In particular, the field of the invention relates to novel 3-amido benzamide compounds and therapeutic uses thereof for increasing levels of APOBEC3G (A3G) and related cellular cytidine deaminases in human cells. More specifically, the disclosed 3-amido compounds could serve as therapies for diseases including but not limited to HIV infection and cancer.

Human APOBEC3G (A3G), otherwise referred to as "apolipoprotein B mRNA-editing enzyme, catalytic polypeptide-like 3G" is an enzyme that induces hypermutation of guanosine (G) to adenine (A) in single-stranded DNA. A3G and other A3 family members (including A3F and A3H) have been shown to be inhibitors against human immunodeficiency virus type 1 (HIV-1) infection. These A3 proteins block HIV reverse transcription (RT) and integration, by causing signature "G-to-A hypermutations" in minus-strand DNA that is an intermediate in the process of RT and also by mechanisms independent of cytidine deaminase enzymatic activity. HIV virion infectivity factor (Vif) must degrade A3 proteins in HIV-infected T cells in order to produce infectious virus from those cells. However, there is natural variation in the A3-degrading function of Vif (1), and partial A3G restriction of Vif-positive HIV has been documented in vitro (2). Higher levels of APOBEC3s in the physiological range inhibit Vif-positive HIV-1 replication in cultured cells in vitro (2, 3); however, A3s only completely block replication of Vif-defective HIV-1 in vitro. In vivo, levels of HIV provirus and A3G are inversely associated (4, 5), and lower viremia and higher CD4 count are also associated with more cellular A3G in blood cells (4, 6, 7 and others). A measure of the extent of A3 cytidine deamination of HIV genomes in vivo (PBMC provirus hypermutation index) above a certain level is associated with decreased plasma HIV-1 RNA levels (4). Activity of A3G against other viruses including hepatitis B virus (HBV) has also been described. However, A3G, F, and H have not been implicated in hypermutating cellular chromosomal DNA.

A3B is not expressed at detectable levels in primary human T lymphocytes (which are the major host cells for HIV in which A3G, F, and H act), many other primary human cells and many cell lines. However, increased A3B expression has been noted in many types of cancer cells (in both cell lines in vitro and in tumor biopsy specimens). Increased A3B has been associated with increasing mutational load in genomes of these cancers. A3B over expression and enhanced cytidine deamination of human nuclear (chromosomal) DNA has been implicated in pathogenesis of several types of cancer, including cancers of breast, lung, head/neck, cervical, ovarian, bladder, prostate and multiple myeloma and certain lymphomas occurring in HIV patients (primary effusion lymphoma). A3B increases genomic mutations specifically in these cancer cells and has been called "mutagenic fuel for cancer evolution and heterogeneity" (8). While attention has been chiefly directed to inhibiting A3B cytidine deaminase activity as a therapeutic strategy, it has also been suggested that further increasing excess A3B-mediated genomic hypermutation may cause cancer cell death by synthetic lethality without harming normal cells (by analogy to effects of "mutation catastrophe" on viruses) (9, 10). It is well described that one of the essential activities of a functional p53 protein, "the guardian of the genome", is to allow repair of potentially lethal DNA damage. Thus, we hypothesize that cancer cells lacking functional p53 will be more prone to synthetic lethality from excess A3B-mediated genome hypermutation.

There is a need for better and different treatments for HIV and cancer patients. Herein we disclose small molecules able to boost expression of A3G and related cellular proteins. These compounds could serve as therapies for the diseases in which A3G (and A3F and A3H) are a protective/defensive factor including but not limited to HIV, and could be a treatment for some cancers.

SUMMARY

Disclosed are novel benzamide compounds and the uses thereof for treating diseases and disorders in a patient in need thereof by increasing cellular levels of A3G and/or other members of the A3 family of proteins in the patient. The disclosed compounds include 3-benzamide compounds that may be administered to treat an HIV-1 infection or cancer in a patient.

The disclosed compounds may be referred to as 3-benzamide compounds having a core structure as follows:

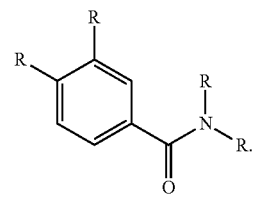

In particular, the disclosed compounds have a formula I as follows:

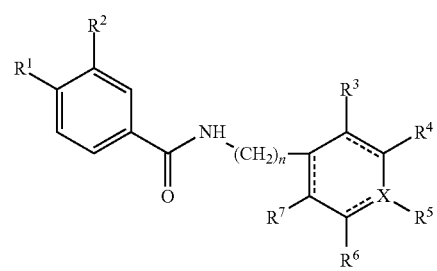

wherein:

n is 0 or 1;

X is C or N;

$R^1$ is hydroxyl, C1-C6-alkoxy, or

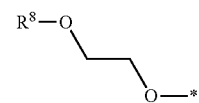

wherein
R⁸ is C1-C6-alkyl,

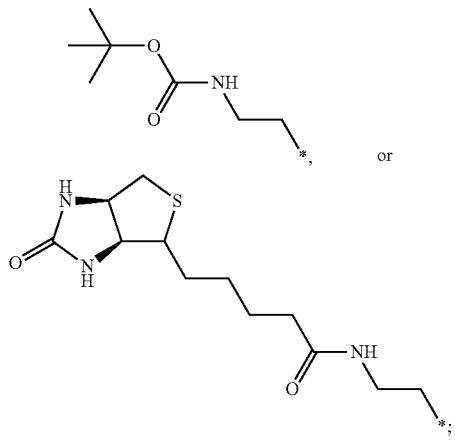

R² is H, nitro, amino, or

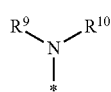

wherein
R⁹ is H, or C1-C6-alkyl;
R¹⁰ is C1-C6-alkyl, methyl sulfonyl, methylethyl sulfonyl, cyclopropyl sulfonyl, cyclobutyl sulfonyl, or

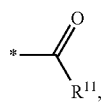

wherein
R¹¹ is H, C1-C6-alkyl optionally substituted with C1-C6-alkoxy, hydroxyl, C1-C6-alkylamino, C1-C6-dialkylamino, phenyl, benzyl, benzo[1,3]dioxyl, pyridin-2-yl, pyridin-3-yl, pyridin-4-yl, C3-C6-cycloalkyl optionally substituted with methyl, C1-C6-alkoxy, N-piperidinyl, tetrahydrofuran-2-yl, adamantanyl, or

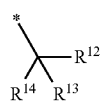

wherein
R¹² and R¹³ are independently selected from H, C1-C6-alkyl, C1-C6-alkyl optionally substituted with C1-C6-alkoxy, C1-C6 cycloalkyl, phenyl, C1-C6-alkylamino, C1-C6-dialkyl amino, or R¹² and R¹³ together form a C3-C6 homocycle or a C3-C6 heterocycle, which optionally is unsaturated at one or more bonds;
R¹⁴ is H or C1-C6-alkyl; and
R³, R⁴, R⁵, R⁶, and R⁷ are independently selected from H, C1-C6-alkoxy, halo, phenyl, or R⁴ and R⁵ together form a C5-C7 homocycle or C5-C7 heterocycle, which optionally is unsaturated at one or more bonds.

The disclosed compounds may have the specific formula Ia or Ib:

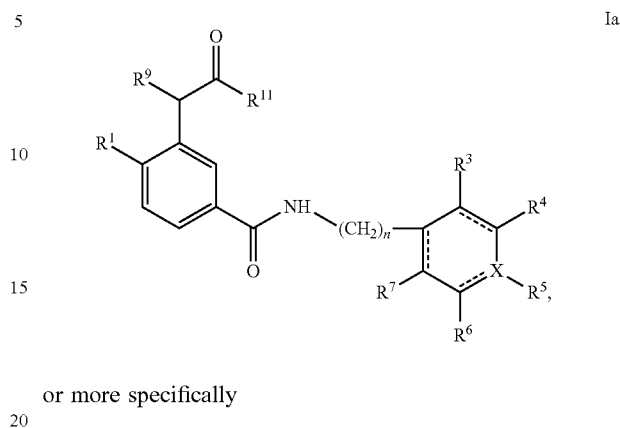

or more specifically

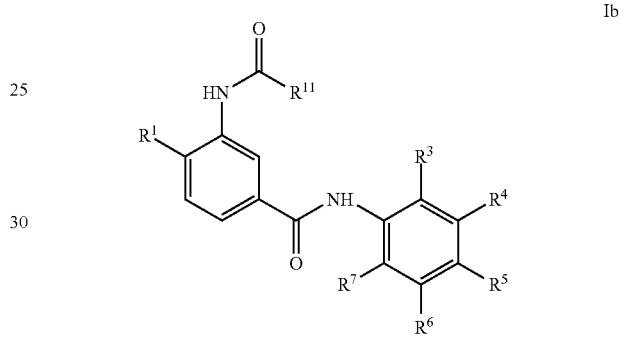

wherein:
R¹ is C1-C6-alkoxy;
R⁹ is H, or C1-C6-alkyl;
R¹¹ is H, C1-C6-alkyl, hydroxyl, C1-C6-alkylamino, C1-C6 dialkylamino, phenyl, benzyl, benzo[1,3]dioxyl, pyridin-2-yl, pyridin-3-yl, pyridin-4-yl, C3-C6-cycloalkyl optionally substituted with methyl, C1-C6-alkoxy, C1-C6-alkyl optionally substituted with C1-C6-alkoxy, N-piperidinyl, and tetrahydrofuran-2-yl; and
R³, R⁴, R⁵, R⁶, and R⁷ are independently selected from H, C1-C6-alkoxy, and halo.

Also disclosed are pharmaceutical compositions comprising the disclosed compounds or pharmaceutically acceptable salts thereof and a pharmaceutical carrier. The disclosed pharmaceutical compositions may comprise an effective amount of the disclosed compounds for increasing levels of A3G and/or other members of the A3 family of proteins after the composition is administering to a patient in need thereof. As such, therapeutic methods also are contemplated herein and suitable patients for the treatment methods may include, but are not limited to patients having an HIV-1 infection and/or cancer.

at different levels (each from a CMV promoter). (B) Two of the cell clones from (A) are shown, as well as 4 other cell clones that stably express A3G from a simple retrovirus promoter (FM1). This includes 2 of the cell clones with FM1 promoter driven A3G-Luc that were engineered to also co-express HIV-1 Vif from the same promoter. Co-expression of Vif and A3G-Luc decreases A3G-Luc expression, indicating that the A3G-Luc fusion protein remains susceptible to Vif-mediated degradation.

Figure 2A:
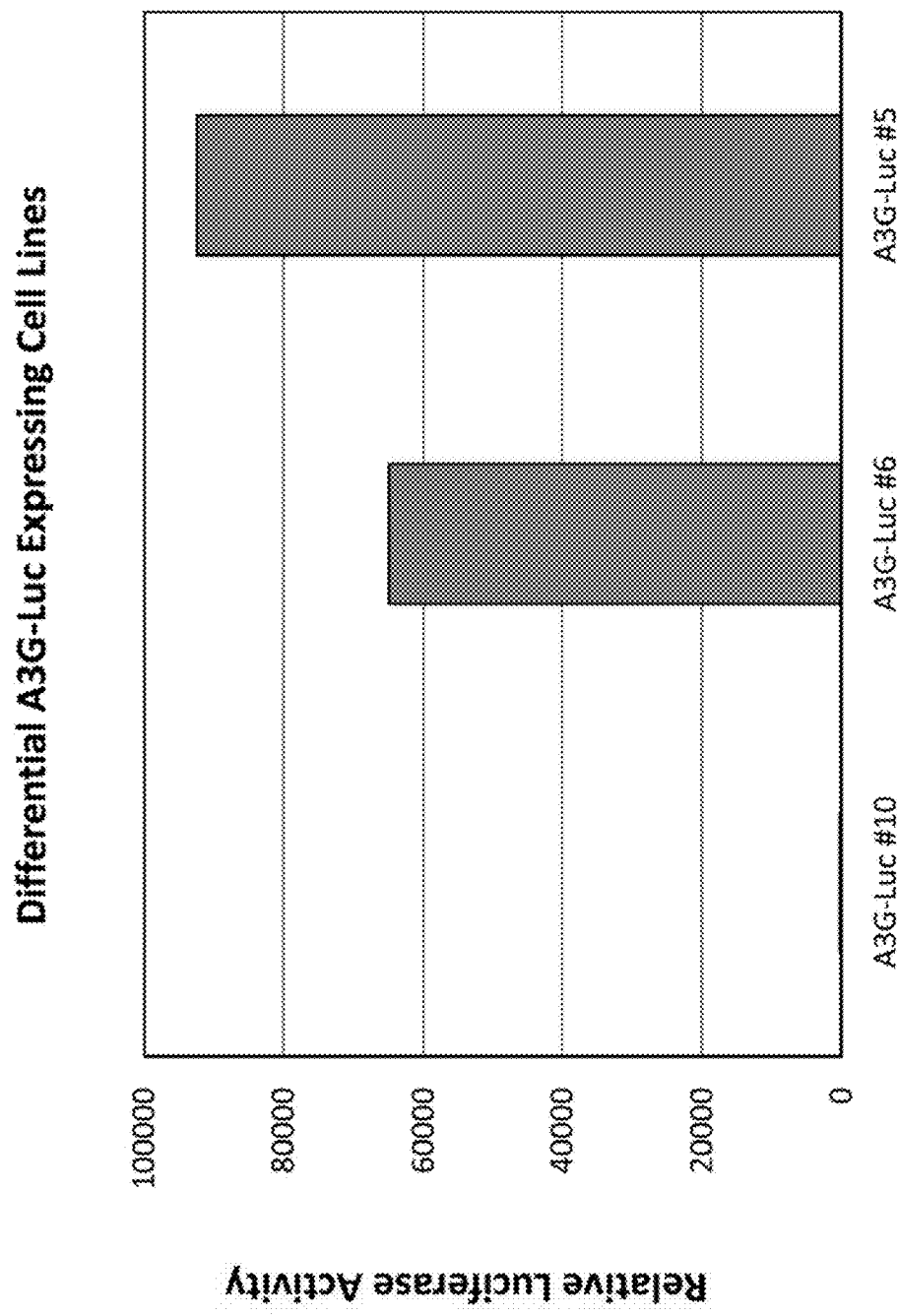
FIG. 2A and FIG. 2B. (A) Three different 293T cell clones stably expressing A3G-luciferase fusion proteins (A3G-Luc)
Figure 3:
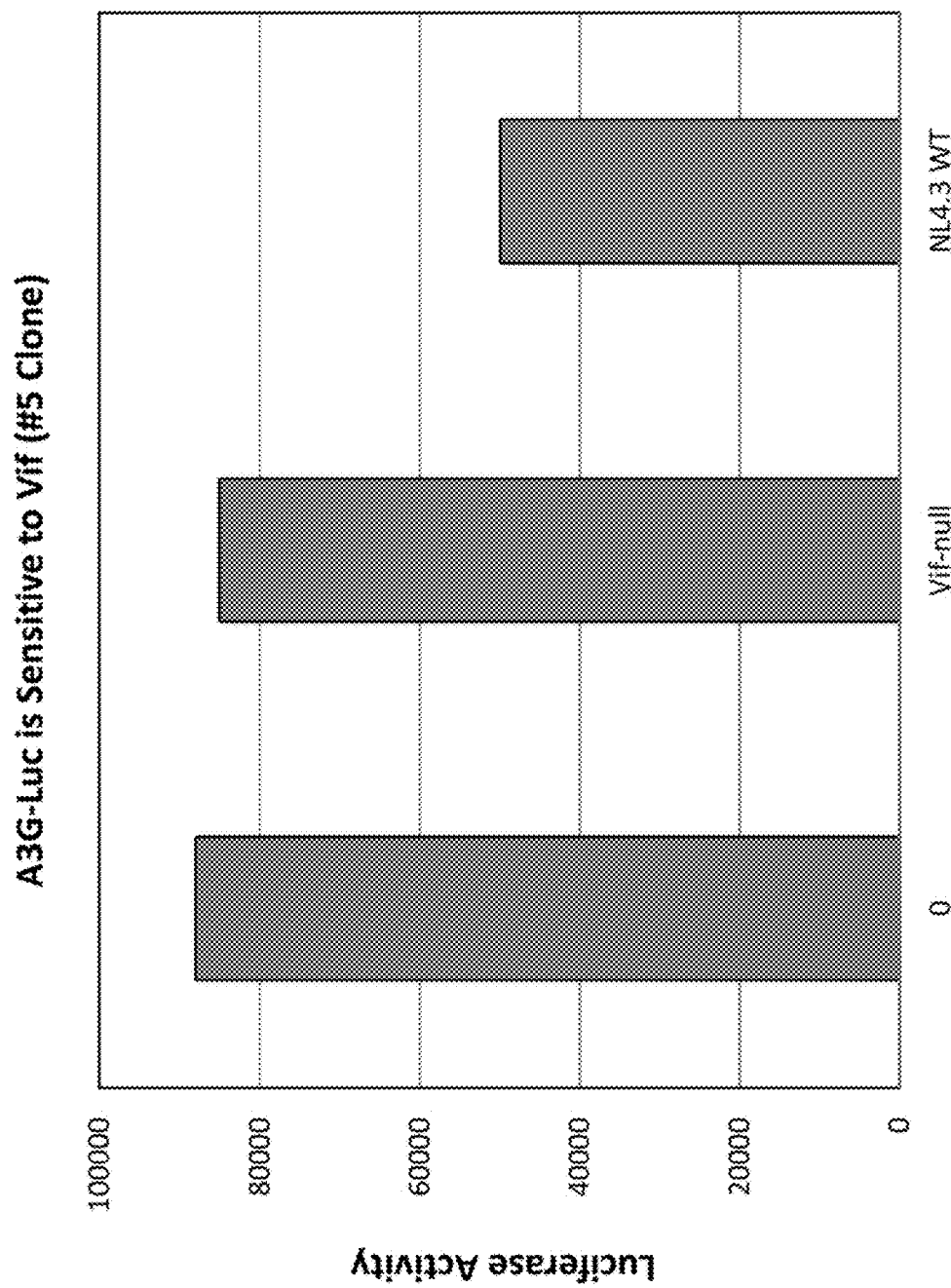

FIG. 3. A3G-Luc fusion proteins are sensitive to Vif-mediated degradation. The 293T cell clone A3G-Luc #5 from FIG. 2A was infected with either a Vif-null HIV-1 or a wild type HIV-1 expressing functional Vif (NL4-3). Vif expression from NL4-3 led to a decrease in A3G-Luc expression, relative to the Vif-null HIV-1 infected cells.

Figure 4:
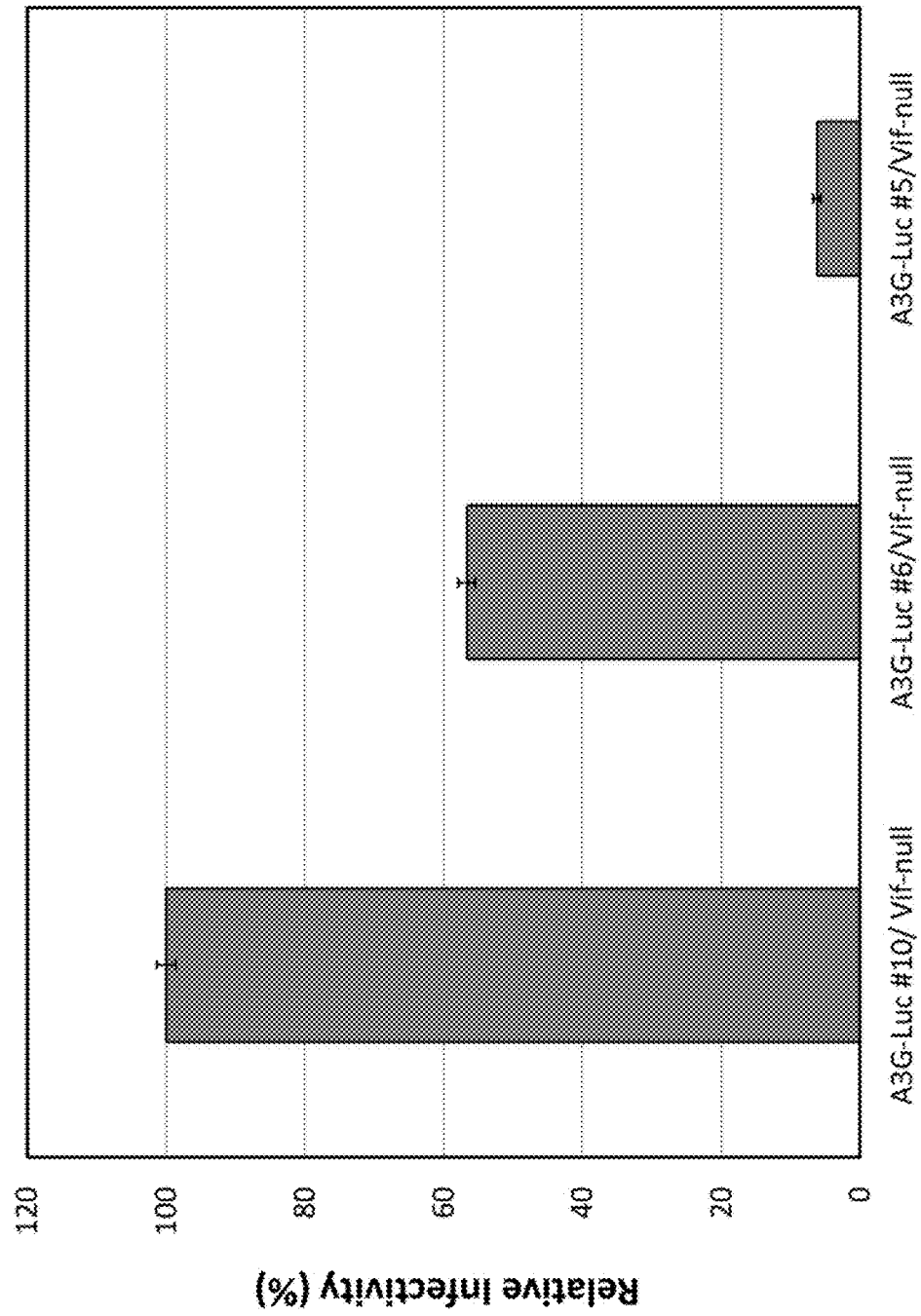

FIG. 4. A3G-Luc fusion proteins retain anti-HIV activity against Vif-null virus. The 293T cell lines stably expressing A3G-Luc from FIG. 2A were infected with Vif-null HIV-1. The infectivity of an equal amount of HIV-1 virions produced from these cells was less for viruses produced from the cell lines stably expressing more A3G-Luc. A3G-Luc #5-produced virus was less infectious than A3G-Luc #6-produced virus, which was also less infectious than A3G-Luc #10-produced virus.

Figure 5:
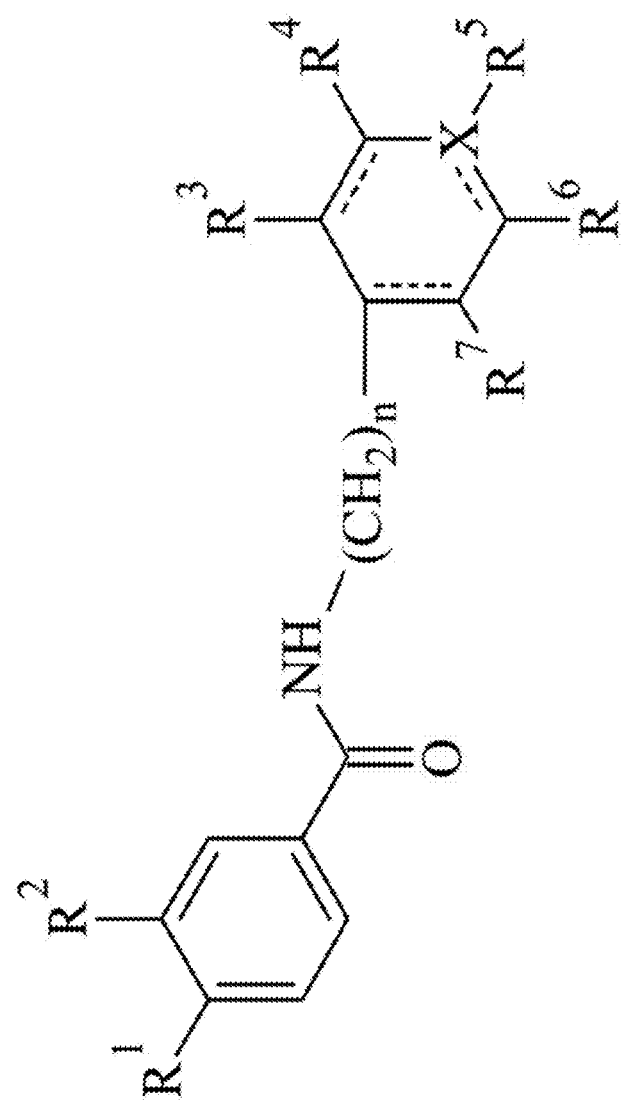

FIG. 5. Generic structure of 3-benzamide compounds of the present study.

Figure 6:
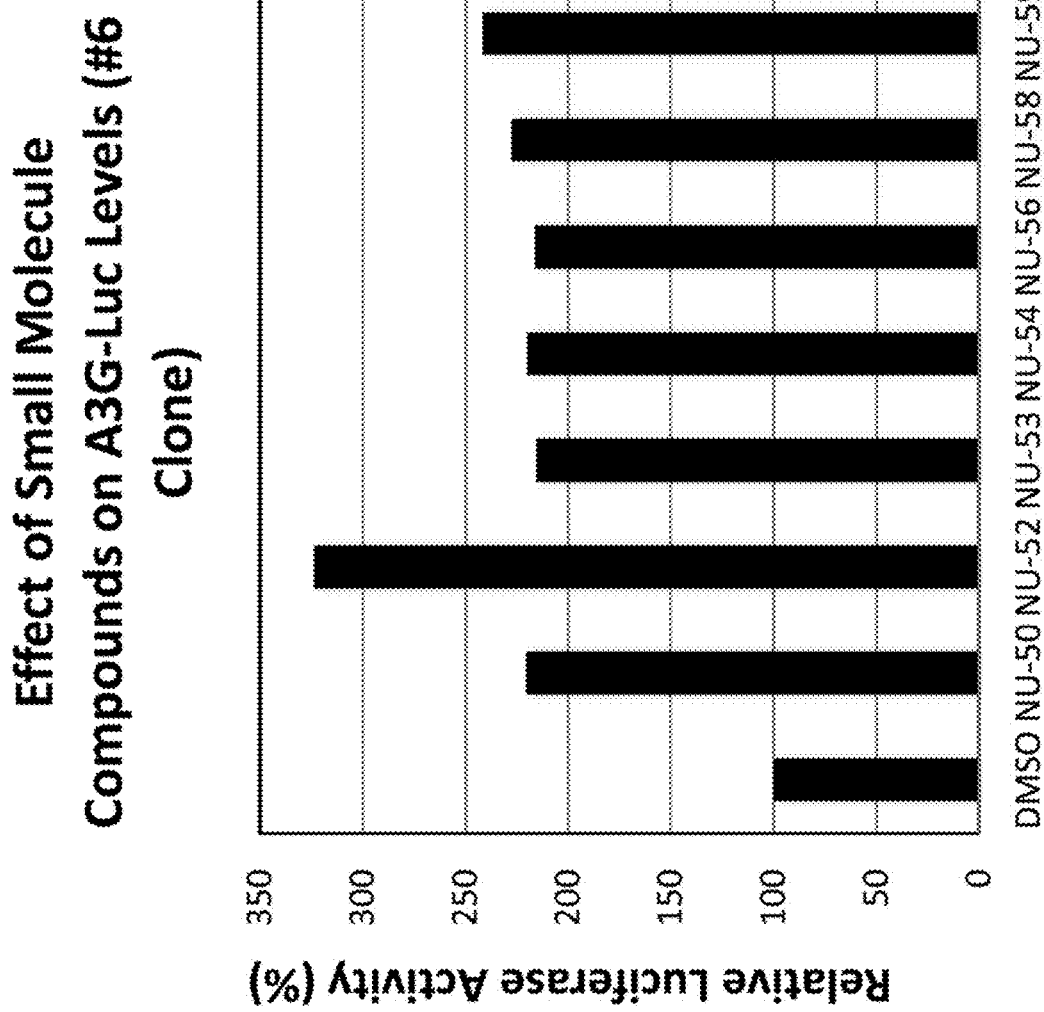

FIG. 6. 293T cell clone #6 stably co-expressing A3G-Luciferase fusion protein together with HIV-1 Vif was used. Small molecule compounds were tested for their effects on stability of A3G and inhibition of Vif activity against A3G by measuring luciferase activity, relative to treatment with control DMSO only. The relative % luciferase activity was higher after treatment with NU compounds than DMSO.

Figure 7:
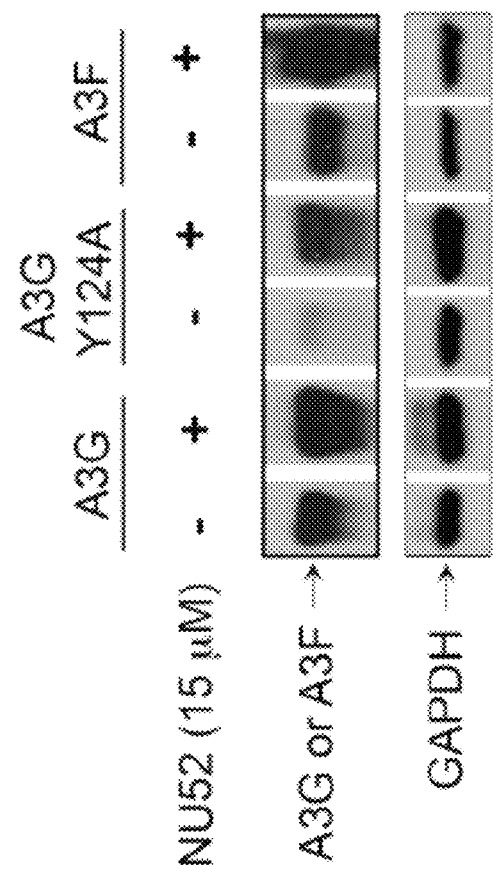

FIG. 7. 293T cells were transiently transfected with 400 ng of expression vectors for wild type A3G (A3G), a mutant A3G (A3G Y124A), and A3F (A3F) to test effect of NU52 treatment on steady state levels of the respective A3 protein, as detected by immunoblotting with respective antibodies, with GAPDH as loading control.

Figure 8:
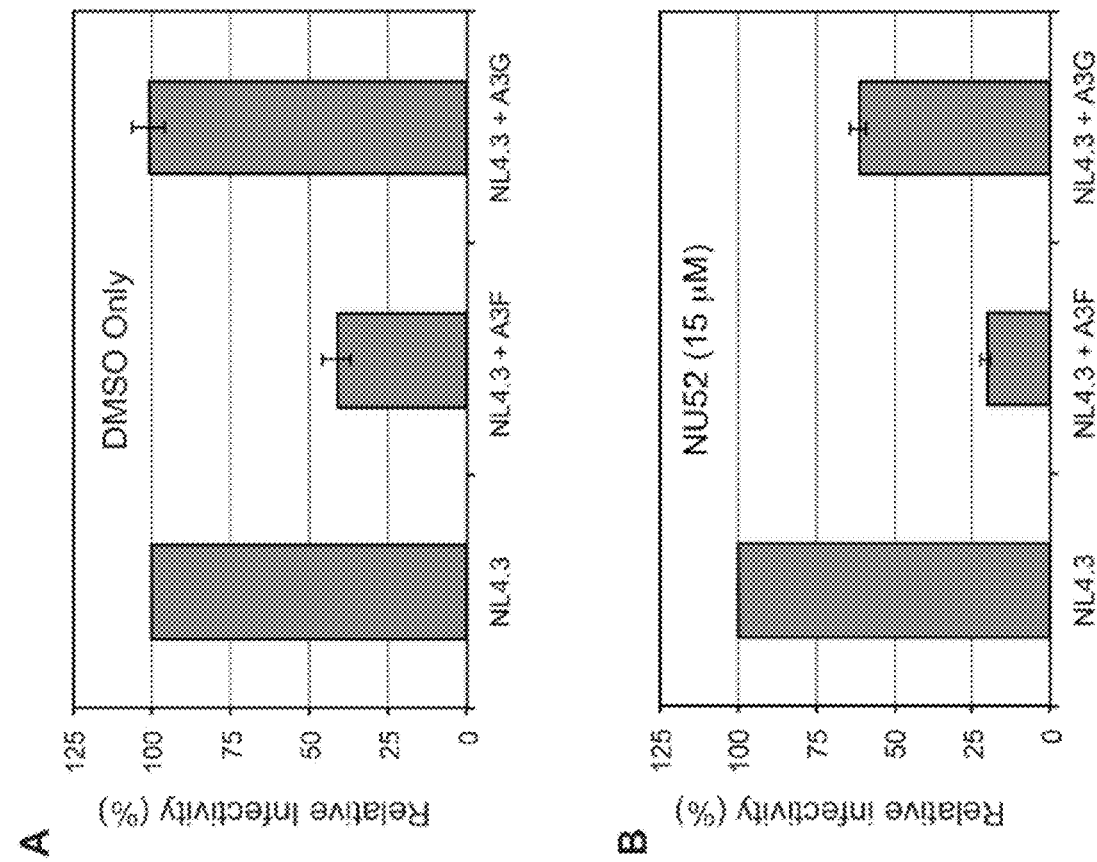

FIG. 8. 293T cells were co-transfected with 2 g of NL4.3 plasmid DNA and 400 ng of either control or A3F/G DNAs, with or without NU52. Infectivity of equal amounts of resulting viruses (normalized by HIV-1 p24 antigen) were measured using TZM-bl cells. NU-52 treatment of producer cell reduced infectivity of virus produced from those cells.

Figure 9B:
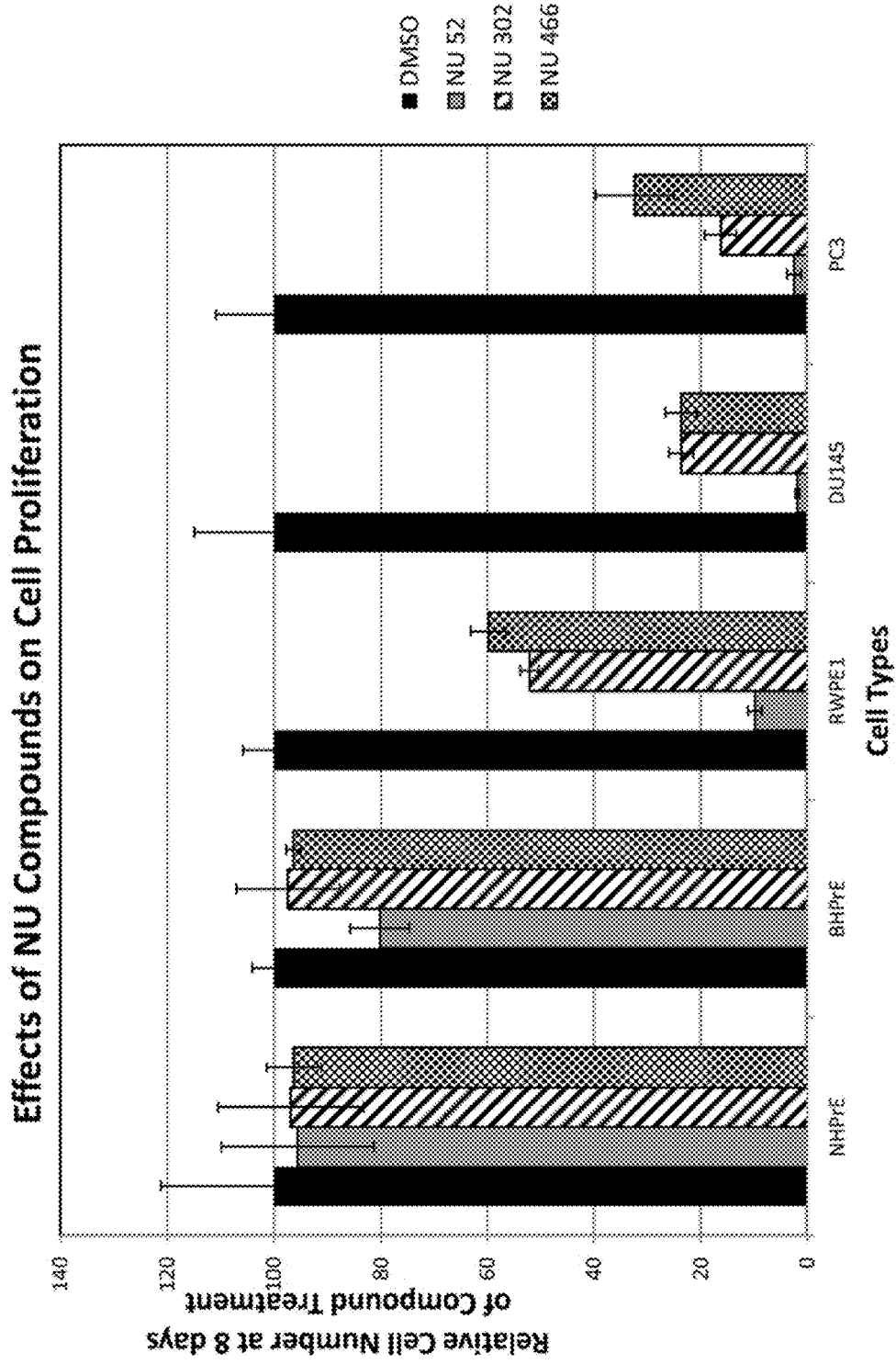

FIG. 9A and FIG. 9B. (A) Effect of listed compounds on cell numbers of various cancer cell lines. Selected lead compounds (NU52, NU302, NU466) killed or decreased proliferation of some breast cancer cell lines tested (T47D, MDA-MB-157 and MDA-MB-231) and a cervical cancer cell line tested (HeLa). The compounds did not kill or decrease proliferation of other breast cancer cell lines (MCF10A, MCF7) or a kidney epithelial cell line (HEK293). All the cancer cell lines with cell numbers decreased by the compounds had a non-functional, null, or mutant p53 phenotype. HEK293 cells do not express A3B. (B) The selected lead compounds killed or decreased proliferation of some prostate cancer cell lines tested (RWPE1, DU145, and PC3). Some of the prostate cancer cell lines tested were not affected (NHPrE, BHPrE). All the cancer cell lines with cell numbers decreased by the compounds had a non-functional, null, or mutant p53 phenotype.

Figure 10:
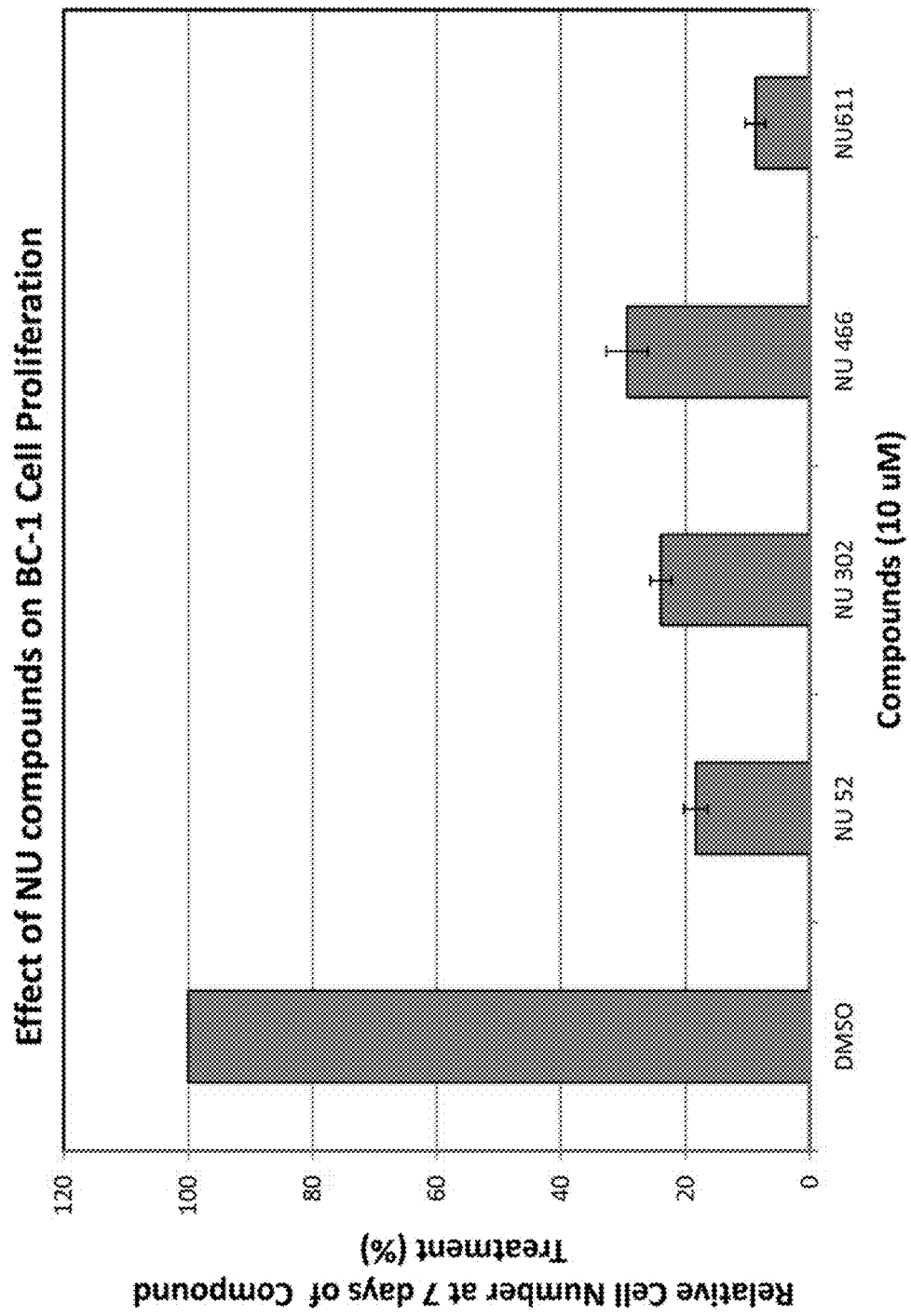

FIG. 10. A primary effusion lymphoma (PEL) cell line (BC-1, infected with both Kaposi's sarcoma herpesvirus and Epstein Barr Virus) is also killed by the listed compounds.

DETAILED DESCRIPTION

The present invention is described herein using several definitions, as set forth below and throughout the application.

As used in this specification and the claims, the singular forms "a," "an," and "the" include plural forms unless the context clearly dictates otherwise. For example, the term "a compound" should be interpreted to mean "one or more compounds" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Disclosed herein are benzamide compounds and the uses thereof for treating diseases and disorders in a patient in need thereof by increasing cellular levels of A3G and/or other members of the A3 family of proteins (e.g. A3F, A3H, and the like) in the patient. The disclosed compounds include 3-benzamide compounds that may be administered to treat an HIV-1 infection or cancer in a patient.

The disclosed compounds may be further described as follows. The disclosed compounds may be referred to as 3-benzamide compounds having a core structure as follows:

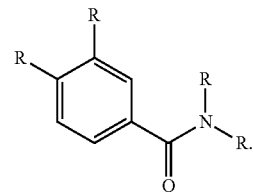

In particular, the disclosed compounds have a formula I as follows:

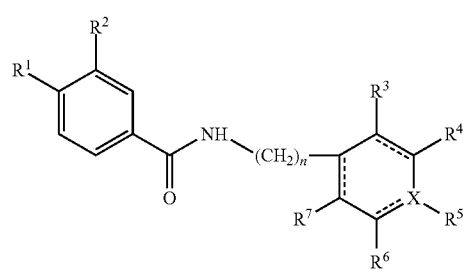

wherein:
n is 0 or 1 (preferably n is 0);
X is C or N (preferably X is C);
$R^1$ is hydroxyl, C1-C6-alkoxy (e.g., preferably methoxy), or

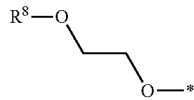

wherein
$R^8$ is C1-C6-alkyl (e.g., methyl),

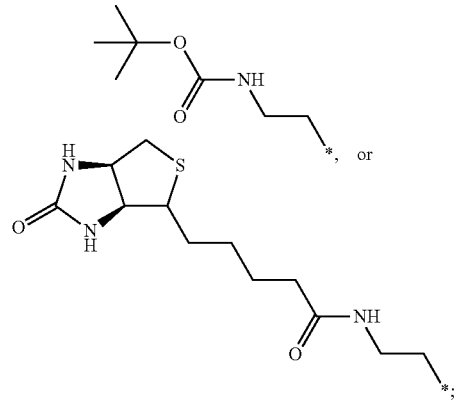

$R^2$ is H, nitro, amino, or

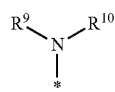

wherein
$R^9$ is H, or C1-C6-alkyl;
$R^{10}$ is C1-C6-alkyl, methyl sulfonyl, methylethyl sulfonyl, cyclopropyl sulfonyl, cyclobutyl sulfonyl, or

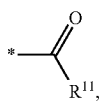

wherein
$R^{11}$ is H, C1-C6-alkyl optionally substituted with C1-C6 alkoxy (e.g., ethylmethoxy), hydroxyl, C1-C6-alkylamino (e.g. methylamino), C1-C6-dialkyl amino (e.g., dimethyl amino), phenyl, benzyl, benzo[1,3]dioxyl (e.g., benzo[1,3]diox-8-yl), pyridinyl (e.g., pyridin-2-yl, pyridin-3-yl, or pyridin-4-yl), C3-C6-cycloalkyl optionally substituted with methyl (e.g., methylcyclopropyl), C1-C6-alkoxy (e.g. methoxy), piperidinyl (e.g., N-piperidinyl), tetrahydropyranyl (e.g. tetrahydropyran-4-yl), tetrahydrofuranyl (e.g., tetrahydrofuran-2-yl), adamantanyl (e.g., adamantan-7-yl), or

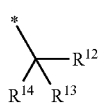

wherein
$R^{12}$ and $R^{13}$ are independently selected from H, C1-C6-alkyl optionally substituted with C1-C6-alkoxy, C1-C6-alkoxy, C1-C6 cycloalkyl, phenyl, C1-C6-alkylamino, C1-C6-dialkyl amino, or $R^{12}$ and $R^{13}$ together form a C3-C6 homocycle or a C3-C6 heterocycle, which optionally is unsaturated at one or more bonds;
$R^{14}$ is H or C1-C6-alkyl (preferably H); and
$R^3$, $R^4$, $R^5$, $R^6$, and $R^7$ are independently selected from H, C1-C6-alkoxy, halo, phenyl, 4-nitro phenoxyl, or $R^4$ and $R^5$ together form a C5-C7 homocycle (e.g., 1,3-dioxolane) or a C5-C7 heterocycle, which optionally is unsaturated at one or more bonds.

In some embodiments, the disclosed compounds may have a formula:

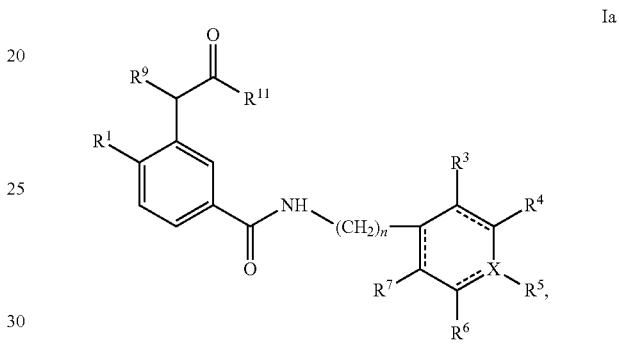

Ia or more specifically

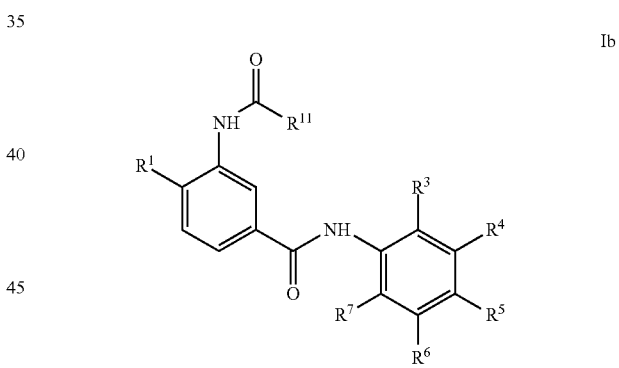

Ib wherein
$R^1$ is C1-C6-alkoxy (preferably methoxy);
$R^9$ is H, or C1-C6-alkyl;
$R^{11}$ is H, C1-C6-alkyl optionally substituted with C1-C6-alkoxy (e.g. ethylmethoxy), hydroxyl, C1-C6-alkylamino (e.g. methylamino), C1-C6-dialkylamino (e.g., dimethylamino), phenyl, benzyl, benzo[1,3]dioxyl (e.g., benzo[1,3]diox-8-yl), pyridinyl (e.g., pyridin-2-yl, pyridin-3-yl, or pyridin-4-yl), C3-C6-cycloalkyl optionally substituted with methyl (e.g., methylcyclopropyl), C1-C6-alkoxy (e.g. methoxy), piperidinyl (e.g., N-piperidinyl), tetrahydropyranyl (e.g. tetrahydropyran-4-yl), tetrahydrofuranyl (e.g., tetrahydrofuran-2-yl), or adamantanyl (e.g., adamantan-7-yl); and
$R^3$, $R^4$, $R^5$, $R^6$, and $R^7$ are independently selected from H, C1-C6-alkoxy, and halo (e.g., chloro or fluoro).

The term "alkyl" as contemplated herein includes a straight-chain or branched alkyl radical in all of its isomeric forms. Similarly, the term "alkoxy" refers to any alkyl radical which is attached via by an oxygen atom (i.e., a radical represented as "alkyl-O—*").

As used herein, an asterisk "*" is used to designate the point of attachment for any radical group or substituent group.

In some embodiments of the disclosed compounds, $R^1$ is methoxy. For example, the disclosed compounds may have a formula Ic as follows:

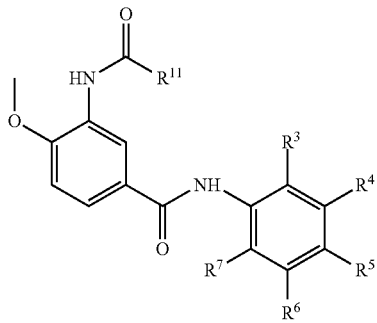

Ic

In some embodiments of the disclosed compounds, one or more of $R^4$, $R^5$, are $R^6$ are methoxy. For example, the disclosed compounds may have a formula Id or Ie as follows:

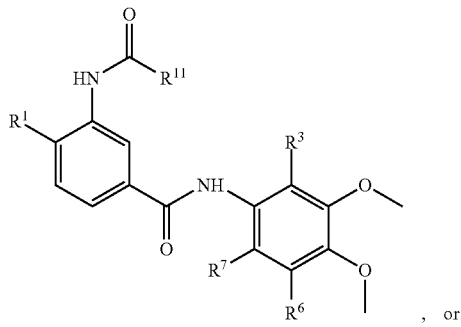

Id

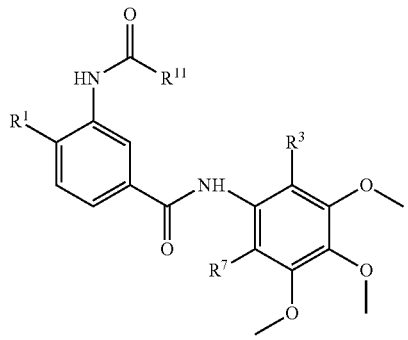

Ie

In some embodiments of the disclosed compounds, one or more of $R^4$, $R^5$, are $R^6$ are halo (e.g., chloro or fluoro). For example, the disclosed compounds may have a formula If as follows:

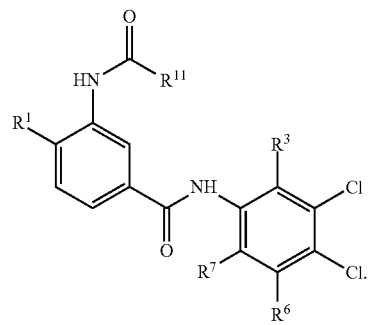

If

The following table provides a list of exemplary compounds as disclosed herein.

| Compound No. | Structure |
|---|---|
| NU 49 | 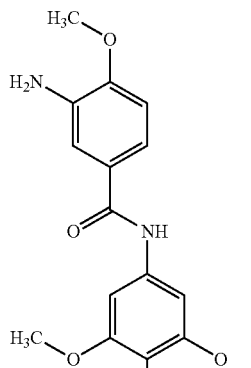 |

-continued

| Compound No. | Structure |
|---|---|
| NU 50 | *(structure: N-(benzo[d][1,3]dioxol-5-yl)-3-isobutyramido-4-methoxybenzamide)* |
| NU 52 | *(structure: N-(3,4-dichlorophenyl)-3-isobutyramido-4-methoxybenzamide)* |
| NU 54 | *(structure: 3-isobutyramido-4-methoxy-N-(4-methoxyphenyl)benzamide)* |

-continued
| Compound No. | Structure |
| --- | --- |
| NU 56 | 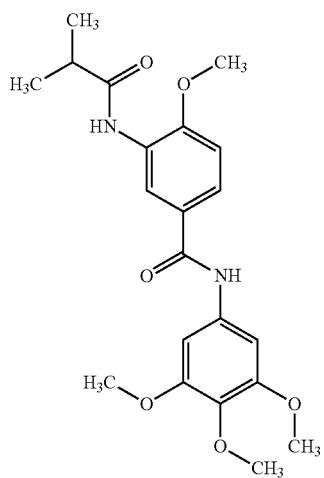 [SMILES: COc1ccc(C(=O)Nc2cc(OC)c(OC)c(OC)c2)cc1NC(=O)C(C)C] |
| NU 57 | 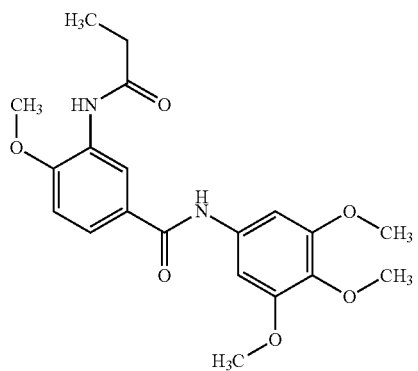 [SMILES: CCC(=O)Nc1cc(C(=O)Nc2cc(OC)c(OC)c(OC)c2)ccc1OC] |
| NU 58 | 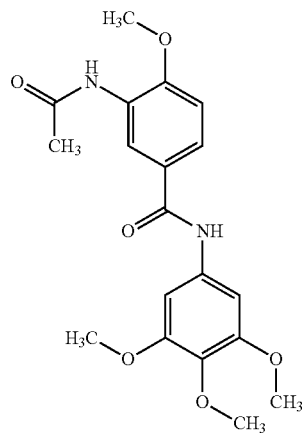 [SMILES: COc1ccc(C(=O)Nc2cc(OC)c(OC)c(OC)c2)cc1NC(C)=O] |

-continued
| Compound No. | Structure |
|---|---|
| NU 302 | 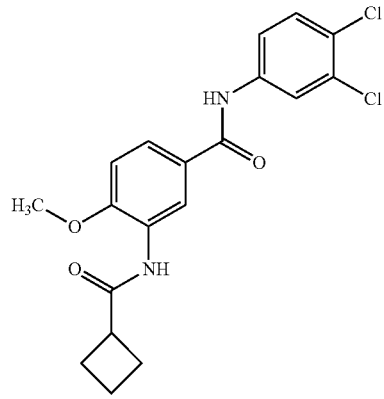 [SMILES: COc1ccc(C(=O)Nc2ccc(Cl)c(Cl)c2)cc1NC(=O)C1CCC1] |
| NU 303 | 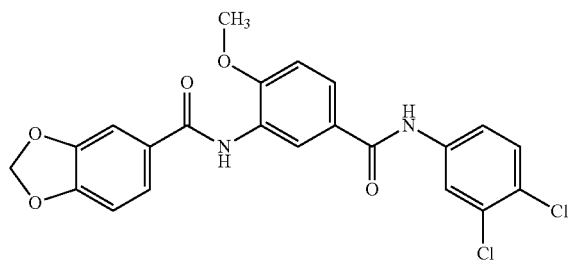 [SMILES: COc1ccc(C(=O)Nc2ccc(Cl)c(Cl)c2)cc1NC(=O)c1ccc2c(c1)OCO2] |
| NU 304 | 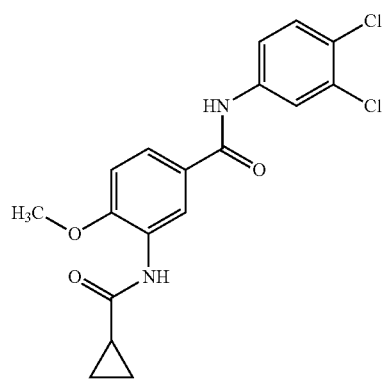 [SMILES: COc1ccc(C(=O)Nc2ccc(Cl)c(Cl)c2)cc1NC(=O)C1CC1] |
| NU 305 | 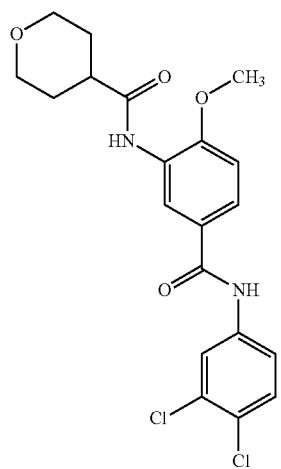 [SMILES: COc1ccc(C(=O)Nc2ccc(Cl)c(Cl)c2)cc1NC(=O)C1CCOCC1] |

| Compound No. | Structure |
|---|---|
| NU 306 | 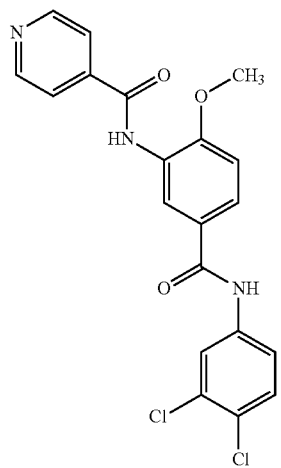 |
| NU 307 | 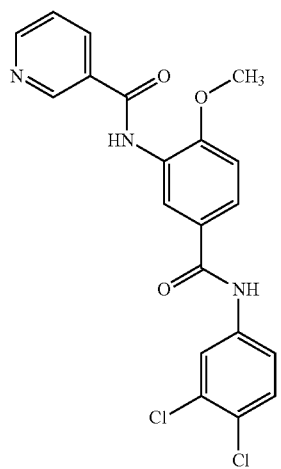 [SMILES: COc1ccc(C(=O)Nc2ccc(Cl)c(Cl)c2)cc1NC(=O)c1cccnc1] |
| NU 308 | 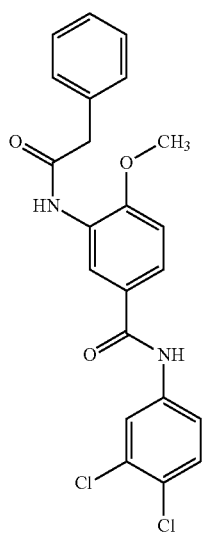 [SMILES: COc1ccc(C(=O)Nc2ccc(Cl)c(Cl)c2)cc1NC(=O)Cc1ccccc1] |

-continued
| Compound No. | Structure |
|---|---|
| NU 309 | 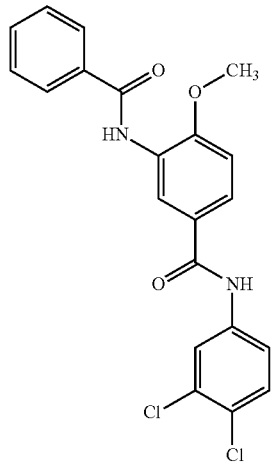 [SMILES: COc1ccc(C(=O)Nc2ccc(Cl)c(Cl)c2)cc1NC(=O)c1ccccc1] |
| NU 452 | 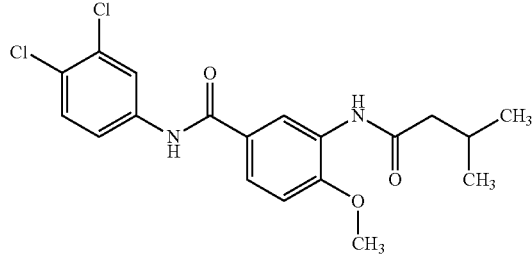 [SMILES: COc1ccc(C(=O)Nc2ccc(Cl)c(Cl)c2)cc1NC(=O)CC(C)C] |
| NU 453 | 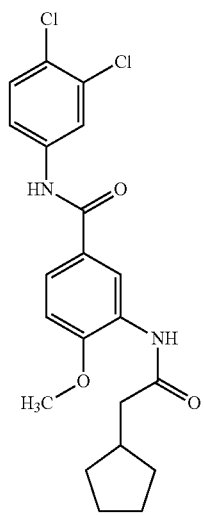 [SMILES: COc1ccc(C(=O)Nc2ccc(Cl)c(Cl)c2)cc1NC(=O)CC1CCCC1] |

-continued
| Compound No. | Structure |
|---|---|
| NU 454 | 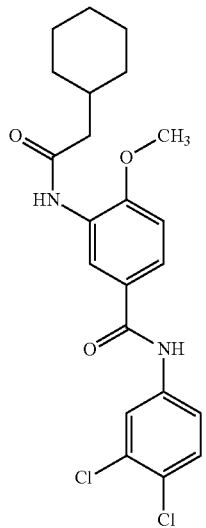 [SMILES: COc1ccc(C(=O)Nc2ccc(Cl)c(Cl)c2)cc1NC(=O)CC1CCCCC1] |
| NU 455 | 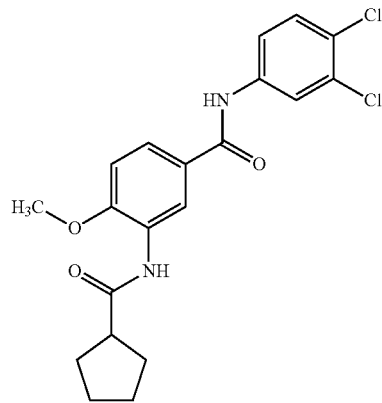 |
| NU 456 | 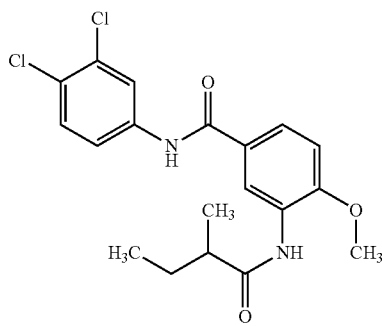 [SMILES: CCC(C)C(=O)Nc1cc(C(=O)Nc2ccc(Cl)c(Cl)c2)ccc1OC] |

| Compound No. | Structure |
|---|---|
| NU 457 | 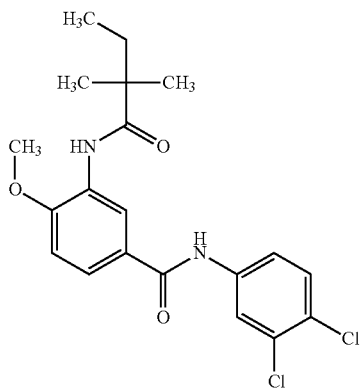 [SMILES: CCC(C)(C)C(=O)Nc1cc(C(=O)Nc2ccc(Cl)c(Cl)c2)ccc1OC] |
| NU 458 | 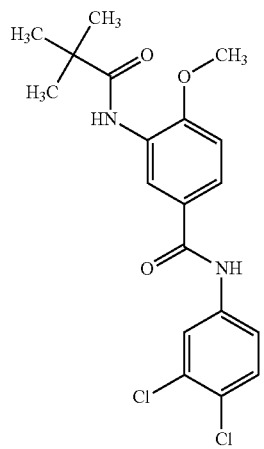 [SMILES: COc1ccc(C(=O)Nc2ccc(Cl)c(Cl)c2)cc1NC(=O)C(C)(C)C] |
| NU 459 | 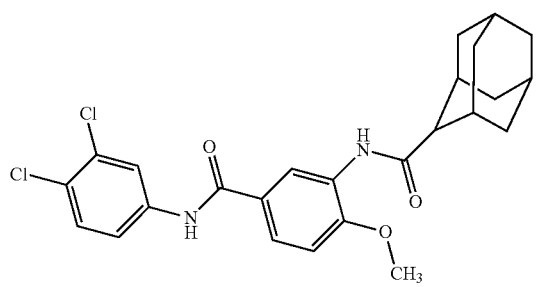 [SMILES: COc1ccc(C(=O)Nc2ccc(Cl)c(Cl)c2)cc1NC(=O)C1C2CC3CC(C2)CC1C3] |
| NU 460 | 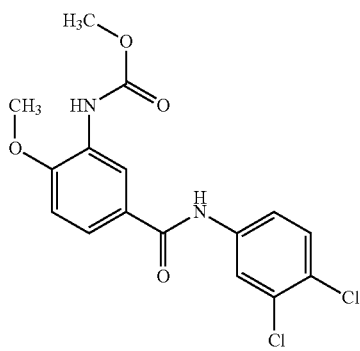 [SMILES: COC(=O)Nc1cc(C(=O)Nc2ccc(Cl)c(Cl)c2)ccc1OC] |

| Compound No. | Structure |
|---|---|
| NU 461 | 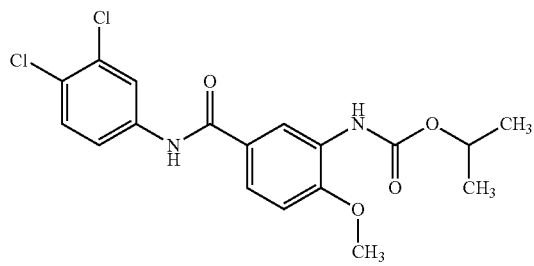 [SMILES: COc1ccc(C(=O)Nc2ccc(Cl)c(Cl)c2)cc1NC(=O)OC(C)C] |
| NU 462 | 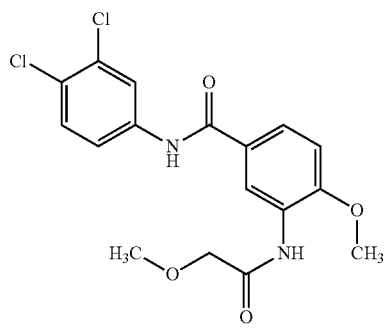 [SMILES: COCC(=O)Nc1cc(C(=O)Nc2ccc(Cl)c(Cl)c2)ccc1OC] |
| NU 463 | 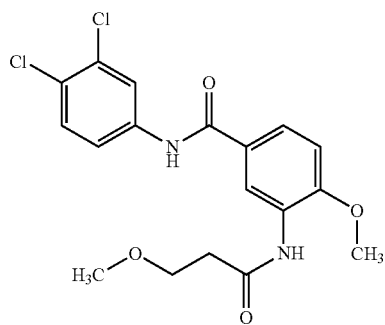 [SMILES: COCCC(=O)Nc1cc(C(=O)Nc2ccc(Cl)c(Cl)c2)ccc1OC] |
| NU 464 | 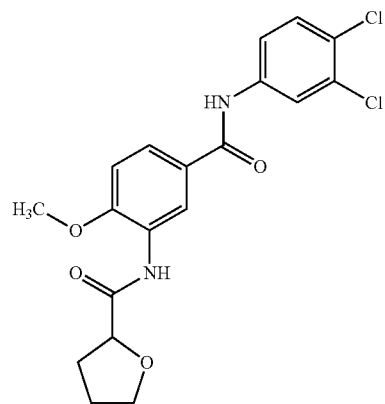 |

-continued
| Compound No. | Structure |
|---|---|
| NU 465 | 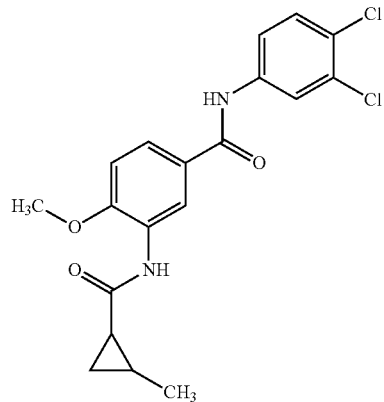 [SMILES: COc1ccc(C(=O)Nc2ccc(Cl)c(Cl)c2)cc1NC(=O)C1CC1C] |
| NU 466 | 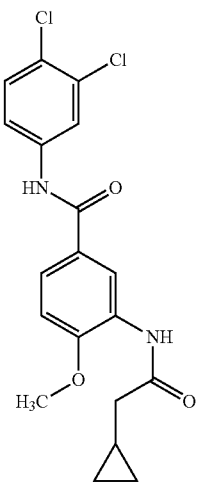 [SMILES: COc1ccc(C(=O)Nc2ccc(Cl)c(Cl)c2)cc1NC(=O)CC1CC1] |
| NU 467 | 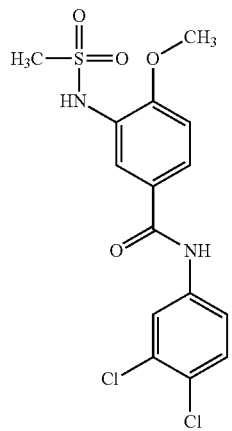 [SMILES: COc1ccc(C(=O)Nc2ccc(Cl)c(Cl)c2)cc1NS(C)(=O)=O] |

| Compound No. | Structure |
|---|---|
| NU 468 | 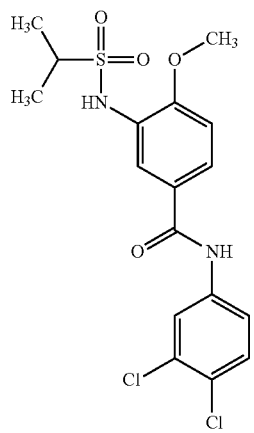 [SMILES: COc1ccc(C(=O)Nc2ccc(Cl)c(Cl)c2)cc1NS(=O)(=O)C(C)C] |
| NU 469 | 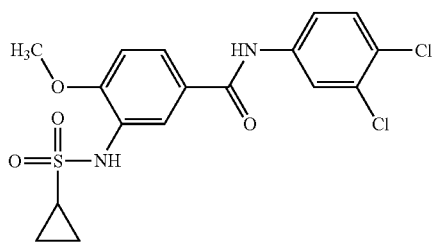 [SMILES: COc1ccc(C(=O)Nc2ccc(Cl)c(Cl)c2)cc1NS(=O)(=O)C1CC1] |
| NU 470 | 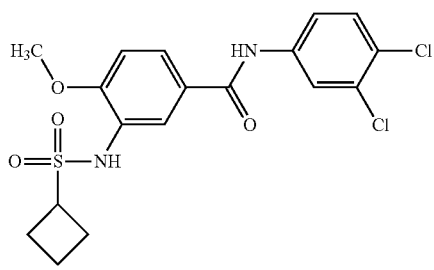 [SMILES: COc1ccc(C(=O)Nc2ccc(Cl)c(Cl)c2)cc1NS(=O)(=O)C1CCC1] |
| NU 471 | 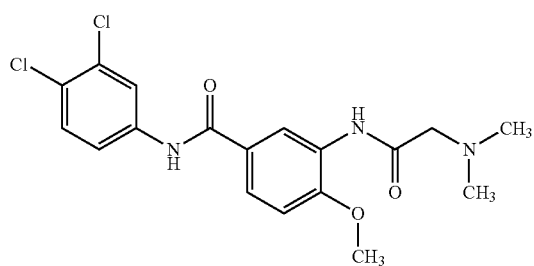 |

| Compound No. | Structure |
|---|---|
| NU 472 | 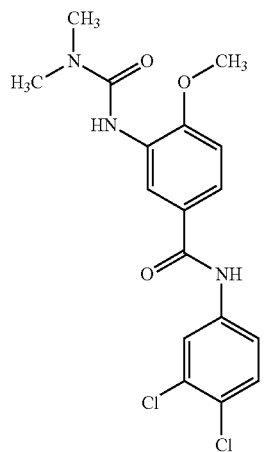 [SMILES: COc1ccc(C(=O)Nc2ccc(Cl)c(Cl)c2)cc1NC(=O)N(C)C] |
| NU 473 | 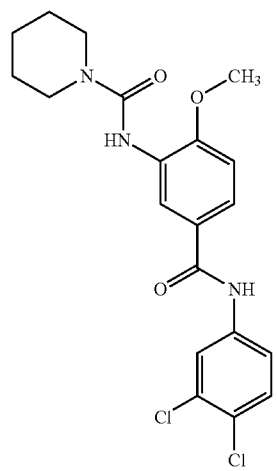 [SMILES: COc1ccc(C(=O)Nc2ccc(Cl)c(Cl)c2)cc1NC(=O)N1CCCCC1] |
| NU 474 | 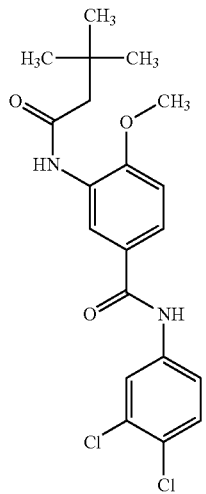 [SMILES: COc1ccc(C(=O)Nc2ccc(Cl)c(Cl)c2)cc1NC(=O)CC(C)(C)C] |

-continued
| Compound No. | Structure |
|---|---|
| NU 564 | 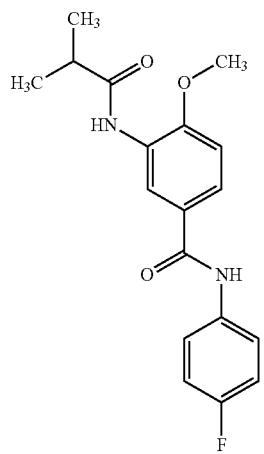 [SMILES: COc1ccc(C(=O)Nc2ccc(F)cc2)cc1NC(=O)C(C)C] |
| NU 565 | 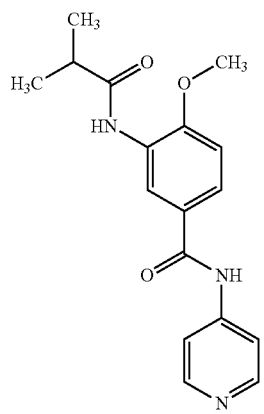 [SMILES: COc1ccc(C(=O)Nc2ccncc2)cc1NC(=O)C(C)C] |
| NU 566 | 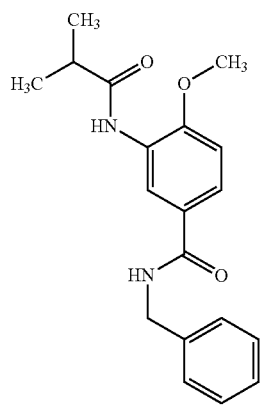 [SMILES: COc1ccc(C(=O)NCc2ccccc2)cc1NC(=O)C(C)C] |

-continued
| Compound No. | Structure |
|---|---|
| NU 567 | 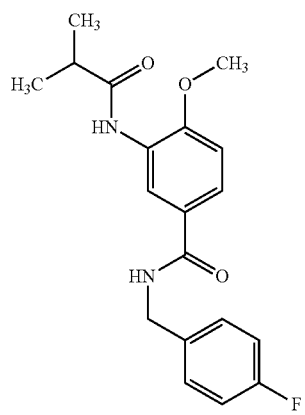 [SMILES: COc1ccc(C(=O)NCc2ccc(F)cc2)cc1NC(=O)C(C)C] |
| NU 568 | 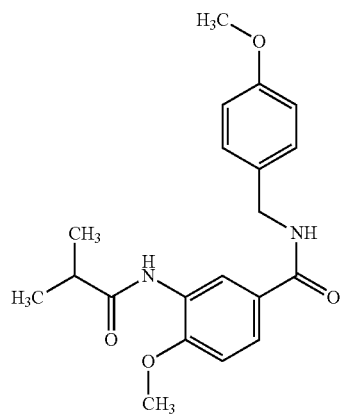 [SMILES: COc1ccc(CNC(=O)c2ccc(OC)c(NC(=O)C(C)C)c2)cc1] |
| NU 569 | 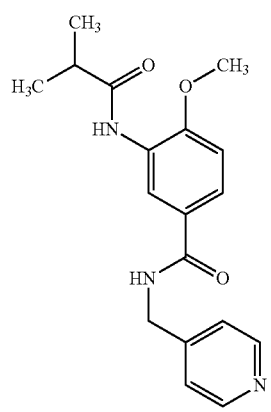 [SMILES: COc1ccc(C(=O)NCc2ccncc2)cc1NC(=O)C(C)C] |
| NU 570 | 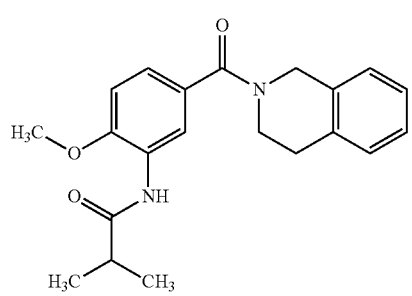 [SMILES: COc1ccc(C(=O)N2CCc3ccccc3C2)cc1NC(=O)C(C)C] |

| Compound No. | Structure |
|---|---|
| NU 571 | 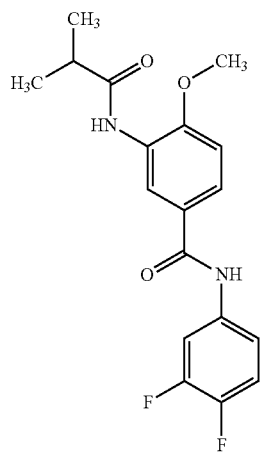 [SMILES: COc1ccc(C(=O)Nc2ccc(F)c(F)c2)cc1NC(=O)C(C)C] |
| NU 572 | 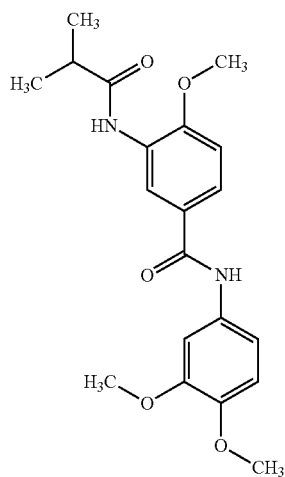 [SMILES: COc1ccc(C(=O)Nc2ccc(OC)c(OC)c2)cc1NC(=O)C(C)C] |
| NU 573 | 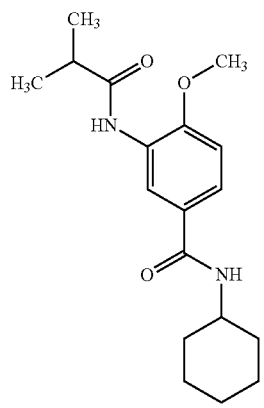 [SMILES: COc1ccc(C(=O)NC2CCCCC2)cc1NC(=O)C(C)C] |

| Compound No. | Structure |
|---|---|
| NU 611 | 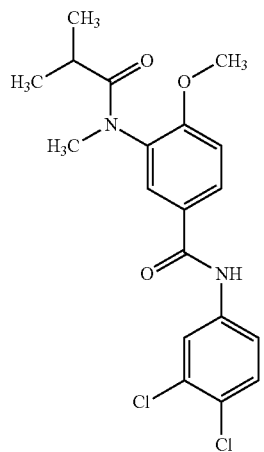 [SMILES: COc1ccc(C(=O)Nc2ccc(Cl)c(Cl)c2)cc1N(C)C(=O)C(C)C] |
| NU 612 | 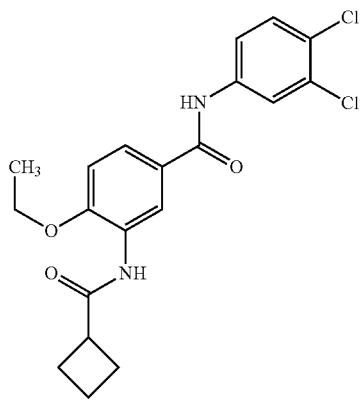 [SMILES: CCOc1ccc(C(=O)Nc2ccc(Cl)c(Cl)c2)cc1NC(=O)C1CCC1] |
| NU 613 | 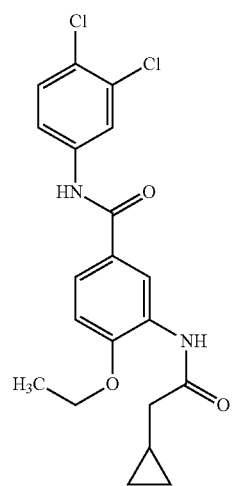 |
| NU 614 | 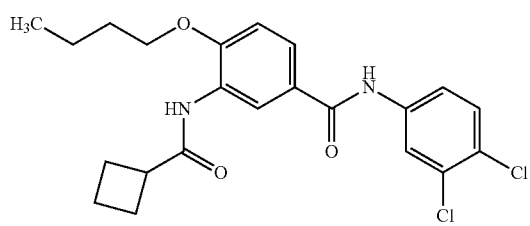 [SMILES: CCCCOc1ccc(C(=O)Nc2ccc(Cl)c(Cl)c2)cc1NC(=O)C1CCC1] |

-continued
| Compound No. | Structure |
|---|---|
| NU 615 | 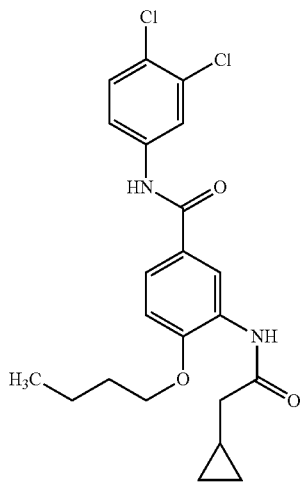 [SMILES: CCCCOc1ccc(C(=O)Nc2ccc(Cl)c(Cl)c2)cc1NC(=O)CC1CC1] |
| NU 616 | 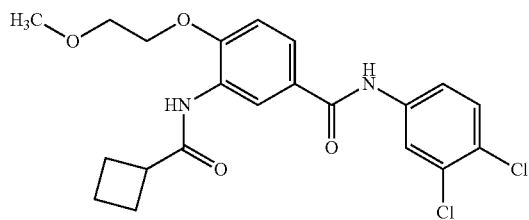 [SMILES: COCCOc1ccc(C(=O)Nc2ccc(Cl)c(Cl)c2)cc1NC(=O)C1CCC1] |
| NU 617 | 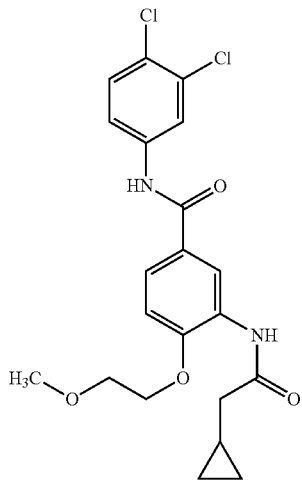 [SMILES: COCCOc1ccc(C(=O)Nc2ccc(Cl)c(Cl)c2)cc1NC(=O)CC1CC1] |
| NU 124 | 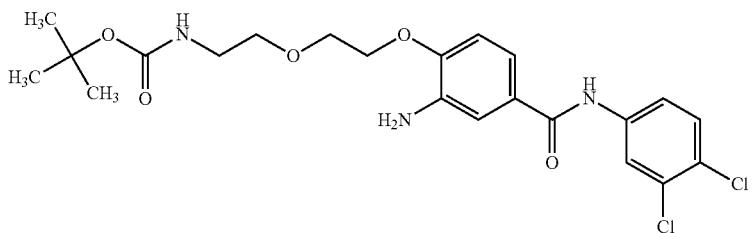 [SMILES: CC(C)(C)OC(=O)NCCOCCOc1ccc(C(=O)Nc2ccc(Cl)c(Cl)c2)cc1N] |

| Compound No. | Structure |
|---|---|
| NU 125 | (structure) |
| NU 126 | (structure) |
| NU 127 | (structure) |
| NU 128 | (structure) |

Also disclosed are pharmaceutical compositions comprising the disclosed compounds or pharmaceutically acceptable salts thereof and a pharmaceutical carrier. The disclosed pharmaceutical compositions may comprise an effective amount of the disclosed compounds for increasing levels of A3G and/or other members of the A3 family of proteins (e.g., A3F, A3H, and the like) after the composition is administered to a patient in need thereof. As such, therapeutic methods also are contemplated herein and suitable patients for the treatment methods may include, but are not limited to patients having an HIV-1 infection and/or cancer.

As used herein, the term "patient" may be used interchangeably with the term "subject" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

The disclosed compounds, compositions, and methods may be utilized to treat a patient in need thereof. A "patient in need thereof" is intended to include a patient having or at risk for developing diseases and disorders such as diseases and disorders treated by administering a compound that increases the cellular levels of A3G and/or other members of the A3 family of proteins in the patient. Diseases and disorders that may be treated by the disclosed compounds, compositions, and methods may include HIV-infection and cell proliferative diseases and disorders which may include cancer and hyperproliferative disorders. A patient in need thereof may include a patient having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

A patient in need thereof may refer to a human subject having or at risk for developing a disease or disorder that is associated with A3G activity. The term "A3G" and the term "APOBEC3G" may be used interchangeably herein to refer to "apolipoprotein B mRNA-editing enzyme, catalytic polypeptide-like 3G." A3G belongs to the APOBEC superfamily of proteins which play an important role in innate anti-viral immunity, particular against HIV-1. A3G is a cytidine deaminase that catalyzes the deamination of cytidine to uridine in a single-stranded DNA substrate. A3G is expressed in certain cells, referred to as non-permissive cells, in which HIV-1 cannot produce virions that are infectious in the absence of certain HIV-1 proteins that can counteract the inhibitory effect of A3G (e.g.; HIV-1 virion infectivity factor, Vif). Increasing A3G (or decreasing Vif function) also partially decreases infectious virus production when A3G-containing cells are infected with a Vif-positive HIV-1 as well. As such, a patient in need thereof may include a patient having or at risk for developing infection by HIV-1, where the presently disclosed compounds may be administered to increase cellular levels of A3G to help block HIV replication. Other members of the A3 family of proteins may include, but are not limited to A3F and A3H.

Over-expression of the A3 family of proteins and cytidine deamination of nuclear DNA has been implicated in pathogenesis of several types of cancer, including cancers of breast, lung, head/neck, cervical, ovarian, bladder, prostate and multiple myeloma and certain lymphomas occurring in HIV patients. It is well described that one of the functions of p53 tumor suppressor protein is to allow repair of potentially lethal DNA damage. Thus, we hypothesize that cells lacking functional p53 will be more prone to synthetic lethality from excess A3B-mediated genome hypermutation. As such, a patient in need thereof may include a patient having or at risk for developing a cell proliferative disorders such as cancer, and in particular, a cell proliferative disorder or cancer that is characterized by the low p53 biological activity.

The compounds disclosed herein preferably increase cellular levels of A3G and/or other members of the A3 family of proteins by any biological mechanism of action (e.g., by protecting A3G and/or other members of the A3 family of proteins from degradation and/or by increasing expression of A3G and/or other members of the A3 family of proteins). Cellular levels of A3G and/or other members of the A3 family of proteins may be assessed utilizing methods known in the art, including nucleic acid assays, protein assays, immune assays, and enzymatic assays known in the art. In some embodiments, the compounds increase cellular levels of A3G and/or other members of the A3 family of proteins relative to a control (e.g., by at least about 10%, 20%, 30%, 40%, 50%, 60%, 70%, 80%, 90%, or more). In other embodiments, an $EC_{50}$ value for the compound in regard to increasing cellular levels of A3G and/or other members of the A3 family of proteins may be determined and preferably the compound has an $EC_{50}$ value of less than about 100 μM, 50 μM, 10 μM, 5 μM, or 1 μM.

The compounds disclosed herein (e.g., compounds of formula I, Ia, Ib, Ic, Id, Ie, and If) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that increases cellular levels of A3G and/or other members of the A3 family of proteins may be administered as a single compound or in combination with another compound that increases cellular levels of A3G and/or other members of the A3 family of proteins or that has a different pharmacological activity (e.g., a different pharmacological activity for treating infection by HIV-1 or for treating cancer).

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with the biological activity of A3G and/or other members of the A3 family of proteins, including administering an effective amount of a compound that increases cellular levels of A3G and/or other members of the A3 family of proteins.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| Active Ingredient | 80 mg |
| --- | --- |
| Starch | 59 mg |
| Microcrystaline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| Active Ingredient | 100 mg |
| --- | --- |
| Mannitol | 100 mg |
| 5N Sodium hydroxide | 200 ml |
| Purified water to total | 5 ml |

EXAMPLES

The following Examples are illustrative and should not be interpreted as limiting the scope of the claims.

Example I

Chemistry

General Experimental

All chemical reagents were obtained from commercial suppliers and used without further purification unless otherwise stated. Anhydrous solvents were purchased from Sigma-Aldrich, and dried over 3 Å molecular sieves when necessary. DCM and THF were purified by passage through a bed of activated alumina. Normal-phase flash column chromatography was performed using Biotage KP-Sil 50 μm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light or iodine vapor. Liquid chromatography/mass spectrometry (LCMS) was performed on a Waters Acquity-H UPLC system with a 2.1 mm×50 mm, 1.7 jam, reversed phase BEH C18 column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent.

Total ion current traces were obtained for electrospray positive and negative ionization (ESI+/ESI−). Proton ($^1$H) and carbon ($^{13}$C) NMR spectra were recorded on a Bruker Avance III w/ direct cryoprobe spectrometer. Chemical shifts were reported in ppm (δ) and were referenced using residual non-deuterated solvent as an internal standard. The chemical shifts for 1H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. In some cases, overlapping signals occurred in the $^{13}$C NMR spectra.

Preparation of Intermediates and Final Compounds

Scheme 1. Reagents and conditions: (a) SOCl$_2$, EtOAc, reflux, 3 h (b) R$_1$-PhNH$_2$, TEA, DCM, 0° C. to rt, 2 h (c) SnC$_2$.2H$_2$O, EtOH, 80° C., 2 h (d) R$_2$COCl, TEA, DCM, 0° C. to rt, 2 h.

Step a: Synthesis of 4-methoxy-3-nitrobenzoyl chloride 1a

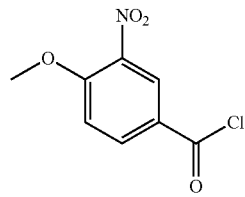

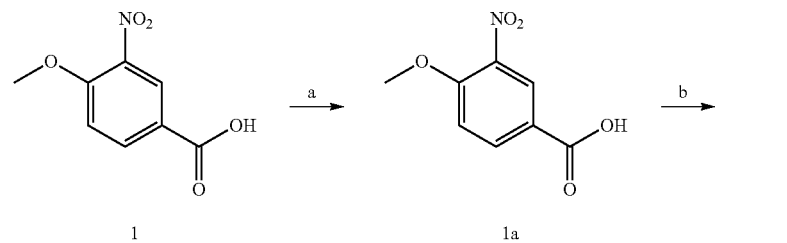

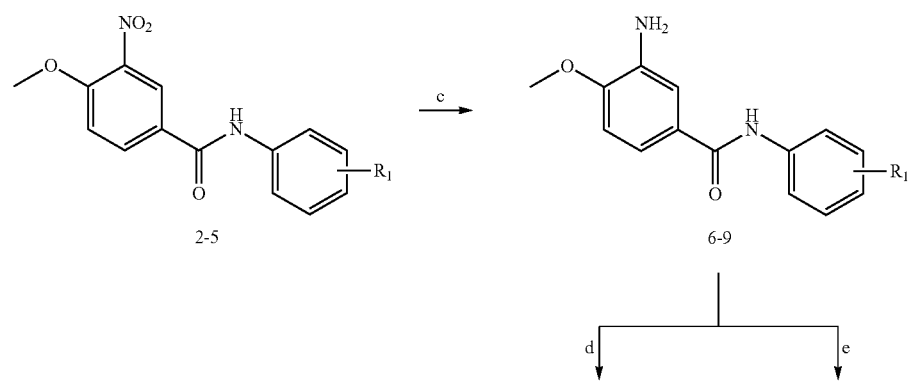

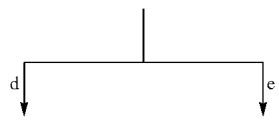

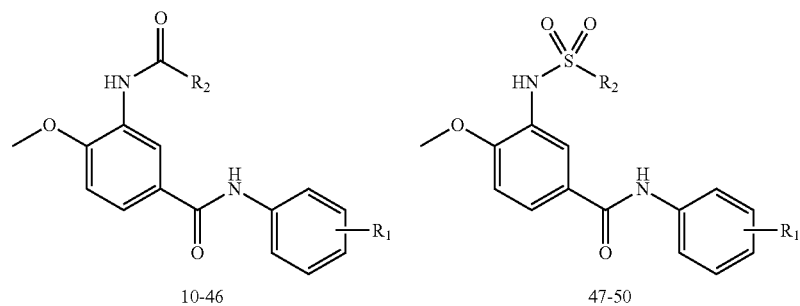

Thionyl chloride (10 ml, 137 mmol) was added slowly to a solution of 4-methoxy-3-nitrobenzoic acid 1 (5 g, 25.4 mmol) in EtOAc (50 ml). The resulting suspension was refluxed (80° C.) for 3 h upon which it became a clear solution. The reaction was cooled to rt and the solvents were removed under reduced pressure. The solid obtained was dried under high vacuum to yield 4-methoxy-3-nitrobenzoyl chloride 1a (4.22 g, 77%) as a tan-colored solid. $^1$H NMR (500 MHz, CDCl$_3$) δ 4.08 (s, 3H), 7.21 (d, J=8.85 Hz, 1H), 8.30 (dd, J=9.16, 2.44 Hz, 1H), 8.61 (d, J=2.14 Hz, 1H).

Step b: General Procedure for the Synthesis of Amides 2-5

A solution of 4-methoxy-3-nitrobenzoyl chloride 1a (1.0 equiv) in DCM (2 mL/mmol) was cooled to 0° C. and treated with TEA (1.2 equiv). To this solution was added the appropriate amine R$_1$-PhNH$_2$ (1.0 equiv) and the resulting mixture was stirred at 0° C. for 2 h. Water and 1N HCl were added to the reaction mixture followed by removal of DCM under reduced pressure. The solid obtained was collected by vacuum filtration, washed with water and methanol and dried under high vacuum to give the respective amides.

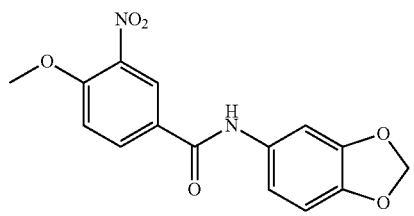 [SMILES: COc1ccc(C(=O)Nc2ccc3c(c2)OCO3)cc1[N+](=O)[O-]]

N-(benzo[d][1,3]dioxol-5-yl)-4-methoxy-3-nitrobenzamide (2)

Prepared according to the general procedure described in Step b using 4-methoxy-3-nitrobenzoyl chloride 1a (0.75 g, 3.48 mmol) to afford N-(benzo[d][1,3]dioxol-5-yl)-4-methoxy-3-nitrobenzamide 2 (1 g, 90%). MS (ESI): mass calcd. for C$_{15}$H$_{12}$N$_2$O$_6$, 316.27; m/z found, 317.18 [M+H]+.

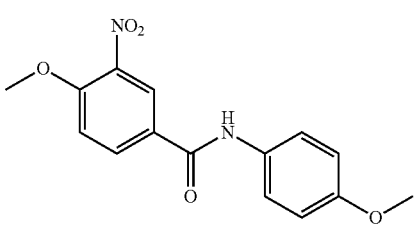

4-Methoxy-N-(4-methoxyphenyl)-3-nitrobenzamide (3)

Prepared according to the general procedure described in Step b using 4-methoxy-3-nitrobenzoyl chloride 1a (0.75 g, 3.48 mmol) to afford 4-methoxy-N-(4-methoxyphenyl)-3-nitrobenzamide 3 (0.84 g, 80%). MS (ESI): mass calcd. for C$_{15}$H$_{14}$N$_2$O$_5$, 302.28; m/z found, 303.21 [M+H]+.

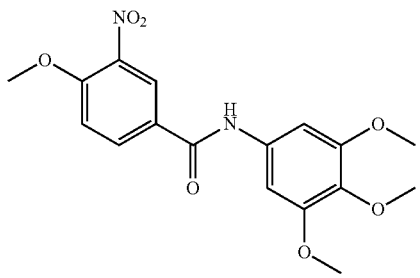

4-Methoxy-3-nitro-N-(3,4,5-trimethoxyphenyl)benzamide (4)

Prepared according to the general procedure described in Step b using 4-methoxy-3-nitrobenzoyl chloride 1a (1.5 g, 6.96 mmol) to afford 4-methoxy-3-nitro-N-(3,4,5-trimethoxyphenyl)benzamide 4 (2.24 g, 89%). MS (ESI): mass calcd. for C$_{17}$H$_{18}$N$_2$O$_7$, 362.33; m/z found, 363.36 [M+H]+.

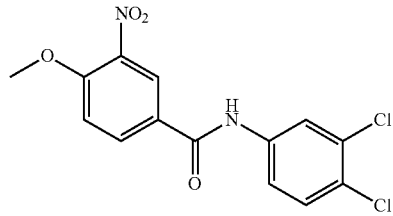

N-(3,4-Dichlorophenyl)-4-methoxy-3-nitrobenzamide (5)

Prepared according to the general procedure described in Step b using 4-methoxy-3-nitrobenzoyl chloride 1a (2 g, 9.28 mmol) to afford N-(3,4-dichlorophenyl)-4-methoxy-3-nitrobenzamide 5 (2.85 g, 90%) as an off-white solid. MS (ESI): mass calcd. for C$_{14}$H$_{10}$C$_{12}$N$_2$O$_4$, 340.0; m/z found, 340.9 [M+H]+; $^1$H NMR (500 MHz, acetone-d$_6$) δ 4.08 (s, 3H), 7.51 (d, J=8.85 Hz, 1H), 7.52 (d, J=8.85 Hz, 1H), 7.76 (dd, J=8.70, 2.59 Hz, 1H), 8.19 (d, J=2.44 Hz, 1H), 8.31 (dd, J=8.85, 2.44 Hz, 1H), 8.47 (d, J=2.14 Hz, 1H), 9.90 (brs, 1H).

Step c: General Procedure for the Synthesis of Amines 6-9

To a solution of the respective nitrobenzamide 2-5 (1.0 equiv) in ethanol (4 mL/mmol) was added tin(II) chloride dihydrate (5 equiv). The resulting suspension was stirred at 80° C. for 2 h. The reaction was cooled to rt and diluted with EtOAc. Saturated NaHCO$_3$ was added and the mixture was stirred at rt for 15 min. The solids were filtered and washed extensively with EtOAc. The filtrate was washed with saturated NaHCO$_3$, H$_2$O and brine, dried over anhydrous Na$_2$SO$_4$, and evaporated to give a crude solid that was triturated with diethyl ether to yield the respective amines.

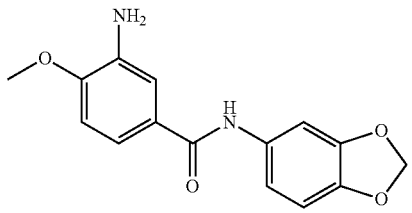

3-Amino-N-(benzo[d][1,3]dioxol-5-yl)-4-methoxybenzamide (6)

Prepared according to general procedure described in Step c using N-(benzo[d][1,3]dioxol-5-yl)-4-methoxy-3-nitrobenzamide 2 to afford 3-amino-N-(benzo[d][1,3]dioxol-5-yl)-4-methoxybenzamide 6. (0.45 g, 66%). MS (ESI): mass calcd. for $C_{15}H_{14}N_2O_4$, 286.28; m/z found, 287.20 [M+H]+.

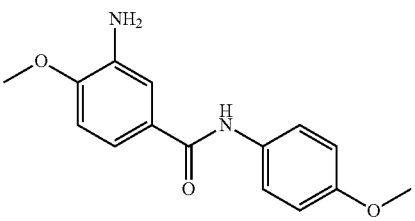

3-Amino-4-methoxy-N-(4-methoxyphenyl)benzamide (7)

Prepared according to general procedure described in Step c using 4-methoxy-N-(4-methoxyphenyl)-3-nitrobenzamide 3 to afford 3-amino-4-methoxy-N-(4-methoxyphenyl)benzamide 7. (0.58 g, 86%). MS (ESI): mass calcd. for $C_{15}H_{16}N_2O_3$, 272.30; m/z found, 273.19 [M+H]+.

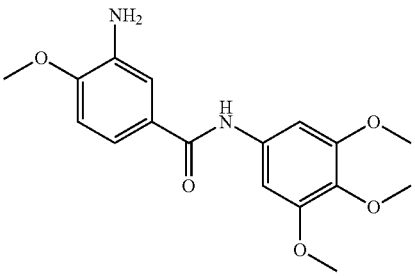

3-Amino-4-methoxy-N-(3,4,5-trimethoxyphenyl)benzamide (8)

Prepared according to general procedure described in Step c using 4-methoxy-3-nitro-N-(3,4,5-trimethoxyphenyl)benzamide 4 to afford 3-amino-4-methoxy-N-(3,4,5-trimethoxyphenyl)benzamide 8. (0.65 g, 47%). MS (ESI): mass calcd. for $C_{17}H_{20}N_2O_5$, 332.35; m/z found, 333.24 [M+H]+.

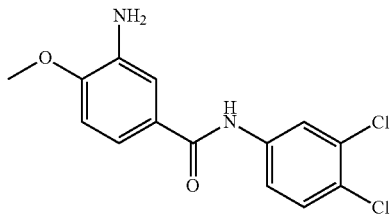 [SMILES: COc1ccc(C(=O)Nc2ccc(Cl)c(Cl)c2)cc1N]

3-Amino-N-(3,4-dichlorophenyl)-4-methoxybenzamide (9)

Prepared according to general procedure described in Step c using N-(3,4-dichlorophenyl)-4-methoxy-3-nitrobenzamide 5 (2.8 g, 8.21 mmol) to afford 3-amino-N-(3,4-dichlorophenyl)-4-methoxybenzamide 9 (1.6 g, 62.6%) as an off-white solid. MS (ESI): mass calcd. for $C_{14}H_{12}Cl_2N_2O_2$, 310.03; m/z found, 311.20 [M+H]+; $^1$H NMR (500 MHz, acetone-$d_6$) δ 3.90 (s, 3H), 6.90 (d, J=8.24 Hz, 1H), 7.28 (dd, J=8.39, 2.29 Hz, 1H), 7.33 (d, J=2.44 Hz, 1H), 7.50 (d, J=8.85 Hz, 1H), 7.76 (dd, J=8.85, 2.44 Hz, 1H), 8.22 (d, J=2.75 Hz, 1H), 9.47 (brs, 1H).

Step d: General Procedure for the Synthesis of Substituted Bisaryl Amides 10-46

TEA (1.1 equiv) was added to a solution of bisaryl amine $R_1$—$NH_2$ (1.0 equiv) in DCM (10 mL/1 mmol). The mixture was cooled to 0° C. and the appropriate acid chloride $R_2$COCl (1.1 equiv) was added to it gradually. The reaction mixture was stirred from 0° C. to rt over a period of 2 h. The solvents were removed under reduced pressure and the resulting residue was purified by flash column chromatography on silica gel to yield the respective bisaryl amides.

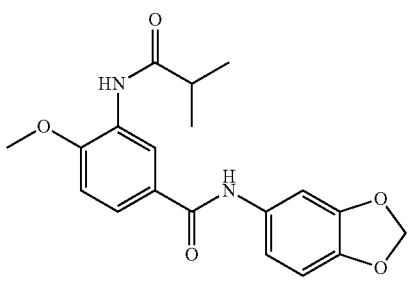 [SMILES: COc1ccc(C(=O)Nc2ccc3c(c2)OCO3)cc1NC(=O)C(C)C]

N-(benzo[d][1,3]dioxol-5-yl)-3-isobutyramido-4-methoxybenzamide (10)

Prepared according to general procedure described in Step d using 3-amino-N-(benzo[d][1,3]dioxol-5-yl)-4-methoxybenzamide 6 to afford the title compound 10. (20.1 mg, 67%). MS (ESI): mass calcd. for $C_{19}H_{20}N_2O_5$, 356.37; m/z found, 357.30 [M+H]+; $^1$H NMR (500 MHz, CDCl$_3$) δ 1.30 (d, 3H), 2.61-2.63 (m, 1H), 3.98 (s, 3H), 5.98 (s, 2H), 6.78 (d, J=8.20 Hz, 1H), 6.92 (dd, J=8.35, 2.05 Hz, 1H), 7.00 (d, J=8.51 Hz, 1H), 7.37 (d, J=1.89 Hz, 1H), 7.80 (dd, J=8.67, 2.36 Hz, 1H), 7.90 (bs, 1H), 7.93 (bs, 1H), 8.90 (d, J=2.21 Hz, 1H).

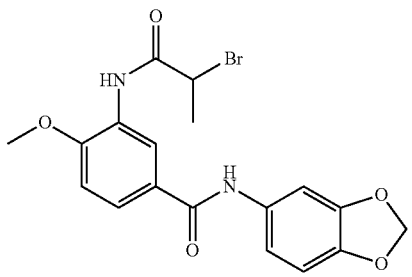 [SMILES: COc1ccc(C(=O)Nc2ccc3c(c2)OCO3)cc1NC(=O)C(C)Br]

N-(benzo[d][1,3]dioxol-5-yl)-3-(2-bromopropanamido)-4-methoxy benzamide (11)

Prepared according to general procedure described in Step d 3-amino-N-(benzo[d][1,3]dioxol-5-yl)-4-methoxybenzamide 6 to afford the title compound 11. (9.5 mg, 26%). $^1$H NMR (500 MHz, CDCl$_3$) δ 2.00 (d, 3H, J=7.25 Hz), 4.01 (s, 3H), 4.57-4.63 (m, 1H), 5.98 (s, 2H), 6.79 (d, I=8.20 Hz, 1H), 6.92 (dd, I=8.35, 2.05 Hz, 1H), 7.00-7.04 (m, 1H), 7.37 (d, I=1.89 Hz, 1H), 7.83 (m, 1H), 8.74 (bs, 1H), 8.77 (bs, 1H), 8.82 (d, I=1.89 Hz, 1H).

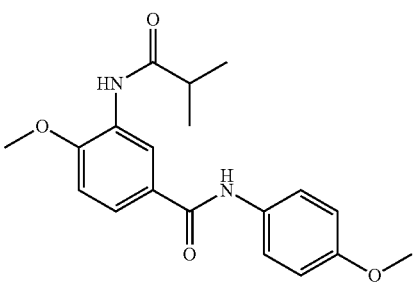

3-Isobutyramido-4-methoxy-N-(4-methoxyphenyl)benzamide (12)

Prepared according to general procedure described in Step d using 3-amino-4-methoxy-N-(4-methoxyphenyl)benzamide 7 to afford the title compound 12. (45.1 mg, 53%). $^1$H NMR (500 MHz, CDCl$_3$) δ 1.28-1.32 (d, 3H, J=6.65 Hz), 2.57-2.65 (m, 1H), 3.82 (s, 3H), 3.98 (s, 3H), 6.90 (d, J=9.14 Hz, 2H), 7.00 (d, J=8.83 Hz, 1H), 7.55 (d, J=9.14 Hz, 2H), 7.80-7.84 (m, 1H), 7.86, (bs, 1H), 7.90 (bs, 1H), 8.93 (d, J=1.89 Hz, 1H).

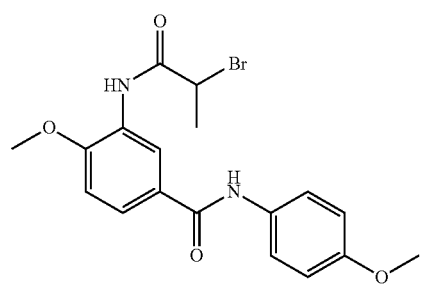

3-(2-Bromopropanamido)-4-methoxy-N-(4-methoxyphenyl)benzamide (13)

Prepared according to general procedure described in Step d using 3-amino-4-methoxy-N-(4-methoxyphenyl)benzamide 7 to afford the title compound 13. $^1$H NMR (500 MHz, CDCl$_3$) δ 2.00 (d, 3H, J=6.95 Hz), 3.82 (s, 3H), 4.01 (s, 3H), 4.59-4.60 (m, 1H), 6.92 (d, J=9.14 Hz, 2H) 7.02 (d, J=8.83 Hz, 1H), 7.55 (d, J=9.14 Hz, 2H), 7.80-7.82 (m, 1H), 8.74 (bs, 1H), 8.77 (bs, 1H), 8.84 (d, J=1.89 Hz, 1H).

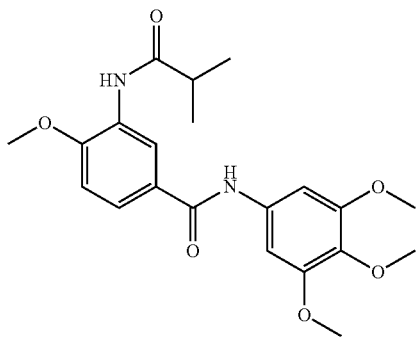

3-Isobutyramido-4-methoxy-N-(3,4,5-trimethoxyphenyl)benzamide (14)

Prepared according to general procedure described in Step d using 3-amino-4-methoxy-N-(3,4,5-trimethoxyphenyl)benzamide 8 to afford the title compound 14. $^1$H NMR (500 MHz, CDCl$_3$) δ 1.28 (m, 6H), 2.57-2.66 (m, 1H), 3.84 (s, 3H), 3.88-3.90 (s, 6H), 3.99 (s, 3H), 7.01 (s, 2H), 7.84 (dd, J=8.51, 2.21 Hz, 1H), 7.93 (s, 1H), 8.01 (s, 1H), 8.92 (d, J=2.21 Hz, 1H).

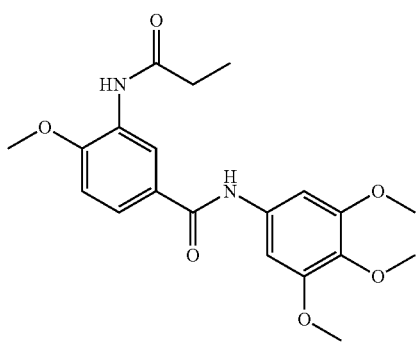

4-Methoxy-3-propionamido-N-(3,4,5-trimethoxyphenyl)benzamide (15)

Prepared according to general procedure described in Step d using 3-amino-4-methoxy-N-(3,4,5-trimethoxyphenyl)benzamide 8 to afford the title compound 15. $^1$H NMR (500 MHz, CDCl$_3$) δ 1.25-1.32 (m, 3H), 2.46-2.53 (m, 2H), 3.85 (s, 3H), 3.90 (s, 6H), 3.99 (s, 3H,) 7.00 (s, 2H), 7.73-7.77 (m, 1H), 8.07 (s, 1H) 8.43 (s, 1H), 8.91 (d, J=2.21 Hz, 1H) 9.06 (s, 1H).

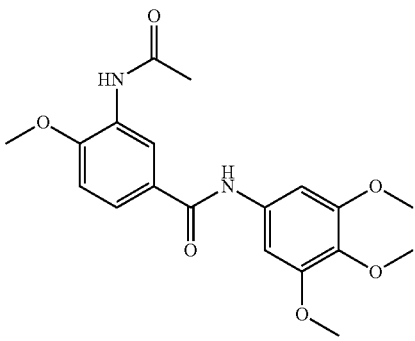

3-Acetamido-4-methoxy-N-(3,4,5-trimethoxyphenyl)benzamide (16)

Prepared according to general procedure described in Step d using 3-amino-4-methoxy-N-(3,4,5-trimethoxyphenyl)benzamide 8 to afford the title compound 16. $^1$H NMR (500 MHz, CDCl$_3$) δ 2.28 (s, 3H), 3.85 (s, 3H), 3.90 (s, 6H), 3.98 (s, 3H), 7.01 (s, 2H), 7.73-7.77 (m, 1H), 8.10 (s, 1H), 8.43 (s, 1H) 8.86 (d, J=2.21 Hz, 1H), 9.03 (m, 1H).

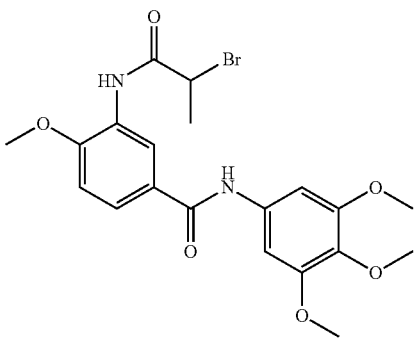

3-(2-Bromopropanamido)-4-methoxy-N-(3,4,5-trimethoxy phenyl) benzamide (17)

Prepared according to general procedure described in Step d using 3-amino-4-methoxy-N-(3,4,5-trimethoxyphenyl)benzamide 8 to afford the title compound 17. $^1$H NMR (500 MHz, CDCl$_3$) δ 2.01 (d, J=6.94 Hz, 3H), 3.85 (s, 3H), 3.90 (s, 6H), 4.02 (s, 3H), 4.45-4.62 (m, 1H), 6.99 (s, 2H), 7.76-7.80 (m, 1H), 8.08 (s, 1H), 8.39-8.42 (m, 1H), 8.72-8.76 (m, 1H), 8.95-8.99 (m, 1H).

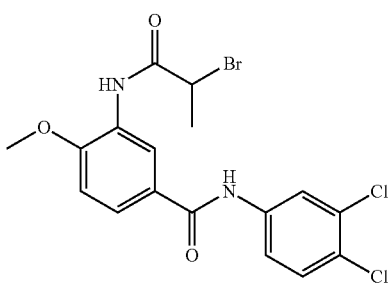 [SMILES: COc1ccc(C(=O)Nc2ccc(Cl)c(Cl)c2)cc1NC(=O)C(C)Br]

3-(2-Bromopropanamido)-N-(3,4-dichlorophenyl)-4-methoxy benzamide (18)

Prepared according to general procedure described in Step d using 3-amino-N-(3,4-dichlorophenyl)-4-methoxybenzamide 9 to afford the title compound 18. $^1$H NMR (500 MHz, CDCl$_3$) δ 2.00 (d, J=7.25 Hz, 3H), 4.01 (s, 3H), 4.56-4.63 (m, 1H), 7.04 (d, J=8.83 Hz, 1H), 7.40-7.43 (m, 1H), 7.49-7.52 (m, 1H), 7.83 (dd, J=8.51, 2.21 Hz, 1H), 7.93 (d, J=2.21 Hz, 1H), 8.06 (s, 1H), 8.75 (br. s., 1H), 8.82 (d, J=2.21 Hz, 1H).

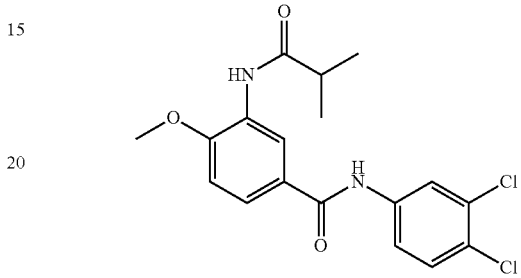

N-(3,4-dichlorophenyl)-3-isobutyramido-4-methoxybenzamide (19)

Prepared according to the general procedure using 3-amino-N-(3,4-dichlorophenyl)-4-methoxybenzamide 9 (20 mg, 0.064 mmol) and purified by flash column chromatography on silica gel (0-50% EtOAc in Hex) to afford N-(3,4-dichlorophenyl)-3-isobutyramido-4-methoxybenzamide 19 (12 mg, 61%) as a white solid. MS (ESI): mass calcd. for C$_{18}$H$_{18}$C$_{12}$N$_2$O$_3$, 380.07; m/z found, 381.25 [M+H]+; $^1$H NMR (500 MHz, CDCl$_3$) δ 1.28 (s, 3H), 1.29 (s, 3H), 2.56-2.64 (m, 1H), 3.97 (s, 3H), 6.99 (d, J=8.54 Hz, 1H), 7.38 (d, J=8.85 Hz, 1H), 7.50 (dd, J=8.70, 2.29 Hz, 1H), 7.79 (dd, J=8.70, 1.68 Hz, 1H), 7.88 (brs, 1H), 7.93 (d, J=2.14 Hz, 1H), 8.27 (s, 1H), 8.86 (d, J=1.83 Hz, 1H); $^{13}$C NMR (126 MHz, CDCl$_3$) δ 19.60, 37.00, 56.07, 110.21, 116.97, 119.46, 121.90, 125.19, 126.73, 127.15, 130.34, 132.60, 137.85, 150.63, 165.09, 175.85.

3-(Cyclobutanecarboxamido)-N-(3,4-dichlorophenyl)-4-methoxy benzamide (20)

Prepared according to the general procedure described in Step d using 3-amino-N-(3,4-dichlorophenyl)-4-methoxybenzamide 9 (20 mg, 0.064 mmol) and purified by flash column chromatography on silica gel (0-50% EtOAc in Hex) to afford 3-(cyclobutanecarboxamido)-N-(3,4-dichlorophenyl)-4-methoxybenzamide 20 (17 mg, 67%) as a white solid. MS (ESI): mass calcd. for $C_{19}H_{18}C_{12}N_2O_3$, 392.07; m/z found, 393.20 [M+H]+; $^1$H NMR (500 MHz, CDCl$_3$) δ 1.92-2.03 (m, 1H), 2.03-2.11 (m, 1H), 2.23-2.34 (m, 2H), 2.37-2.46 (m, 2H), 3.25 (t, J=8.39 Hz, 1H), 3.97 (s, 3H), 7.00 (d, J=8.54 Hz, 1H), 7.41 (d, J=8.85 Hz, 1H), 7.53 (dd, J=8.70, 2.29 Hz, 1H), 7.75 (brs, 1H), 7.80 (dd, J=8.54, 2.44 Hz, 1H), 7.95 (d, J=2.44 Hz, 1H), 8.28 (brs, 1H), 8.88 (d, J=2.14 Hz, 1H); $^{13}$C NMR (126 MHz, CDCl$_3$) δ 18.11, 25.39, 41.15, 56.06, 110.24, 116.75, 119.45, 121.91, 125.05, 126.70, 127.30, 130.41, 137.76, 150.56, 165.05, 173.80.

Hex) to afford N-(3,4-dichlorophenyl)-4-methoxy-3-(3-methylbutanamido)benzamide 22 (32 mg, 63%) as a white solid. MS (ESI): mass calcd. for $C_{19}H_{20}C_{12}N_2O_3$, 394.09; m/z found, 395.0 [M+H]+; $^1$H NMR (500 MHz, CDCl$_3$) δ 1.03 (s, 3H), 1.05 (s, 3H), 2.19-2.27 (m, 1H), 2.29-2.31 (m, 2H), 3.96 (s, 3H), 6.98 (d, J=8.85 Hz, 1H), 7.34-7.42 (m, 1H), 7.47-7.53 (m, 1H), 7.76-7.83 (m, 2H), 7.92 (d, J=2.44 Hz, 1H), 8.26 (s, 1H), 8.85 (d, J=2.14 Hz, 1H); $^{13}$C NMR (126 MHz, CDCl$_3$) δ 22.62, 26.40, 47.46, 56.20, 110.36, 117.11, 119.64, 122.08, 125.26, 126.86, 127.33, 130.51, 132.78, 137.94, 150.67, 165.22, 171.49.

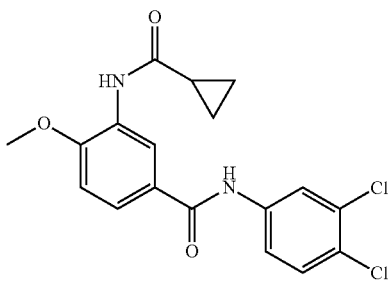 [SMILES: COc1ccc(C(=O)Nc2ccc(Cl)c(Cl)c2)cc1NC(=O)C1CC1]

3-(Cyclopropanecarboxamido)-N-(3,4-dichlorophenyl)-4-methoxy benzamide (21)

Prepared according to the general procedure using 3-amino-N-(3,4-dichlorophenyl)-4-methoxybenzamide 9 (20 mg, 0.064 mmol) and purified by flash column chromatography on silica gel (0-50% EtOAc in Hex) to afford 3-(cyclopropanecarboxamido)-N-(3,4-dichlorophenyl)-4-methoxybenzamide 21 (13 mg, 53%) as a white solid. MS (ESI): mass calcd. for $C_{18}H_{16}C_{12}N_2O_3$, 378.05; m/z found, 379.20 [M+H]+; $^1$H NMR (500 MHz, CDCl$_3$) δ 0.91-0.96 (m, 2H), 1.09-1.15 (m, 2H), 1.59-1.66 (m, 1H), 3.99 (s, 3H), 7.00 (d, J=8.54 Hz, 1H), 7.38 (d, J=8.85 Hz, 1H), 7.51 (dd, J=8.70, 2.59 Hz, 1H), 7.79 (dd, J=8.54, 2.14 Hz, 1H), 7.92 (d, J=2.44 Hz, 1H), 8.06 (brs, 1H), 8.31 (s, 1H) 8.80 (d, J=1.83 Hz, 1H); $^{13}$C NMR (126 MHz, CDCl$_3$) δ 8.61, 16.38, 56.30, 110.50, 117.21, 119.71, 122.13, 125.27, 126.99, 127.40, 127.57, 130.57, 132.84, 138.10, 150.64, 165.38, 172.70.

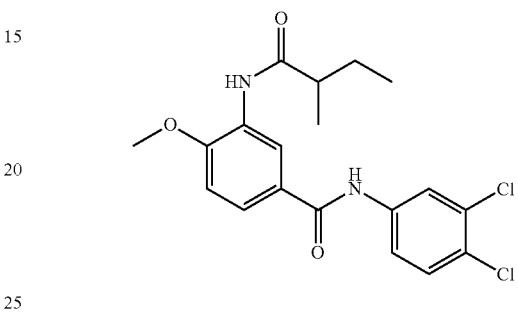

N-(3,4-dichlorophenyl)-4-methoxy-3-(2-methylbutanamido)benzamide (23)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-4-methoxy-3-(2-methylbutanamido)benzamide 23 (23 mg, 0.058 mmol, 45.3% yield) as a white solid. MS (ESI): mass calcd. for $C_{19}H_{20}C_{12}N_2O_3$, 394.09; m/z found, 395.0 [M+H]+; $^1$H NMR (500 MHz, CDCl$_3$) δ 0.94-1.01 (m, 3H), 1.26 (d, J=7.02 Hz, 3H), 1.56 (ddd, J=13.73, 7.48, 6.26 Hz, 1H), 1.78 (dt, J=13.73, 7.48 Hz, 1H), 2.31-2.39 (m, 1H), 3.98 (s, 3H), 7.00 (d, J=8.54 Hz, 1H), 7.39 (d, J=8.85 Hz, 1H), 7.51 (dd, J=8.85, 2.44 Hz, 1H), 7.80 (dd, J=8.54, 2.14 Hz, 1H), 7.86 (brs, 1H), 7.93 (d, J=2.44 Hz, 1H), 8.23 (s, 1H), 8.90 (d, J=2.44 Hz, 1H); $^{13}$C NMR (126 MHz, CDCl$_3$) δ 12.04, 17.66, 27.57, 44.66, 56.25, 110.39, 117, 119.64, 122.09, 125.29, 126.84, 127.43, 130.54, 132.83, 137.92, 150.74, 165.19, 175.62.

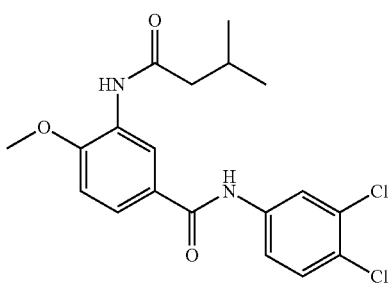

N-(3,4-dichlorophenyl)-4-methoxy-3-(3-methylbutanamido)benzamide (22)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in

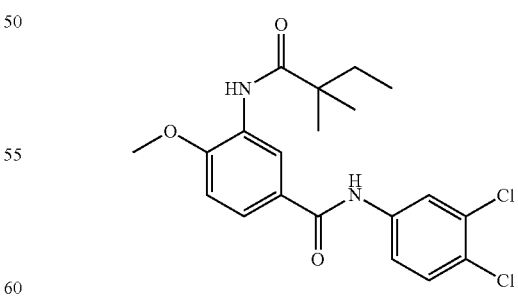

N-(3,4-dichlorophenyl)-3-(2,2-dimethylbutanamido)-4-methoxy benzamide (24)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-3-(2,2-dimethylbutanamido)-4-methoxybenzamide 24 (22 mg, 0.054 mmol, 41.8% yield) as a white solid. MS (ESI): mass calcd. for $C_{20}H_{22}C_{12}N_2O_3$, 408.10; m/z found, 409.06 [M+H]+; $^1$H NMR (500 MHz, CDCl$_3$) δ 0.93 (t, J=7.48 Hz, 3H), 1.30 (s, 6H), 1.64-1.71 (m, 2H), 3.98 (s, 3H), 7.00 (d, J=8.54 Hz, 1H), 7.39 (d, J=8.54 Hz, 1H), 7.50 (dd, J=8.70, 2.59 Hz, 1H), 7.80 (dd, J=8.70, 2.29 Hz, 1H), 7.93 (d, J=2.44 Hz, 1H), 8.21 (s, 1H), 8.90 (d, J=2.14 Hz, 1H); $^{13}$C NMR (126 MHz, CDCl$_3$) δ 9.39, 25.09, 34.19, 44.05, 56.38, 110.32, 116.83, 119.67, 122.11, 125.24, 126.83, 127.41, 127.50 130.52, 132.80, 137.91, 150.95, 165.23, 176.88.

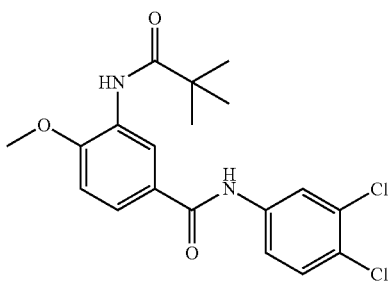

N-(3,4-dichlorophenyl)-4-methoxy-3-pivalamidobenzamide (25)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-4-methoxy-3-pivalamidobenzamide 25 (28 mg, 55.1%). MS (ESI): mass calcd. for $C_{19}H_{20}C_{12}N_2O_3$, 394.09; m/z found, 395.0 [M+H]+; $^1$H NMR (500 MHz, CDCl$_3$) d ppm 1.33-1.38 (m, 9H) 3.98 (s, 3H) 7.00 (d, J=8.54 Hz, 1H) 7.39 (d, J=8.85 Hz, 1H) 7.47-7.52 (m, 1H) 7.80 (dd, J=8.54, 2.44 Hz, 1H) 7.93 (d, J=2.75 Hz, 1H) 8.19 (br. s., 2H) 8.89 (d, J=2.44 Hz, 1H); $^{13}$C NMR (126 MHz, CDCl$_3$) d ppm 27.71 (s, 1C) 40.31 (s, 1C) 56.37 (s, 1C) 110.32 (s, 1C) 116.83 (s, 1C) 119.64 (s, 1C) 122.09 (s, 1C) 125.27 (s, 1C) 126.83 (s, 1C) 127.51 (s, 1C) 130.52 (s, 1C) 132.81 (s, 1C) 137.90 (s, 1C) 150.98 (s, 1C) 165.21 (s, 1C) 177.45 (s, 1C).

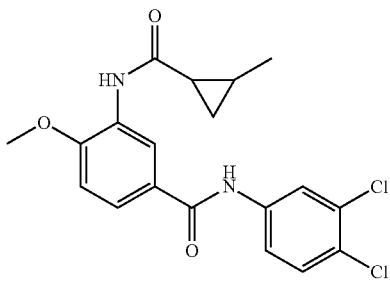 [SMILES: COc1ccc(C(=O)Nc2ccc(Cl)c(Cl)c2)cc1NC(=O)C1CC1C]

N-(3,4-dichlorophenyl)-4-methoxy-3-(2-methylcyclopropane carboxamido)benzamide (26)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-4-methoxy-3-(2-methylcyclopropanecarboxamido) benzamide 26 (22 mg, 0.056 mmol, 43.5% yield) as a white solid. MS (ESI): mass calcd. for $C_{19}H_{18}C_{12}N_2O_3$, 392.07; m/z found, 392.99 [M+H]+; $^1$H NMR (500 MHz, CDCl$_3$) d ppm 0.72-0.78 (m, 1H) 1.18 (d, J=6.10 Hz, 3H) 1.27-1.34 (m, 2H) 1.46-1.54 (m, 1H) 3.98 (s, 4H) 7.00 (d, J=8.54 Hz, 1H) 7.38 (d, J=8.54 Hz, 1H) 7.48 (dd, J=8.85, 2.44 Hz, 1H) 7.77 (dd, J=8.54, 2.14 Hz, 1H) 7.91 (d, J=2.75 Hz, 1H) 8.05 (s, 1H) 8.01 (s, 1H) 8.84 (d, J=2.14 Hz, 1H); $^{13}$C NMR (126 MHz, CDCl$_3$) d ppm 16.90 (s, 1C) 17.34 (s, 1C) 18.10 (s, 1C) 24.91 (s, 1C) 56.21 (s, 1C) 110.38 (s, 1C) 116.73 (s, 1C) 119.61 (s, 1C) 122.07 (s, 1C) 124.92 (s, 1C) 126.80 (s, 1C) 127.45 (s, 1C) 127.81 (s, 1C) 130.54 (s, 1C) 132.84 (s, 1C) 137.84 (s, 1C) 165.19 (s, 1C) 172.30 (s, 1C).

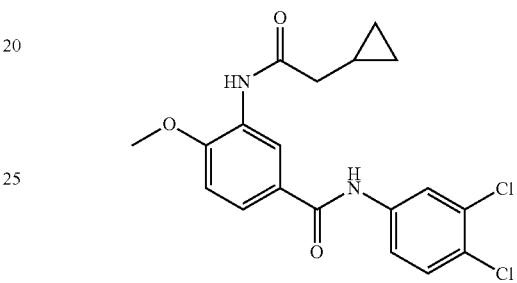

3-(2-Cyclopropylacetamido)-N-(3,4-dichlorophenyl)-4-methoxy benzamide (27)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(2-cyclopropylacetamido)-N-(3,4-dichlorophenyl)-4-methoxybenzamide 27 (35 mg, 69%) as a white solid. 1H NMR (500 MHz, CDCl$_3$) d ppm 0.28-0.40 (m, 2H) 0.69-0.81 (m, 2H) 1.11 (ddd, J=7.71, 4.81, 2.75 Hz, 1H) 2.39 (d, J=7.32 Hz, 2H) 3.98 (s, 3H) 7.01 (d, J=8.54 Hz, 1H) 7.40 (d, J=8.85 Hz, 1H) 7.48 (dd, J=8.85, 2.44 Hz, 1H) 7.80 (dd, J=8.54, 2.44 Hz, 1H) 7.93 (d, J=2.44 Hz, 1H) 8.06 (s, 1H) 8.42 (br. s., 1H) 8.90 (d, J=2.44 Hz, 1H); $^{13}$C NMR (126 MHz, CDCl$_3$) d ppm 4.86 7.35 42.94 56.33 110.37 116.85 119.60 122.08 125.17 126.84 127.59 130.57 132.88 137.84 150.77 165.16 171.32.

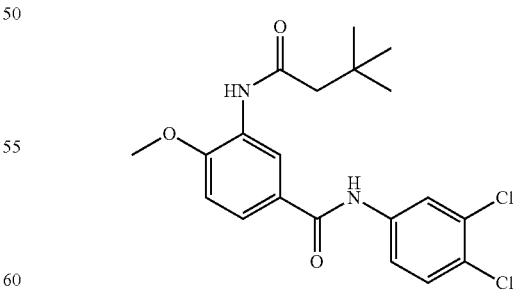

N-(3,4-dichlorophenyl)-3-(3,3-dimethylbutanamido)-4-methoxy benzamide (28)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-3-(3,3-dimethylbutanamido)-4-methoxybenzamide 28 (25 mg, 0.061 mmol, 47.5% yield) as a white solid. MS (ESI): mass calcd. for C20H22Cl2N2O3, 408.10; m/z found, 409.10 [M+H]+; $^1$H NMR (500 MHz, CDCl$_3$) d ppm 1.13 (s, 9H) 2.30 (s, 2H) 3.97 (s, 3H) 6.99 (d, J=8.54 Hz, 1H) 7.39 (d, J=8.54 Hz, 1H) 7.47-7.53 (m, 1H) 7.78 (dd, J=8.54, 2.44 Hz, 1H) 7.92 (d, J=2.44 Hz, 1H) 8.05 (s, 1H) 8.88 (d, J=2.44 Hz, 1H); $^{13}$C NMR (126 MHz, CDCl$_3$) d ppm 29.96 (s, 1C) 31.45 (s, 1C) 52.20 (s, 1C) 56.26 (s, 1C) 110.36 (s, 1C) 116.96 (s, 1C) 119.69 (s, 1C) 122.15 (s, 1C) 125.14 (s, 1C) 126.81 (s, 1C) 127.48 (s, 1C) 127.51 (s, 1C) 130.55 (s, 1C) 132.84 (s, 1C) 137.83 (s, 1C) 150.72 (s, 1C) 165.18 (s, 1C) 170.75 (s, 1C).

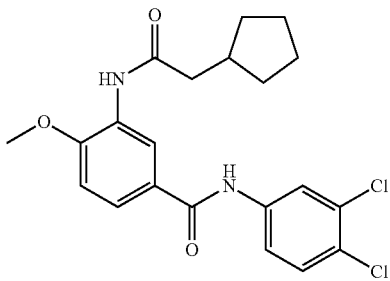 [SMILES: COc1ccc(C(=O)Nc2ccc(Cl)c(Cl)c2)cc1NC(=O)CC1CCCC1]

3-(2-Cyclopentylacetamido)-N-(3,4-dichlorophenyl)-4-methoxy benzamide (29)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(2-cyclopentylacetamido)-N-(3,4-dichlorophenyl)-4-methoxybenzamide 29 (31 mg, 57.2%) as a white solid. MS (ESI): mass calcd. for C21H22Cl2N2O3, 420.10; m/z found, 421.10 [M+H]+; $^1$H NMR (500 MHz, CDCl$_3$) d ppm 1.24 (td, J=7.71, 5.04 Hz, 2H) 1.56-1.64 (m, 4H) 1.87-1.95 (m, 2H) 2.30-2.39 (m, 1H) 2.43-2.48 (m, 2H) 3.97 (s, 3H) 6.99 (d, J=8.54 Hz, 1H) 7.39 (d, J=8.54 Hz, 1H) 7.51 (dd, J=8.70, 2.59 Hz, 1H) 7.77-7.84 (m, 2H) 7.94 (d, J=2.44 Hz, 1H) 8.24 (s, 1H) 8.85 (d, J=2.14 Hz, 1H); $^{13}$C NMR (126 MHz, CDCl$_3$) d ppm 25.14 (s, 1C) 32.74 (s, 1C) 37.24 (s, 1C) 44.41 (s, 1C) 56.21 (s, 1C) 110.34 (s, 1C) 117.14 (s, 1C) 119.68 (s, 1C) 122.11 (s, 1C) 125.27 (s, 1C) 126.87 (s, 1C) 127.35 (s, 1C) 130.49 (s, 1C) 132.76 (s, 1C) 137.97 (s, 1C) 150.67 (s, 1C) 165.25 (s, 1C) 171.81 (s, 1C).

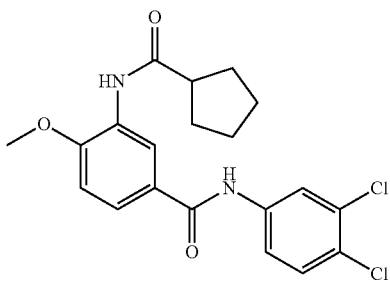 [SMILES: COc1ccc(C(=O)Nc2ccc(Cl)c(Cl)c2)cc1NC(=O)C1CCCC1]

3-(Cyclopentanecarboxamido)-N-(3,4-dichlorophenyl)-4-methoxy benzamide (30)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(cyclopentanecarboxamido)-N-(3,4-dichlorophenyl)-4-methoxybenzamide 30 (28 mg, 53.5%) as a white solid. MS (ESI): mass calcd. for C20H20Cl2N2O3, 406.09; m/z found, 407.10 [M+H]+; $^1$H NMR (500 MHz, CDCl$_3$) d ppm 1.61-1.69 (m, 2H) 1.77-1.87 (m, 2H) 1.90 (td, J=7.48, 4.88 Hz, 2H) 1.95-2.04 (m, 2H) 2.78 (t, J=8.09 Hz, 1H) 3.97 (s, 3H) 6.99 (d, J=8.54 Hz, 1H) 7.39 (d, J=8.54 Hz, 1H) 7.50 (dd, J=8.85, 2.44 Hz, 1H) 7.79 (dd, J=8.54, 2.44 Hz, 1H) 7.88 (br. s., 1H) 7.92 (d, J=2.44 Hz, 1H) 8.20 (s, 1H) 8.88 (d, J=2.44 Hz, 1H); $^{13}$C NMR (126 MHz, CDCl$_3$) d ppm 15.42 (s, 1C) 26.16 (s, 1C) 30.77 (s, 1C) 47.33 (s, 1° C.) 56.20 (s, 1C) 66.01 (s, 1C) 110.33 (s, 1C) 117.01 (s, 1C) 119.63 (s, 1C) 122.06 (s, 1C) 125.17 (s, 1C) 126.83 (s, 1C) 127.35 (s, 1C) 127.52 (s, 1C) 130.49 (s, 1C) 132.76 (s, 1C) 137.94 (s, 1C) 150.67 (s, 1C) 165.23 (s, 1C) 175.41 (s, 1C).

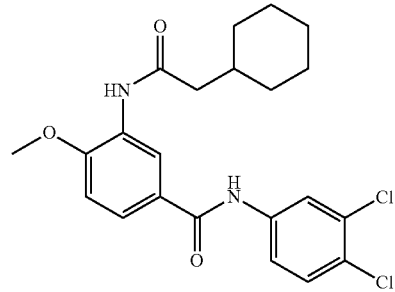 [SMILES: COc1ccc(C(=O)Nc2ccc(Cl)c(Cl)c2)cc1NC(=O)CC1CCCCC1]

3-(2-Cyclohexylacetamido)-N-(3,4-dichlorophenyl)-4-methoxy benzamide (31)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(2-cyclohexylacetamido)-N-(3,4-dichlorophenyl)-4-methoxybenzamide 31 (29 mg, 51.8%) as a white solid. MS (ESI): mass calcd. for C22H24Cl2N2O3, 434.12; m/z found, 435.0 [M+H]+; $^1$H NMR (500 MHz, CDCl$_3$) d ppm 1.04 (dd, J=11.90, 3.05 Hz, 2H) 1.17 (d, J=12.51 Hz, 1H) 1.23-1.38 (m, 3H) 1.72-1.77 (m, 2H) 1.82 (d, J=13.12 Hz, 2H) 1.89 (s, 1H) 2.30 (d, J=7.02 Hz, 2H) 3.97 (s, 3H) 6.99 (d, J=8.85 Hz, 1H) 7.39 (d, J=8.85 Hz, 1H) 7.48-7.51 (m, 1H) 7.79 (dd, J=8.54, 2.44 Hz, 2H) 7.93 (d, J=2.44 Hz, 1H) 8.26 (s, 1H) 8.86 (d, J=2.14 Hz, 1H); $^{13}$C NMR (126 MHz, CDCl$_3$) d ppm 26.04 (s, 1C) 26.14 (s, 1C) 33.12 (s, 1C) 35.49 (s, 1C) 46.11 (s, 1C) 56.06 (s, 1C) 76.74 (s, 1C) 77.25 (s, 1C) 110.22 (s, 1C) 116.85 (s, 1C) 119.48 (s, 1C) 121.94 (s, 1C) 125.09 (s, 1C) 126.69 (s, 1C) 127.21 (s, 1C) 127.25 (s, 1C) 130.37 (s, 1C) 132.65 (s, 1C) 137.78 (s, 1C) 150.48 (s, 1C) 165.05 (s, 1C) 171.31 (s, 1C).

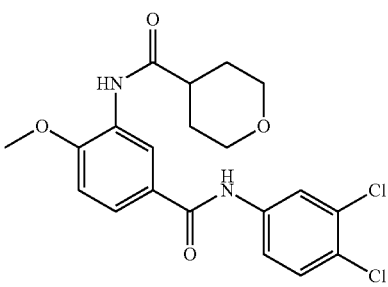 [SMILES: COc1ccc(C(=O)Nc2ccc(Cl)c(Cl)c2)cc1NC(=O)C1CCOCC1]

N-(5-((3,4-dichlorophenyl)carbamoyl)-2-methoxyphenyl)tetrahydro-2H-pyran-4-carboxamide (32)

Prepared according to the general procedure described in Step d using 3-amino-N-(3,4-dichlorophenyl)-4-methoxybenzamide 9 (20 mg, 0.064 mmol) and purified by flash column chromatography on silica gel (0-50% EtOAc in Hex) to afford N-(5-((3,4-dichlorophenyl)carbamoyl)-2-methoxyphenyl)tetrahydro-2H-pyran-4-carboxamide 32 (14 mg, 0.033 mmol, 51.5% yield). MS (ESI): mass calcd. for $C_{20}H_{20}Cl_2N_2O_4$, 422.08; m/z found, 423.24 [M+H]+. $^1$H NMR (500 MHz, CDCl$_3$) d ppm 1.89-1.99 (m, 4H) 2.62 (tt, J=11.06, 4.35 Hz, 1H) 3.50-3.56 (m, 2H) 4.01 (s, 3H) 4.09-4.15 (m, 2H) 7.04 (d, J=8.85 Hz, 1H) 7.43 (d, J=8.85 Hz, 1H) 7.53 (dd, J=8.85, 2.44 Hz, 1H) 7.84 (dd, J=8.70, 2.29 Hz, 1H) 7.91-7.98 (m, 2H) 8.14 (s, 1H) 8.90 (d, J=2.44 Hz, 1H); $^{13}$C NMR (126 MHz, CDCl$_3$) δ ppm 29.20 (s, 1C) 43.53 (s, 1C) 56.13 (s, 1C) 67.12 (s, 1C) 110.26 (s, 1C) 116.92 (s, 1C) 119.49 (s, 1C) 121.94 (s, 1C) 125.27 (s, 1C) 126.77 (s, 1C) 127.07 (s, 1C) 127.35 (s, 1C) 130.41 (s, 1C) 150.61 (s, 1C) 164.95 (s, 1C).

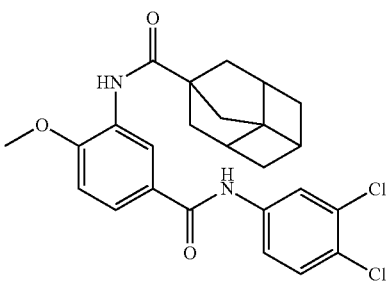 [SMILES: COc1ccc(C(=O)Nc2ccc(Cl)c(Cl)c2)cc1NC(=O)C12CC3CC4CC(C1)C43C2]

N-(5-((3,4-dichlorophenyl)carbamoyl)-2-methoxyphenyl)adamantane-2-carboxamide (33)

Prepared according to the general procedure described Step d in using 3-amino-N-(3,4-dichlorophenyl)-4-methoxybenzamide 9 (40 mg, 0.129 mmol) and purified by flash column chromatography on silica gel (0-50% EtOAc in Hex) to afford N-(5-((3,4-dichlorophenyl)carbamoyl)-2-methoxyphenyl)adamantane-2-carboxamide 33 (40 mg, 0.084 mmol, 65.7% yield). MS (ESI): mass calcd. for $C_{25}H_{26}Cl_2N_2O_3$, 472.13; m/z found, 473.12 [M+H]+. $^1$H NMR (500 MHz, CDCl$_3$) d ppm 1.77-1.85 (m, 6H) 1.98 (d, J=2.44 Hz, 6H) 2.13 (br. s., 3H) 3.99 (s, 3H) 6.99 (d, J=8.85 Hz, 1H) 7.38 (d, J=8.85 Hz, 1H) 7.50 (dd, J=8.70, 2.59 Hz, 1H) 7.80 (dd, J=8.70, 2.29 Hz, 1H) 7.93 (d, J=2.44 Hz, 1H) 8.16 (s, 1H) 8.21 (s, 1H) 8.92 (d, J=2.44 Hz, 1H); $^{13}$C NMR (126 MHz, CDCl$_3$) d ppm 28.24 (s, 1C) 36.54 (s, 1C) 39.37 (s, 1C) 42.19 (s, 1C) 56.36 (s, 1C) 110.30 (s, 1C) 116.95 (s, 1C) 119.63 (s, 1C) 122.07 (s, 1C) 125.23 (s, 1C) 126.80 (s, 1C) 127.36 (s, 1C) 127.48 (s, 1C) 130.51 (s, 1C) 132.79 (s, 1C) 137.94 (s, 1C) 151.03 (s, 1C) 165.23 (s, 1C) 176.95 (s, 1C).

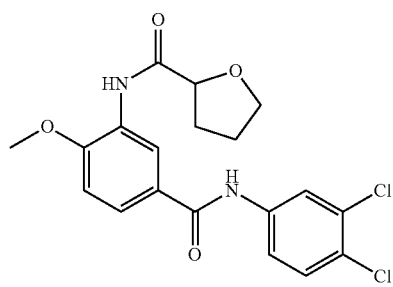 [SMILES: COc1ccc(C(=O)Nc2ccc(Cl)c(Cl)c2)cc1NC(=O)C1CCCO1]

N-(5-((3,4-dichlorophenyl)carbamoyl)-2-methoxyphenyl) tetrahydrofuran-2-carboxamide (34)

Prepared according to the general procedure described in Step d using 3-amino-N-(3,4-dichlorophenyl)-4-methoxybenzamide 9 (20 mg, 0.064 mmol) and purified by flash column chromatography on silica gel (0-50% EtOAc in Hex) to afford N-(5-((3,4-dichlorophenyl)carbamoyl)-2-methoxyphenyl)tetrahydrofuran-2-carboxamide 34 (11 mg, 0.027 mmol, 41.8% yield) as a white solid. MS (ESI): mass calcd. for $C_{19}H_{18}Cl_2N_2O_4$, 408.06; m/z found, 408.96 [M+H]+; $^1$H NMR (500 MHz, CDCl3) d ppm 1.89-2.04 (m, 2H) 2.18 (dd, J=13.43, 7.32 Hz, 1H) 2.38 (dd, J=12.82, 7.93 Hz, 1H) 3.98 (s, 3H) 3.99-4.02 (m, 1H) 4.04-4.13 (m, 1H) 4.50 (dd, J=8.39, 5.65 Hz, 1H) 7.00 (d, J=8.54 Hz, 1H) 7.39 (d, J=8.85 Hz, 1H) 7.50 (dd, J=8.70, 2.59 Hz, 1H) 7.80 (dd, J=8.54, 2.44 Hz, 1H) 7.92 (d, J=2.44 Hz, 1H) 8.10 (s, 1H) 8.88 (d, J=2.14 Hz, 1H) 9.15 (br. s., 1H); $^{13}$C NMR (126 MHz, CDCl$_3$) d ppm 25.71 (s, 1C) 30.43 (s, 1C) 56.29 (s, 1C) 69.93 (s, 1C) 78.94 (s, 1C) 110.50 (s, 1C) 116.96 (s, 1C) 119.60 (s, 1C) 122.06 (s, 1C) 125.55 (s, 1C) 126.73 (s, 1C) 126.79 (s, 1C) 127.46 (s, 1C) 130.56 (s, 1C) 132.85 (s, 1C) 137.87 (s, 1C) 151.33 (s, 1C) 165.14 (s, 1C) 172.15 (s, 1C).

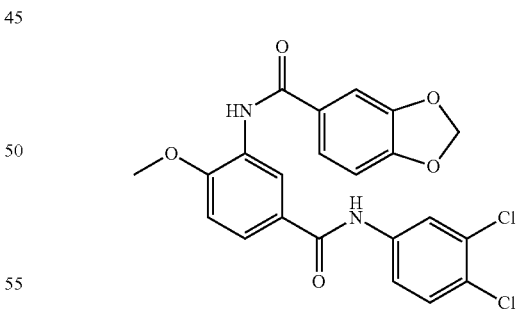

N-(5-((3,4-dichlorophenyl)carbamoyl)-2-methoxyphenyl)benzo[d][1,3]dioxole-5-carboxamide (35)

Prepared according to the general procedure described in Step d using 3-amino-N-(3,4-dichlorophenyl)-4-methoxybenzamide 9 (20 mg, 0.064 mmol) and purified by flash column chromatography on silica gel (0-50% EtOAc in Hex) to afford N-(5-((3,4-dichlorophenyl)carbamoyl)-2-methoxyphenyl)benzo[d][1,3]dioxole-5-carboxamide 35 (8 mg, 0.017 mmol, 27.1% yield). MS (ESI): mass calcd. for C22H16Cl2N2O5, 458.04; m/z found, 459.20 [M+H]+; $^1$H NMR (500 MHz, CDCl$_3$) d ppm 4.03 (s, 3H) 6.10 (s, 2H) 6.93 (d, J=8.85 Hz, 1H) 7.05 (d, J=8.54 Hz, 1H) 7.39-7.44 (m, 2H) 7.46 (dd, J=8.09, 1.98 Hz, 1H) 7.54 (dd, J=8.85, 2.44 Hz, 1H) 7.84 (dd, J=8.54, 2.44 Hz, 1H) 7.97 (d, J=2.44 Hz, 1H) 8.30 (s, 1H) 8.49 (s, 1H) 8.95 (d, J=2.14 Hz, 1H); $^{13}$C NMR (126 MHz, CDCl$_3$) d ppm 56.22 (s, 1C) 101.97 (s, 1C) 107.59 (s, 1C) 108.31 (s, 1C) 110.30 (s, 1C) 117.06 (s, 1C) 119.49 (s, 1C) 121.93 (s, 1C) 125.31 (s, 1C) 126.88 (s, 1C) 127.23 (s, 1C) 127.28 (s, 1C) 128.61 (s, 1C) 130.36 (s, 1C) 132.65 (s, 1C) 137.85 (s, 1C) 148.33 (s, 1C) 150.90 (s, 1C) 151.05 (s, 1C) 164.92 (s, 1C) 165.11 (s, 1C).

tography on silica gel (0-50% EtOAc in Hex) to afford 3-benzamido-N-(3,4-dichlorophenyl)-4-methoxybenzamide 37 as a white solid (13 mg, 49%). MS (ESI): mass calcd. for C21H16Cl2N2O3, 414.05; m/z found, 415.20 [M+H]+; $^1$H NMR (500 MHz, CDCl$_3$) d ppm 4.04 (s, 3H) 7.07 (d, J=8.85 Hz, 1H) 7.42 (d, J=8.85 Hz, 1H) 7.53-7.57 (m, 3H) 7.59-7.62 (m, 1H) 7.86 (dd, J=8.54, 2.44 Hz, 1H) 7.91-7.95 (m, 2H) 7.98 (d, J=2.44 Hz, 1H) 8.30 (s, 1H) 8.63 (s, 1H) 9.01 (d, J=2.44 Hz, 1H). $^{13}$C NMR (126 MHz, CDCl$_3$) d ppm 56.51 (s, 1C) 110.60 (s, 1C) 117.33 (s, 1C) 119.76 (s, 1C) 122.21 (s, 1C) 125.69 (s, 1C) 127.14 (s, 1C) 127.30 (s, 1C) 127.56 (s, 1C) 129.22 (s, 1C) 130.66 (s, 1C) 132.51 (s, 1C) 132.95 (s, 1C) 134.78 (s, 1C) 138.06 (s, 1C) 151.23 (s, 1C) 165.32 (s, 1C) 165.98 (s, 1C).

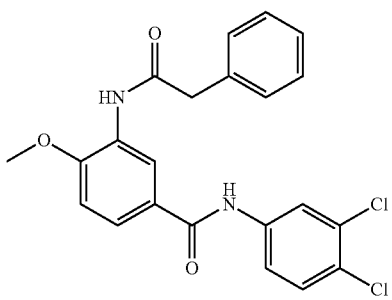 [SMILES: COc1ccc(C(=O)Nc2ccc(Cl)c(Cl)c2)cc1NC(=O)Cc1ccccc1]

N-(3,4-dichlorophenyl)-4-methoxy-3-(2-phenylacetamido)benzamide (36)

Prepared according to the general procedure using 3-amino-N-(3,4-dichlorophenyl)-4-methoxybenzamide 9 (20 mg, 0.064 mmol) and purified by flash column chromatography on silica gel (0-50% EtOAc in Hex) to afford N-(3,4-dichlorophenyl)-4-methoxy-3-(2-phenylacetamido) benzamideas 36 a white solid (6 mg, 22%). MS (ESI): mass calcd. for C22H18Cl2N2O3, 428.07; m/z found, 429.23 [M+H]+; $^1$H NMR (500 MHz, CDCl$_3$) d ppm 3.80 (s, 2H) 3.84 (s, 3H) 6.94 (d, J=8.85 Hz, 1H) 7.36-7.39 (m, 3H) 7.41-7.45 (m, 3H) 7.48 (dd, J=8.85, 2.44 Hz, 1H) 7.78 (dd, J=8.54, 2.14 Hz, 1H) 7.88 (br. s., 1H) 7.93 (d, J=2.44 Hz, 1H) 8.11 (s, 1H) 8.83 (d, J=2.44 Hz, 1H); $^{13}$C NMR (126 MHz, CDCl$_3$) d ppm 45.30, 56.26 110.47, 117.00, 119.71, 122.18, 125.59, 126.93, 127.27, 127.97 129.42, 129.79, 130.63, 132.92, 134.28, 138.00, 150.95, 165.24, 169.81.

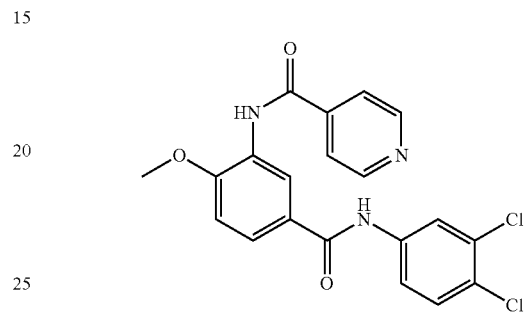

N-(5-((3,4-dichlorophenyl)carbamoyl)-2-methoxyphenyl) isonicotinamide (38)

Prepared according to the general procedure described in Step d using 3-amino-N-(3,4-dichlorophenyl)-4-methoxybenzamide 9 (20 mg, 0.064 mmol) and purified by flash column chromatography on silica gel (0-100% EtOAc in Hex) to afford N-(5-((3,4-dichlorophenyl)carbamoyl)-2-methoxyphenyl)isonicotinamide 38 (9 mg, 0.022 mmol, 33.6% yield). MS (ESI): mass calcd. for C20H15Cl2N3O3, 415.05; m/z found, 416.23 [M+H]+; $^1$H NMR (500 MHz, DMSO-d6) d ppm 3.92 (s, 3H) 7.28 (d, J=8.85 Hz, 1H) 7.61 (d, J=8.85 Hz, 1H) 7.78 (dd, J=8.85, 2.44 Hz, 1H) 7.88 (d, J=5.80 Hz, 2H) 7.93 (dd, J=8.70, 2.29 Hz, 1H) 8.16 (d, J=2.44 Hz, 1H) 8.30 (d, J=2.14 Hz, 1H) 8.76-8.83 (m, 2H) 10.03 (s, 1H) 10.40 (s, 1H); $^{13}$C NMR (126 MHz, DMSO-d6) d ppm 56.01 (s, 1C) 111.08 (s, 1C) 120.04 (s, 1C) 121.23 (s, 1C) 121.33 (s, 1C) 124.70 (s, 1C) 125.15 (s, 1C) 125.73 (s, 1C) 125.77 (s, 1C) 126.62 (s, 1C) 130.35 (s, 1C) 130.62 (s, 1C) 139.27 (s, 1C) 141.04 (s, 1C) 150.20 (s, 1C) 155.09 (s, 1C) 164.68 (s, 1C).

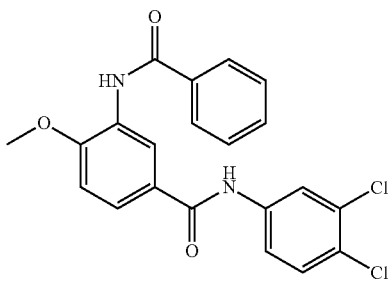 [SMILES: COc1ccc(C(=O)Nc2ccc(Cl)c(Cl)c2)cc1NC(=O)c1ccccc1]

3-Benzamido-N-(3,4-dichlorophenyl)-4-methoxybenzamide (37)

Prepared according to the general procedure using 3-amino-N-(3,4-dichlorophenyl)-4-methoxybenzamide 9 (20 mg, 0.064 mmol) and purified by flash column chroma-

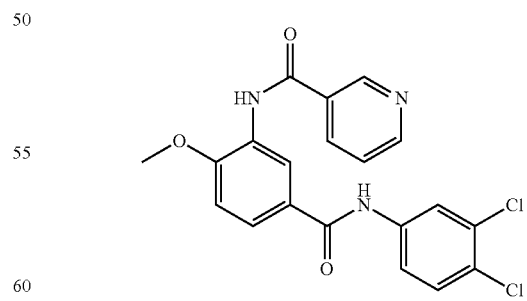

N-(5-((3,4-dichlorophenyl)carbamoyl)-2-methoxyphenyl)nicotinamide (39)

Prepared according to the general procedure described in Step d using 3-amino-N-(3,4-dichlorophenyl)-4-methoxybenzamide 9 (20 mg, 0.064 mmol) and purified by flash column chromatography on silica gel (0-100% EtOAc in Hex) to afford N-(5-((3,4-dichlorophenyl)carbamoyl)-2-methoxyphenyl)nicotinamide 39 (7.5 mg, 0.018 mmol, 28.0% yield). MS (ESI): mass calcd. for C20H15Cl2N3O3, 415.05; m/z found, 416.20 [M+H]+; $^1$H NMR (500 MHz, DMSO-d6) d ppm 3.93 (s, 3H) 7.27 (d, J=8.85 Hz, 1H) 7.56-7.59 (m, 1H) 7.61 (d, J=8.85 Hz, 1H) 7.78 (dd, J=8.85, 2.44 Hz, 1H) 7.92 (dd, J=8.54, 2.14 Hz, 1H) 8.16 (d, J=2.44 Hz, 1H) 8.30-8.35 (m, 2H) 8.78 (dd, J=4.73, 1.68 Hz, 1H) 9.13 (d, J=1.83 Hz, 1H) 9.97 (s, 1H) 10.40 (s, 1H); $^{13}$C NMR (126 MHz, DMSO-d6) d ppm 56.16 (s, 1C) 111.18 (s, 1C) 120.22 (s, 1C) 121.40 (s, 1C) 123.57 (s, 1C) 124.86 (s, 1C) 125.23 (s, 1° C.) 125.94 (s, 1C) 126.16 (s, 1C) 126.56 (s, 1C) 129.89 (s, 1C) 130.51 (s, 1C) 130.79 (s, 1° C.) 135.41 (s, 1C) 139.46 (s, 1C) 148.68 (s, 1C) 152.26 (s, 1C) 155.19 (s, 1C) 164.03 (s, 1° C.) 164.92 (s, 1C).

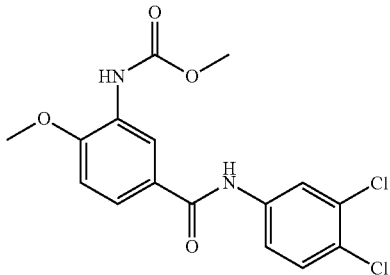 [SMILES: COC(=O)Nc1cc(C(=O)Nc2ccc(Cl)c(Cl)c2)ccc1OC]

Methyl (5-((3,4-dichlorophenyl)carbamoyl)-2-methoxyphenyl) carbamate (40)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford methyl (5-((3,4-dichlorophenyl)carbamoyl)-2-methoxyphenyl)carbamate 40 (23 mg, 48.5%) as a white solid. MS (ESI): mass calcd. for $C_{16}H_{14}C_{12}N_2O_4$, 368.03; m/z found, 369.0 [M+H]+; $^1$H NMR (500 MHz, CDCl3) d ppm 3.81-3.83 (m, 3H) 3.95 (s, 3H) 6.97 (d, J=8.54 Hz, 1H) 7.31 (br. s., 1H) 7.40 (d, J=8.85 Hz, 1H) 7.50 (dd, J=8.70, 2.59 Hz, 1H) 7.71 (dd, J=8.54, 2.14 Hz, 1H) 7.92 (d, J=2.44 Hz, 1H) 8.01 (br. s., 1H) 8.54 (br. s., 1H). $^{13}$C NMR (126 MHz, CDCl$_3$) δ ppm 52.72 (s, 1C) 56.19 (s, 1C) 110.36 (s, 1C) 119.59 (s, 1C) 122.04 (s, 1C) 126.96 (s, 1° C.) 127.51 (s, 1C) 127.63 (s, 1C) 130.60 (s, 1C) 131.16 (s, 1C) 132.89 (s, 1C) 137.84 (s, 1° C.) 147.43 (s, 1C) 150.56 (s, 1C) 165.24 (s, 1C).

Isopropyl (5-((3,4-dichlorophenyl)carbamoyl)-2-methoxyphenyl) carbamate (41)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford isopropyl (5-((3,4-dichlorophenyl)carbamoyl)-2-methoxyphenyl)carbamate 41 (17 mg, 33.3%) as a white solid. MS (ESI): mass calcd. for $C_{18}H_{18}C_{12}N_2O_4$, 396.06; m/z found, 397.0 [M+H]+; $^1$H NMR (500 MHz, CDCl$_3$) d ppm 1.31-1.37 (m, 6H) 3.95 (s, 3H) 4.99-5.10 (m, 1H) 6.97 (d, J=8.54 Hz, 1H) 7.25 (br. s., 1H) 7.40 (d, J=8.85 Hz, 1H) 7.50 (dd, J=8.85, 2.44 Hz, 1H) 7.71 (dd, J=8.54, 2.14 Hz, 1H) 7.91 (d, J=2.44 Hz, 1H) 8.02 (br. s., 1H) 8.56 (s, 1H). $^{13}$C NMR (126 MHz, CDCl$_3$) d ppm 22.24 (s, 1C) 56.14 (s, 1C) 69.38 (s, 1C) 110.31 (s, 1C) 119.61 (s, 1C) 122.05 (s, 1C) 123.95 (s, 1C) 126.92 (s, 1C) 127.46 (s, 1C) 127.81 (s, 1C) 130.57 (s, 1C) 132.86 (s, 1C) 137.89 (s, 1C) 150.51 (s, 1C) 153.44 (s, 1C) 165.31 (s, 1C).

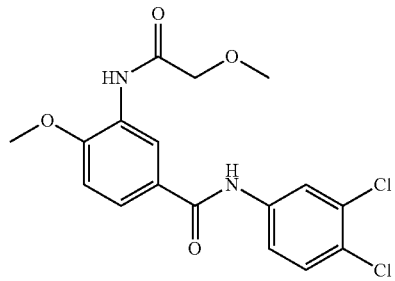 [SMILES: COCC(=O)Nc1cc(C(=O)Nc2ccc(Cl)c(Cl)c2)ccc1OC]

N-(3,4-dichlorophenyl)-4-methoxy-3-(2-methoxyacetamido)benzamide (42)

Prepared according to the general procedure described in Step d using 3-amino-N-(3,4-dichlorophenyl)-4-methoxybenzamide 9 (40 mg, 0.129 mmol) and purified by flash column chromatography on silica gel (0-50% EtOAc in Hex) to afford N-(3,4-dichlorophenyl)-4-methoxy-3-(2-methoxyacetamido)benzamide 42 (33 mg, 67.0%) as a white solid. MS (ESI): mass calcd. for $C_{17}H_{16}C_{12}N_2O_4$, 382.05; m/z found, 383.0 [M+H]+; $^1$H NMR (500 MHz, CDCl$_3$) d ppm 3.54 (s, 3H) 3.98 (s, 3H) 4.05 (s, 2H) 7.00 (d, J=8.54 Hz, 1H) 7.39 (d, J=8.54 Hz, 1H) 7.49 (dd, J=8.85, 2.44 Hz, 1H) 7.80 (dd, J=8.70, 2.29 Hz, 1H) 7.93 (d, J=2.75 Hz, 1H) 8.19 (s, 1H) 8.84 (d, J=2.14 Hz, 1H) 8.94 (br. s., 1H); $^{13}$C NMR (126 MHz, CDCl$_3$) d ppm 56.29 (s, 1C) 59.58 (s, 1C) 72.40 (s, 1C) 110.51 (s, 1C) 117.31 (s, 1C) 119.62 (s, 1C) 122.08 (s, 1C) 125.64 (s, 1C) 126.62 (s, 1C) 126.83 (s, 1C) 127.43 (s, 1C) 130.55 (s, 1C) 132.83 (s, 1C) 137.92 (s, 1C) 151.27 (s, 1C) 165.18 (s, 1C) 168.25 (s, 1C).

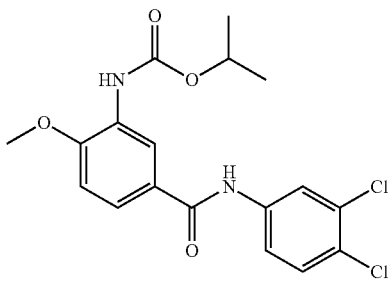

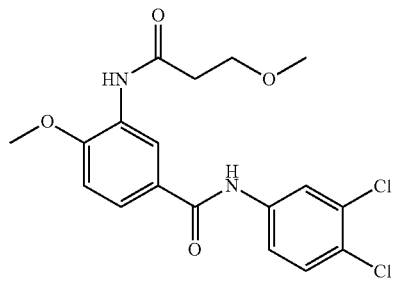 [SMILES: COCCC(=O)Nc1cc(C(=O)Nc2ccc(Cl)c(Cl)c2)ccc1OC]

N-(3,4-dichlorophenyl)-4-methoxy-3-(2-methoxyacetamido)benzamide (43)

Prepared according to the general procedure described in Step d using 3-amino-N-(3,4-dichlorophenyl)-4-methoxybenzamide 9 (20 mg, 0.064 mmol) and purified by flash column chromatography on silica gel (0-50% EtOAc in Hex) to afford N-(3,4-dichlorophenyl)-4-methoxy-3-(3-methoxypropanamido)benzamide 43 (8 mg, 31.3%) as a white solid. MS (ESI): mass calcd. for $C_{18}H_{18}C_{12}N_2O_4$, 396.06; m/z found, 397.0 [M+H]+; $^1$H NMR (500 MHz, CDCl$_3$) d ppm 2.63-2.71 (m, 2H) 3.47 (s, 3H) 3.70-3.76 (m, 2H) 3.96 (s, 3H) 6.97 (d, J=8.85 Hz, 1H) 7.38 (d, J=8.85 Hz, 1H) 7.48 (dd, J=8.70, 2.59 Hz, 1H) 7.77 (dd, J=8.70, 2.29 Hz, 1H) 7.92 (d, J=2.44 Hz, 1H) 8.15 (s, 1H) 8.87 (d, J=2.14 Hz, 1H) 8.91 (br. s., 1H); $^{13}$C NMR (126 MHz, CDCl$_3$) d ppm 38.37 (s, 1C) 56.23 (s, 1C) 59.09 (s, 1C) 68.49 (s, 1° C.) 110.32 (s, 1C) 117.17 (s, 1C) 119.59 (s, 1C) 122.05 (s, 1C) 125.09 (s, 1C) 126.77 (s, 1° C.) 127.37 (s, 1C) 127.71 (s, 1C) 130.52 (s, 1C) 132.80 (s, 1C) 137.92 (s, 1C) 150.90 (s, 1° C.) 165.27 (s, 1C) 170.43 (s, 1C).

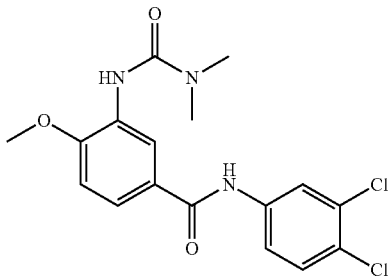 [SMILES: COc1ccc(C(=O)Nc2ccc(Cl)c(Cl)c2)cc1NC(=O)N(C)C]

N-(3,4-dichlorophenyl)-3-(3,3-dimethylureido)-4-methoxybenzamide (44)

Prepared according to the general procedure described in Step d using 3-amino-N-(3,4-dichlorophenyl)-4-methoxybenzamide 9 (30 mg, 0.096 mmol) and purified by flash column chromatography on silica gel (0-100% EtOAc in Hex) to afford N-(3,4-dichlorophenyl)-3-(3,3-dimethylureido)-4-methoxybenzamide 44 (21 mg, 57%) as a white solid. MS (ESI): mass calcd. for $C_{17}H_{17}C_{12}N_3O_3$, 381.06; m/z found, 382.01 [M+H]+; $^1$H NMR (500 MHz, DMSO-d6) d ppm 2.94 (s, 6H) 3.90 (s, 3H) 7.14 (d, J=8.54 Hz, 1H) 7.53 (s, 1H) 7.59 (d, J=8.85 Hz, 1H) 7.68 (dd, J=8.54, 2.44 Hz, 1H) 7.76 (dd, J=8.85, 2.44 Hz, 1H) 8.14 (d, J=2.44 Hz, 1H) 8.32 (d, J=2.44 Hz, 1H) 10.32 (s, 1H); $^{13}$C NMR (126 MHz, DMSO-d6) d ppm 36.03 (s, 1C) 56.14 (s, 1C) 110.22 (s, 1C) 120.14 (s, 1C) 121.31 (s, 1C) 121.52 (s, 1C) 123.26 (s, 1° C.) 124.70 (s, 1C) 126.12 (s, 1C) 128.67 (s, 1C) 130.48 (s, 1C) 130.76 (s, 1C) 139.57 (s, 1° C.) 152.75 (s, 1C) 155.28 (s, 1C) 165.45 (s, 1C)

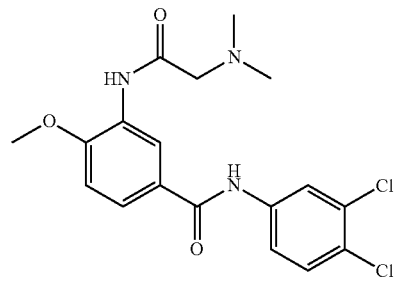 [SMILES: COc1ccc(C(=O)Nc2ccc(Cl)c(Cl)c2)cc1NC(=O)CN(C)C]

N-(3,4-dichlorophenyl)-3-(2-(dimethylamino)acetamido)-4-methoxy benzamide (45)

Prepared according to the general procedure described in Step d using 3-amino-N-(3,4-dichlorophenyl)-4-methoxybenzamide 9 (40 mg, 0.129 mmol) and purified by flash column chromatography on silica gel (0-10% MeOH in DCM) to afford N-(3,4-dichlorophenyl)-3-(2-(dimethylamino)acetamido)-4-methoxybenzamide 45 (25 mg, 49%) as a pale yellow solid. MS (ESI): mass calcd. for $C_{18}H_{19}C_{12}N_3O_3$, 395.08; m/z found, 396.01 [M+H]+; $^1$H NMR (500 MHz, CDCl$_3$) d ppm 2.44 (s, 6H) 3.16 (s, 2H) 4.01 (s, 3H) 7.04 (d, J=8.54 Hz, 1H) 7.43 (d, J=8.54 Hz, 1H) 7.52 (dd, J=8.54, 2.44 Hz, 1H) 7.83 (dd, J=8.54, 2.44 Hz, 1H) 7.97 (d, J=2.44 Hz, 1H) 8.08 (s, 1H) 8.89 (d, J=2.44 Hz, 1H) 9.72 (br. s., 1H); $^{13}$C NMR (126 MHz, CDCl$_3$) d ppm 46.23 (s, 1C) 56.30 (s, 1C) 64.12 (s, 1C) 110.54 (s, 1C) 117.12 (s, 1C) 119.58 (s, 1C) 122.07 (s, 1C) 125.33 (s, 1C) 126.73 (s, 1C) 127.20 (s, 1C) 130.59 (s, 1C) 132.89 (s, 1C) 137.88 (s, 1C) 165.19 (s, 1C) 169.62 (s, 1C)

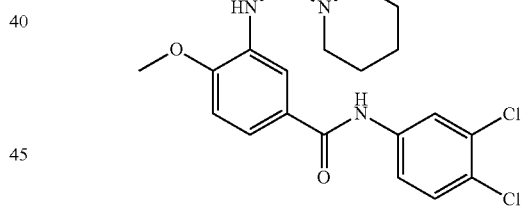

N-(5-((3,4-dichlorophenyl)carbamoyl)-2-methoxyphenyl)piperidine-1-carboxamide (46)

Prepared according to the general procedure described in Step d using 3-amino-N-(3,4-dichlorophenyl)-4-methoxybenzamide 9 (30 mg, 0.096 mmol) and purified by flash column chromatography on silica gel (0-50% EtOAc in Hex) to afford N-(5-((3,4-dichlorophenyl) carbamoyl)-2-methoxyphenyl)piperidine-1-carboxamide 46 (25 mg, 0.059 mmol, 61.4% yield). MS (ESI): mass calcd. for C20H21Cl2N3O3, 421.10; m/z found, 422.04 [M+H]+; $^1$H NMR (500 MHz, CDCl$_3$) d ppm 1.63-1.66 (m, 2H) 1.67 (br. s., 4H) 3.43-3.53 (m, 4H) 3.96 (s, 3H) 6.96 (d, J=8.54 Hz, 1H) 7.17 (s, 1H) 7.38 (d, J=8.54 Hz, 1H) 7.50 (dd, J=8.85, 2.44 Hz, 1H) 7.70 (dd, J=8.54, 2.44 Hz, 1H) 7.93 (d, J=2.44 Hz, 1H) 8.20 (s, 1H) 8.63 (d, J=2.14 Hz, 1H); $^{13}$C NMR (126 MHz, CDCl$_3$) d ppm 24.49 (s, 1C) 25.84 (s, 1C) 45.34 (s, 1C) 56.25 (s, 1C) 110.14 (s, 1C) 116.18 (s, 1C) 119.61 (s, 1C) 122.06 (s, 1C) 123.51 (s, 1C) 127.00 (s, 1C) 128.83 (s, 1C) 130.50 (s, 1C) 132.77 (s, 1C) 138.06 (s, 1C) 150.51 (s, 1C) 154.66 (s, 1C) 165.61 (s, 1C).

Step e: General Procedure for the Synthesis of Substituted Arylsulfonamides 47-50

A solution of 3-amino-N-(3,4-dichlorophenyl)-4-methoxybenzamide 9 (1 equiv) in pyridine (10 ml/mmol) was cooled to 0° C. and the appropriate sulfonyl chloride (1.5 equiv) was added to it dropwise. The reaction was allowed to warm to rt and stirred at that temperature for 12 h. DCM and 1N HCl were added and the layers separated. The organic layer was sequentially washed with 1N HCl, water, brine, dried over anhydrous Na2SO4 and evaporated under reduced pressure to give a crude solid that was purified by flash column chromatography on silica gel to yield the respective arylsulfonamides.

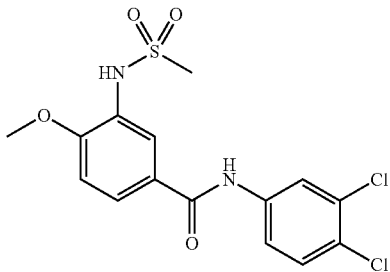 [SMILES: COc1ccc(C(=O)Nc2ccc(Cl)c(Cl)c2)cc1NS(C)(=O)=O]

47 N-(3,4-dichlorophenyl)-4-methoxy-3-(methylsulfonamido)benzamide (24 mg, 0.062 mmol, 48.0% yield): Prepared according to the general procedure using 3-amino-N-(3,4-dichlorophenyl)-4-methoxybenzamide (40 mg, 0.129 mmol) and purified by flash column chromatography on silica gel (0-50% EtOAc in Hex) to afford N-(3,4-dichlorophenyl)-4-methoxy-3-(methylsulfonamido)benzamide (24 mg, 0.062 mmol, 48.0% yield) as a white solid. MS (ESI): mass calcd. for $C_{15}H_{14}Cl_2N_2O_4S$, 388.01; m/z found, 388.90 [M+H]+; $^1H$ NMR (500 MHz, Acetone-d6) d ppm 2.99-3.03 (m, 3H) 4.00 (s, 3H) 7.22 (d, J=8.54 Hz, 1H) 7.53 (d, J=8.54 Hz, 1H) 7.77 (dd, J=8.85, 2.75 Hz, 1H) 7.88 (dd, J=8.70, 2.29 Hz, 1H) 7.95 (s, 1H) 8.07 (d, J=2.14 Hz, 1H) 8.22 (d, J=2.44 Hz, 1H) 9.74 (br. s., 1H); $^{13}C$ NMR (126 MHz, Acetone) d ppm 40.16 (s, 1C) 56.85 (s, 1C) 112.02 (s, 1C) 120.95 (s, 1C) 122.59 (s, 1C) 123.48 (s, 1C) 126.73 (s, 1C) 126.84 (s, 1C) 127.78 (s, 1C) 128.23 (s, 1C) 131.44 (s, 1C) 132.63 (s, 1C) 140.62 (s, 1C) 155.15 (s, 1C) 165.82 (s, 1C).

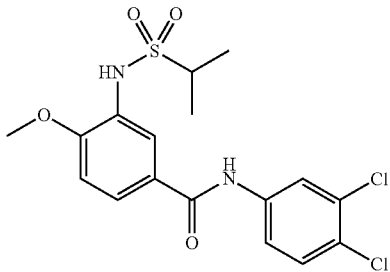 [SMILES: COc1ccc(C(=O)Nc2ccc(Cl)c(Cl)c2)cc1NS(=O)(=O)C(C)C]

N-(3,4-dichlorophenyl)-4-methoxy-3-(1-methylethylsulfonamido) benzamide (48)

Prepared according to the general procedure described in Step e using 3-amino-N-(3,4-dichlorophenyl)-4-methoxybenzamide 9 (40 mg, 0.129 mmol) and purified by flash column chromatography on silica gel (0-75% EtOAc in Hex) to N-(3,4-dichlorophenyl)-4-methoxy-3-(1-methylethylsulfonamido)benzamide 48 (6 mg, 0.014 mmol, 11.18% yield) as a white solid (6 mg, 11%). MS (ESI): mass calcd. for $C_{17}H_{18}Cl_2N_2O_4S$, 416.04; m/z found, 417.0 [M+H]+; $^1H$ NMR (500 MHz, Acetone-d6) d ppm 1.32 (s, 3H) 1.34 (s, 3H) 3.19-3.34 (m, 1H) 4.01 (s, 3H) 7.20 (d, J=8.54 Hz, 1H) 7.53 (d, J=8.85 Hz, 1H) 7.77 (dd, J=8.85, 2.44 Hz, 1H) 7.84 (dd, J=8.70, 2.29 Hz, 2H) 8.13 (d, J=2.14 Hz, 1H) 8.18-8.29 (m, 1H) 9.73 (br. s., 1H); $^{13}C$ NMR (126 MHz, Acetone) d ppm 16.91 (s, 1C) 53.68 (s, 1C) 56.83 (s, 1C) 111.87 (s, 1C) 120.96 (s, 1C) 122.59 (s, 1C) 122.73 (s, 1C) 126.20 (s, 1C) 126.73 (s, 1C) 128.26 (s, 1C) 131.45 (s, 1C) 132.65 (s, 1C) 140.65 (s, 1C) 165.93 (s, 1C).

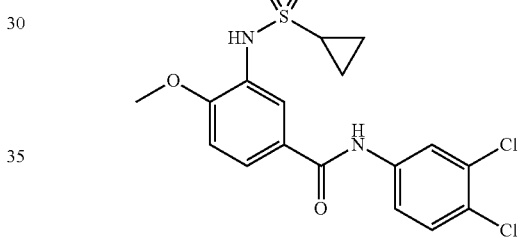

3-(cyclopropanesulfonamido)-N-(3,4-dichlorophenyl)-4-methoxy benzamide (49)

Prepared according to the general procedure described in Step e using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(cyclopropanesulfonamido)-N-(3,4-dichlorophenyl)-4-methoxybenzamide 49 (8 mg, 0.019 mmol, 14.99% yield) as a white solid. MS (ESI): mass calcd. for $C_{17}H_{16}Cl_2N_2O_4S$, 414.02; m/z found, 414.90 [M+H]+; $^1H$ NMR (500 MHz, Acetone-d6) d ppm 0.93-1.04 (m, 4H) 2.59-2.66 (m, 1H) 4.00 (s, 3H) 7.20 (d, J=8.54 Hz, 1H) 7.53 (d, J=8.54 Hz, 1H) 7.70-7.82 (m, 1H) 7.88 (dd, J=8.54, 2.14 Hz, 2H) 8.10 (d, J=2.14 Hz, 1H) 8.18-8.27 (m, 1H) 9.73 (br. s., 1H); $^{13}C$ NMR (126 MHz, Acetone) d ppm 5.74 (s, 1C) 5.79 (s, 1C) 30.81 (s, 1° C.) 56.86 (s, 1C) 111.85 (s, 1C) 120.96 (s, 1C) 122.60 (s, 1C) 123.83 (s, 1C) 126.73 (s, 1° C.) 126.78 (s, 1C) 127.92 (s, 1C) 128.09 (s, 1C) 131.44 (s, 1C) 132.65 (s, 1C) 140.65 (s, 1° C.) 155.49 (s, 1C) 165.83 (s, 1C).

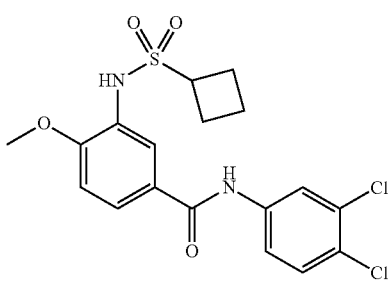 [SMILES: COc1ccc(C(=O)Nc2ccc(Cl)c(Cl)c2)cc1NS(=O)(=O)C1CCC1]

3-(cyclobutanesulfonamido)-N-(3,4-dichlorophenyl)-4-methoxy benzamide (50)

Prepared according to the general procedure described in Step e using 3-amino-N-(3,4-dichlorophenyl)-4-methoxybenzamide 9 (40 mg, 0.129 mmol) and purified by flash column chromatography on silica gel (0-50% EtOAc in Hex) to afford 3-(cyclobutanesulfonamido)-N-(3,4-dichlorophenyl)-4-methoxybenzamide 50 (10 mg, 0.023 mmol, 18.12% yield) as a white solid. MS (ESI): mass calcd. for $C_{18}H_{18}Cl_2N_2O_4S$, 428.04; m/z found, 429.0 [M+H]+; 1H NMR (500 MHz, Acetone-d6) d ppm 1.89-1.98 (m, 2H) 2.18-2.26 (m, 2H) 2.36-2.48 (m, 2H) 3.93 (t, J=8.24 Hz, 1H) 3.99 (s, 3H) 7.18 (d, J=8.85 Hz, 1H) 7.53 (d, J=8.85 Hz, 1H) 7.75-7.79 (m, 1H) 7.81 (br. s., 1H) 7.86 (dd, J=8.54, 2.44 Hz, 1H) 8.07 (d, J=2.44 Hz, 1H) 8.18-8.25 (m, 1H) 9.72 (br. s., 1H); $^{13}$C NMR (126 MHz, Acetone) d ppm 17.54 (s, 1C) 24.75 (s, 1C) 55.24 (s, 1C) 56.81 (s, 1C) 111.79 (s, 1C) 120.95 (s, 1C) 122.59 (s, 1C) 123.75 (s, 1C) 126.72 (s, 1C) 127.80 (s, 1C) 128.10 (s, 1C) 131.44 (s, 1C) 132.64 (s, 1C) 140.63 (s, 1C) 155.17 (s, 1C) 165.83 (s, 1C).

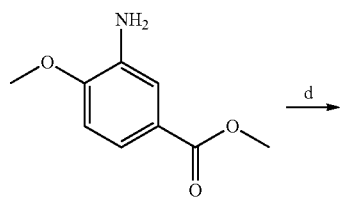

51

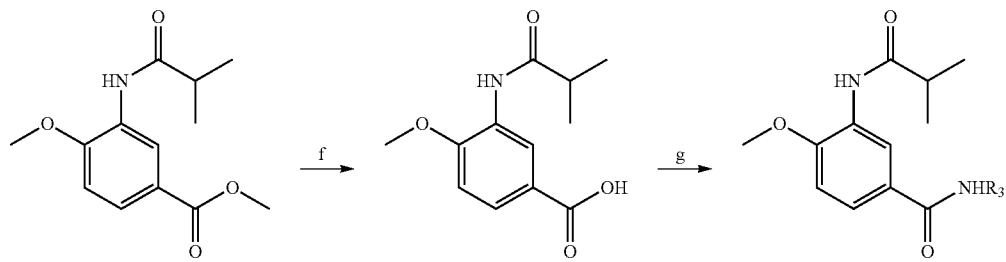

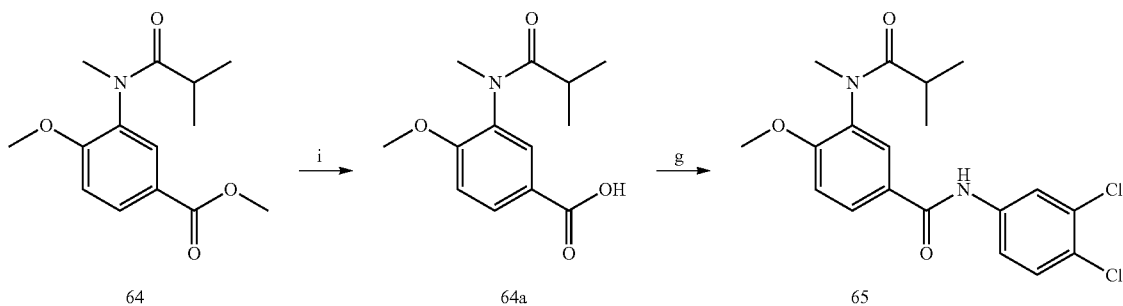

Scheme 2.

Reagents and conditions: (d) Isobutyryl chloride, TEA, DCM, 0° C. to rt, 2 h (f) LiOH, THF, H2O, rt, 12 h (g) EDCl, HOBt, R₃NH₂, DMF, 24 h, rt (h) NaH, CH₃I, THF, 0° C. to rt, 4 h (i) NaOH, MeOH, 60° C., 2 h.

Step d: Synthesis of methyl 3-isobutyramido-4-methoxybenzoate 52

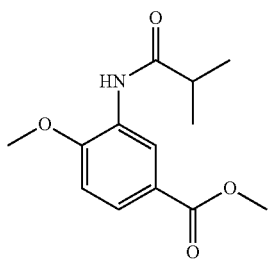

A solution of methyl 3-amino-4-methoxybenzoate 51 (1.5 g, 8.28 mmol) in DCM (40 ml) was cooled to 0° C. Isobutyryl chloride (0.962 ml, 9.11 mmol) was added to the solution gradually and the resulting suspension was warmed to rt and stirred at that temperature for 1 h upon which it became a clear solution. 1N HCl was added to the mixture and the layers separated. The organic layer was sequentially washed with 1N HCl, water, brine, then dried over anhydrous Na2SO4 and evaporated to give a crude solid which was triturated with diethyl ether to yield methyl 3-isobutyramido-4-methoxybenzoate 52 (1.75 g, 84%) as a white solid. MS (ESI): mass calcd. for $C_{13}H_{17}NO_4$, 251.12; m/z found, 252.03 [M+H]+; ¹H NMR (500 MHz, CDCl₃) d ppm 1.26 (s, 3H) 1.28 (s, 3H) 2.57 (t, J=7.02 Hz, 1H) 3.87 (s, 3H) 3.95 (s, 3H) 6.91 (d, J=8.54 Hz, 1H) 7.73-7.85 (m, 2H) 9.06 (d, J=1.83 Hz, 1H).

Step f: Synthesis of 3-isobutyramido-4-methoxybenzoic acid 52a

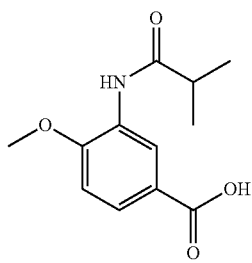 [SMILES: COc1ccc(C(=O)O)cc1NC(=O)C(C)C]

A solution of methyl 3-isobutyramido-4-methoxybenzoate 52 (1.3 g, 5.17 mmol) was dissolved in THF (10 ml). Water (10 ml) and LiOH (1.239 g, 51.7 mmol) were added and the reaction stirred at rt for 12 h. The organics were removed under reduced pressure and the remaining aqueous solution was washed with EtOAc. The aqueous extract was acidified with 1N HCl and the resulting solid was filtered and dried under high vacuum to afford 3-isobutyramido-4-methoxybenzoic acid 52a (0.82 g, 66.8% yield) as a white solid. MS (ESI): mass calcd. for $C_{12}H_{15}NO_4$ 237.10; m/z found, 238.00 [M+H]+; ¹H NMR (500 MHz, METHANOL-d4) d ppm 1.21 (s, 3H) 1.22 (s, 3H) 2.66-2.83 (m, 1H) 3.96 (s, 3H) 7.09 (d, J=8.85 Hz, 1H) 7.83 (dd, J=8.54, 2.14 Hz, 1H) 8.62 (d, J=2.14 Hz, 1H).

Step g: General Procedure for the Synthesis of Bisaryl Amides 53-63 and 65

EDCl (1.1 equiv) and HOBT (1.1 equiv) were added to a solution of 3-isobutyramido-4-methoxybenzoic acid 52a (1.0 equiv) in DMF (10 mL/mmol). The reaction mixture was stirred for 30 min at rt and then the appropriate amine R3NH2 (1.1 equiv) and DIPEA (2.0 equiv) were added to it. The resulting mixture was then stirred at rt for 24 h after which it was diluted with water and EtOAc. The layers were separated and the aqueous layer was further extracted with EtOAc (×3). The combined organic layer was dried using anhydrous Na2SO4 and evaporated under reduced pressure to give a residue which was subjected to flash column chromatography using silica gel to yield the respective products.

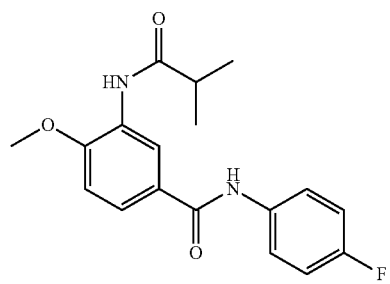 [SMILES: COc1ccc(C(=O)Nc2ccc(F)cc2)cc1NC(=O)C(C)C]

N-(4-fluorophenyl)-3-isobutyramido-4-methoxybenzamide (53)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-(4-fluorophenyl)-3-isobutyramido-4-methoxybenzamide 53 (33 mg, 0.100 mmol, 67.7% yield) as a white solid. MS (ESI): mass calcd. for $C_{18}H_{19}FN_2O_3$, 330.14; m/z found, 331.1 [M+H]+; ¹H NMR (500 MHz, CDCl3) d ppm 1.28 (s, 3H) 1.30 (s, 3H) 2.54-2.67 (m, 1H) 3.97 (s, 3H) 6.99 (d, J=8.54 Hz, 1H) 7.02-7.07 (m, 2H) 7.58-7.63 (m, 2H) 7.80 (dd, J=8.54, 2.14 Hz, 1H) 7.89 (br. s., 1H) 8.05 (br. s., 1H) 8.91 (d, J=2.14 Hz, 1H); ¹³C NMR (126 MHz, CDCl₃) d ppm 19.76 (s, 1C) 37.16 (s, 1C) 56.22 (s, 1C) 110.27 (s, 1C) 115.63 (s, 1C) 115.81 (s, 1C) 116.92 (s, 1C) 122.36 (s, 1C) 122.41 (s, 1C) 125.04 (s, 1C) 127.31 (s, 1C) 127.50 (s, 1C) 134.25 (s, 1C) 134.27 (s, 1C) 150.52 (s, 1C) 158.59 (s, 1C) 160.52 (s, 1C) 165.21 (s, 1C) 175.90 (s, 1C).

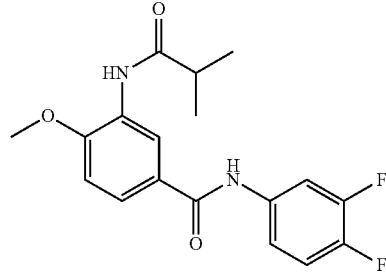 [SMILES: COc1ccc(C(=O)Nc2ccc(F)c(F)c2)cc1NC(=O)C(C)C]

N-(3,4-difluorophenyl)-3-isobutyramido-4-methoxybenzamide (54)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-(3,4-difluorophenyl)-3-isobutyramido-4-methoxybenzamide 54 (25 mg, 48.6% yield) as a white solid. MS (ESI): mass calcd. for $C_{18}H_{18}F_2N_2O_3$, 348.13; m/z found, 349.20 [M+H]+; $^1$H NMR (500 MHz, CDCl$_3$) d ppm 1.28 (s, 3H) 1.30 (s, 3H) 2.57-2.66 (m, 1H) 3.98 (s, 3H) 7.00 (d, J=8.54 Hz, 1H) 7.07-7.16 (m, 1H) 7.19-7.23 (m, 1H) 7.74-7.83 (m, 2H) 7.89 (br. s., 1H) 8.08 (br. s., 1H) 8.90 (d, J=2.14 Hz, 1H); $^{13}$C NMR (126 MHz, CDCl$_3$) d ppm 19.76, 37.17, 56.24, 110.19, 110.34, 110.36, 116.04, 116.08, 116.11, 116.87, 117.17, 117.31, 125.14, 126.94, 127.54, 134.85, 150.67, 165.18, 175.96.

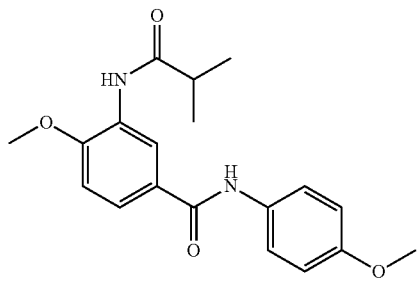

3-isobutyramido-4-methoxy-N-(4-methoxyphenyl)benzamide (55)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford 3-isobutyramido-4-methoxy-N-(4-methoxyphenyl)benzamide 55 (32 mg, 0.093 mmol, 63.4% yield) as a white solid. MS (ESI): mass calcd. for $C_{19}H_{22}N_2O_4$, 342.16; m/z found, 343.10 [M+H]+; $^1$H NMR (500 MHz, CDCl$_3$) d ppm 1.29 (s, 3H) 1.30 (s, 3H) 2.57-2.66 (m, 1H) 3.81 (s, 3H) 3.97 (s, 3H) 6.86-6.92 (m, 2H) 6.99 (d, J=8.54 Hz, 1H) 7.52-7.56 (m, 2H) 7.81 (dd, J=8.54, 2.44 Hz, 1H) 7.89 (br. s., 2H) 8.91 (d, J=2.14 Hz, 1H); $^{13}$C NMR (126 MHz, CDCl$_3$) d ppm 19.78 (s, 1C) 37.17 (s, 1C) 55.64 (s, 1C) 56.19 (s, 1C) 110.22 (s, 1C) 114.28 (s, 1C) 116.85 (s, 1C) 122.43 (s, 1C) 124.94 (s, 1C) 127.50 (s, 1C) 127.63 (s, 1C) 131.33 (s, 1C) 150.36 (s, 1C) 156.61 (s, 1C) 165.09 (s, 1C) 175.85 (s, 1C).

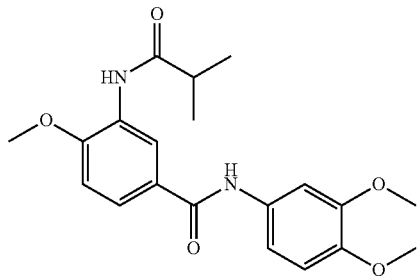

N-(3,4-dimethoxyphenyl)-3-isobutyramido-4-methoxybenzamide (56)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-(3,4-dimethoxyphenyl)-3-isobutyramido-4-methoxybenzamide 56 (34 mg, 0.091 mmol, 61.9% yield) as a light pink solid. MS (ESI): mass calcd. for C20H24N2O5, 372.17; m/z found, 373.20 [M+H]+; H NMR (500 MHz, CDCl$_3$) d ppm 1.29 (s, 3H) 1.30 (s, 3H) 2.58-2.65 (m, 1H) 3.88 (s, 3H) 3.92 (s, 3H) 3.98 (s, 3H) 6.84 (d, J=8.54 Hz, 1H) 7.00 (d, J=8.54 Hz, 1H) 7.06 (dd, J=8.54, 2.44 Hz, 1H) 7.43 (d, J=2.14 Hz, 1H) 7.82 (dd, J=8.70, 2.29 Hz, 1H) 7.86 (s, 1H) 7.90 (br. s., 1H) 8.93 (d, J=2.14 Hz, 1H); $^{13}$C NMR (126 MHz, CDCl$_3$) d ppm 19.78 (s, 1C) 37.17 (s, 1C) 56.10 (s, 1C) 56.20 (s, 1C) 56.25 (s, 1C) 105.42 (s, 1C) 110.27 (s, 1C) 111.41 (s, 1C) 112.57 (s, 1C) 116.76 (s, 1C) 124.98 (s, 1C) 127.48 (s, 1C) 127.53 (s, 1C) 131.86 (s, 1C) 146.00 (s, 1C) 149.13 (s, 1C) 150.41 (s, 1C) 165.06 (s, 1C) 175.89 (s, 1C).

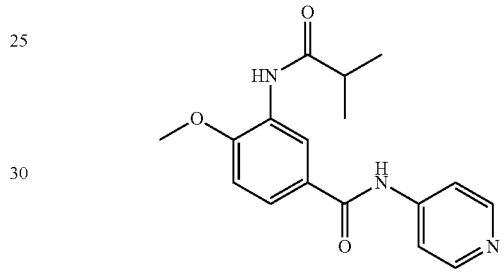

3-Isobutyramido-4-methoxy-N-(pyridin-4-yl)benzamide (57)

Prepared according to the general procedure described in Step g using 3-isobutyramido-4-methoxybenzoic acid 52a (0.035 g, 0.148 mmol) and purified by flash column chromatography on silica gel (0-100% EtOAc in Hex) to afford 3-isobutyramido-4-methoxybenzoic acid 57 (0.035 g, 0.148 mmol) as a white solid. MS (ESI): mass calcd. for $C_{17}H_{19}N_3O_3$, 313.14; m/z found, 314.10 [M+H]+; $^1$H NMR (500 MHz, CDCl$_3$) d ppm 1.29 (s, 3H) 1.30 (s, 3H) 2.56-2.68 (m, 1H) 3.99 (s, 3H) 7.02 (d, J=8.54 Hz, 1H) 7.73 (d, J=5.80 Hz, 2H) 7.82 (dd, J=8.54, 2.44 Hz, 1H) 7.90 (br. s., 1H) 8.54 (d, J=6.41 Hz, 3H) 8.90 (d, J=2.14 Hz, 1H); $^{13}$C NMR (126 MHz, CDCl$_3$) d ppm 19.75 (s, 1C) 37.17 (s, 1C) 56.31 (s, 1° C.) 110.48 (s, 1C) 114.25 (s, 1C) 117.32 (s, 1C) 125.59 (s, 1C) 126.46 (s, 1C) 127.46 (s, 1° C.) 151.13 (s, 1C) 165.77 (s, 1C) 176.08 (s, 1C).

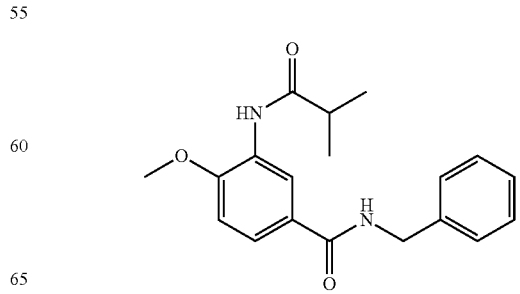

N-benzyl-3-isobutyramido-4-methoxybenzamide (58)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-benzyl-3-isobutyramido-4-methoxybenzamide 58 (35 mg, 0.107 mmol, 72.7% yield) as a white solid. MS (ESI): mass calcd. for $C_{19}H_{22}N_2O_3$, 326.16; m/z found, 327.10 [M+H]+; $^1$H NMR (500 MHz, CDCl$_3$) d ppm 1.25 (s, 3H) 1.27 (s, 3H) 2.57 (dt, J=13.73, 6.87 Hz, 1H) 3.95 (s, 3H) 4.62 (d, J=5.80 Hz, 2H) 6.55 (br. s., 1H) 6.95 (d, J=8.85 Hz, 1H) 7.30-7.37 (m, 4H) 7.78 (dd, J=8.54, 2.14 Hz, 1H) 7.84 (br. s., 1H) 8.79 (d, J=2.14 Hz, 1H); $^{13}$C NMR (126 MHz, CDCl$_3$) d ppm 19.75 (s, 1C) 37.12 (s, 1C) 44.22 (s, 1° C.) 56.14 (s, 1C) 110.00 (s, 1C) 116.82 (s, 1C) 124.75 (s, 1C) 127.03 (s, 1C) 127.47 (s, 1C) 127.58 (s, 1C) 128.10 (s, 1C) 128.83 (s, 1C) 138.51 (s, 1C) 150.22 (s, 1C) 166.78 (s, 1C) 175.72 (s, 1C).

3-isobutyramido-4-methoxy-N-(4-methoxybenzyl)benzamide (60)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford 3-isobutyramido-4-methoxy-N-(4 methoxybenzyl)benzamide 60 (33 mg, 0.093 mmol, 62.8% yield) as a white solid. MS (ESI): mass calcd. for $C_{20}H_{24}N_2O_4$, 356.17; m/z found, 357.10 [M+H]+; $^1$H NMR (500 MHz, CDCl$_3$) d ppm 1.25 (s, 3H) 1.26 (s, 3H) 2.53-2.63 (m, 1H) 3.79 (s, 3H) 3.94 (s, 3H) 4.55 (d, J=5.49 Hz, 2H) 6.45 (br. s., 1H) 6.84-6.88 (m, 2H) 6.94 (d, J=8.54 Hz, 1H) 7.27-7.28 (m, 1H) 7.76 (dd, J=8.70, 2.29 Hz, 1H) 7.84 (br. s., 1H) 8.77 (d, J=2.44 Hz, 1H); $^{13}$C NMR (126 MHz, CDCl$_3$) d ppm 19.75 (s, 1C) 37.11 (s, 1C) 43.71 (s, 1C) 55.46 (s, 1C) 56.14 (s, 1C) 109.98 (s, 1C) 114.24 (s, 1C) 116.80 (s, 1C) 124.71 (s, 1C) 127.11 (s, 1C) 127.45 (s, 1C) 129.48 (s, 1C) 130.63 (s, 1C) 150.18 (s, 1C) 159.13 (s, 1C) 166.69 (s, 1C) 175.70 (s, 1C).

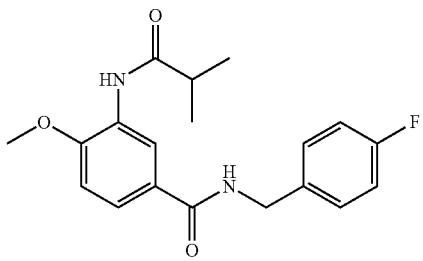 [SMILES: COc1ccc(C(=O)NCc2ccc(F)cc2)cc1NC(=O)C(C)C]

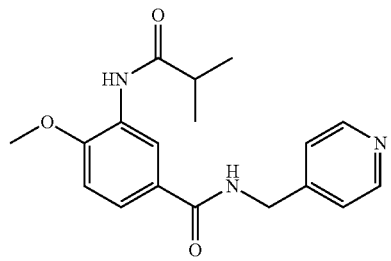

N-(4-fluorobenzyl)-3-isobutyramido-4-methoxybenzamide (59)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-(4-fluorobenzyl)-3-isobutyramido-4-methoxybenzamide 59 (25 mg, 0.073 mmol, 49.2% yield). MS (ESI): mass calcd. for $C_{19}H_{21}FN_2O_3$, 344.15; m/z found, 345.10 [M+H]+; $^1$H NMR (500 MHz, CDCl$_3$) δ ppm 1.25 (s, 3H) 1.27 (s, 3H) 2.57 (quin, J=6.87 Hz, 1H) 3.95 (s, 3H) 4.58 (d, J=5.80 Hz, 2H) 6.60 (br. s., 1H) 6.95 (d, J=8.54 Hz, 1H) 6.98-7.03 (m, 2H) 7.29-7.34 (m, 2H) 7.77 (dd, J=8.54, 2.14 Hz, 1H) 7.85 (br. s., 1H) 8.79 (d, J=2.14 Hz, 1H); $^{13}$C NMR (126 MHz, CDCl$_3$) d ppm 19.75 (s, 1C) 37.12 (s, 1C) 43.44 (s, 1C) 56.16 (s, 1C) 110.04 (s, 1C) 115.54 (s, 1C) 115.71 (s, 1C) 116.76 (s, 1C) 124.80 (s, 1C) 126.85 (s, 1C) 127.47 (s, 1C) 129.71 (s, 1C) 129.78 (s, 1C) 134.38 (s, 1C) 150.28 (s, 1C) 161.34 (s, 1C) 163.29 (s, 1C) 166.78 (s, 1C) 175.79 (s, 1C).

3-isobutyramido-4-methoxy-N-(pyridin-4-ylmethyl)benzamide (61)

Prepared according to the general procedure described in Step g using 3-isobutyramido-4-methoxybenzoic acid 52a (0.035 g, 0.148 mmol) and purified by flash column chromatography on silica gel (0-100% EtOAc in Hex) to afford 3-isobutyramido-4-methoxy-N-(pyridin-4-ylmethyl)benzamide 61 (30 mg, 0.092 mmol, 62.1% yield) as a white solid. MS (ESI): mass calcd. for $C_{18}H_{21}N_3O_3$, 327.16; m/z found, 328.15 [M+H]+; $^1$H NMR (500 MHz, CDCl$_3$) d ppm 1.26 (s, 3H) 1.28 (s, 3H) 2.59 (quin, J=6.87 Hz, 1H) 3.96 (s, 3H) 4.63 (d, J=6.10 Hz, 2H) 6.69-6.78 (m, 1H) 6.97 (d, J=8.54 Hz, 1H) 7.23-7.26 (m, 2H) 7.79 (dd, J=8.70, 2.29 Hz, 1H) 7.87 (br. s., 1H) 8.49-8.61 (m, 2H) 8.86 (d, J=2.14 Hz, 1H); $^{13}$C NMR (126 MHz, CDCl$_3$) d ppm 19.75 (s, 1C) 37.13 (s, 1C) 42.92 (s, 1C) 56.19 (s, 1C) 77.36 (s, 1C) 110.13 (s, 1C) 116.74 (s, 1C) 122.49 (s, 1C) 124.90 (s, 1C) 126.38 (s, 1C) 127.58 (s, 1C) 147.68 (s, 1C) 150.18 (s, 1C) 150.46 (s, 1C) 167.03 (s, 1C) 175.87 (s, 1C).

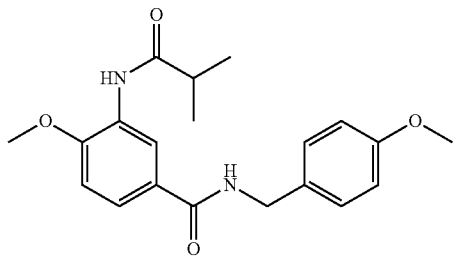

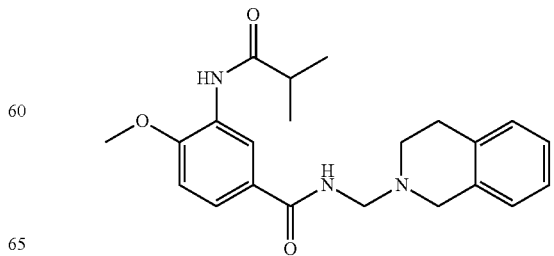

N-(2-methoxy-5-(1,2,3,4-tetrahydroisoquinoline-2-carbonyl)phenyl) isobutyramide (62)

Prepared according to the general procedure described in Step g using 3-isobutyramido-4-methoxybenzoic acid 52a (0.035 g, 0.148 mmol) and purified by flash column chromatography on silica gel (0-50% EtOAc in Hex) to afford N-(2-methoxy-5-(1,2,3,4-tetrahydroisoquinoline-2-carbonyl)phenyl)isobutyramide 62 (22 mg, 0.062 mmol, 42.3% yield) as a white solid. MS (ESI): mass calcd. for $C_{21}H_{24}N_2O_3$, 352.18; m/z found, 704.90 [2M+H]+; $^1$H NMR (500 MHz, CDCl$_3$) d ppm 1.26 (s, 3H) 1.28 (s, 3H) 2.58 (quin, J=6.87 Hz, 1H) 2.95 (t, J=5.80 Hz, 2H) 3.68-3.91 (m, 2H) 3.93 (s, 3H) 4.71 (br. s., 1H) 4.84 (br. s., 1H) 6.93 (d, J=8.24 Hz, 1H) 7.12-7.22 (m, 4H) 7.81 (br. s., 1H) 8.56 (br. s., 1H); $^{13}$C NMR (126 MHz, CDCl$_3$) d ppm 19.79 (s, 1C) 37.13 (s, 1C) 56.09 (s, 1C) 110.05 (s, 1C) 118.86 (s, 1C) 123.66 (s, 1C) 126.60 (s, 1C) 127.32 (s, 1C) 128.86 (s, 1C) 133.37 (s, 1C) 149.06 (s, 1C) 175.32 (s, 1C).

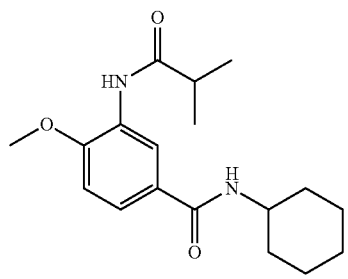 [SMILES: COc1ccc(C(=O)NC2CCCCC2)cc1NC(=O)C(C)C]

N-cyclohexyl-3-isobutyramido-4-methoxybenzamide (63)

Prepared according to the general procedure using described in Step g using 3-isobutyramido-4-methoxybenzoic acid 52a (0.035 g, 0.148 mmol) and purified by flash column chromatography on silica gel (0-50% EtOAc in Hex) to afford N-cyclohexyl-3-isobutyramido-4-methoxybenzamide 63 (30 mg, 0.094 mmol, 63.9% yield) as a white solid. MS (ESI): mass calcd. for $C_{18}H_{26}N_2O_3$, 318.19; m/z found, 319.26 [M+H]+; $^1$H NMR (500 MHz, CDCl$_3$) d ppm 1.20-1.24 (m, 2H) 1.27 (s, 3H) 1.29 (s, 3H) 1.36-1.44 (m, 2H) 1.62-1.68 (m, 2H) 1.75 (dt, J=13.89, 3.43 Hz, 2H) 1.98-2.03 (m, 2H) 2.58 (quin, J=6.87 Hz, 1H) 3.94 (s, 3H) 3.95-3.99 (m, 1H) 6.04 (d, J=7.63 Hz, 1H) 6.93 (d, J=8.85 Hz, 1H) 7.72 (dd, J=8.54, 2.14 Hz, 1H) 7.86 (br. s., 1H) 8.73 (d, J=2.44 Hz, 1H); $^{13}$C NMR (126 MHz, CDCl$_3$) d ppm 19.78 (s, 1C) 25.26 (s, 1C) 25.76 (s, 1C) 33.42 (s, 1C) 37.15 (s, 1C) 48.95 (s, 1C) 56.12 (s, 1C) 109.94 (s, 1C) 116.65 (s, 1C) 124.62 (s, 1C) 127.37 (s, 1C) 127.73 (s, 1C) 150.00 (s, 1C) 166.04 (s, 1C) 175.76 (s, 1C).

Step h: Synthesis of methyl 4-methoxy-3-(N-methylisobutyramido)benzoate 64

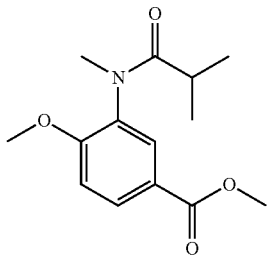

To a cooled (0° C.) solution of methyl 3-isobutyramido-4-methoxybenzoate 52 (1.128 g, 4.49 mmol) and CH3I (0.421 ml, 6.73 mmol) in THF (20 ml) was added NaH (0.269 g, 6.73 mmol) cautiously. The mixture was warmed to rt and with stirred at for 12 h. The reaction mixture was then diluted with EtOAc followed by the addition of water. The organic solvents were evaporated under reduced pressure and the residue was partitioned between EtOAc and water. The organic layer was washed with brine, dried over anhydrous Na2SO4 and evaporated to give the desired product methyl 4-methoxy-3-(N-methylisobutyramido)benzoate 64 (MS (ESI): mass calcd. for $C_{14}H_{19}NO_4$, 265.13; m/z found, 266.33 [M+H]+) along with a small amount of the corresponding acid 64a. The mixture was taken to the next step directly without further purification.

Step i: General Procedure for the Synthesis of Substituted Benzoic Acids 64a, 66a, 67a and 68a To a mixture of the substituted methylbenzoate (1.0 equiv) in MeOH (3 mL/mmol) was added a solution of 2M NaOH (1 ml/mmol). The resulting mixture was heated to 60° C. and stirred at that temperature for 1 h. The reaction was then cooled and MeOH was evaporated under reduced pressure. The aqueous layer was washed with diethyl ether and acidified to pH~5-6 using 1N HCl. The resulting precipitate was filtered and dried under high vacuum to give the corresponding acids.

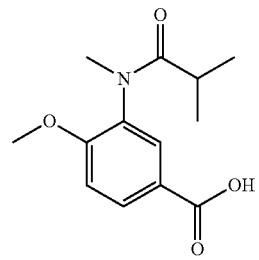 [SMILES: COc1ccc(C(=O)O)cc1N(C)C(=O)C(C)C]

4-Methoxy-3-(N-methylisobutyramido)benzoic acid (64a)

Prepared according to the general procedure described in Step i using a mixture of methyl 4-methoxy-3-(N-methylisobutyramido)benzoate 64 (0.750 g, 2.83 mmol) and 4-methoxy-3-(N-methylisobutyramido)benzoic acid 64a (0.213 g, 0.848 mmol) to afford 4-methoxy-3-(N-methylisobutyramido)benzoic acid 64a (0.54 g, 76%) as a white solid. MS (ESI): mass calcd. for $C_{13}H_{17}NO_4$, 251.12; m/z found, 251.99 [M+H]+; $^1$H NMR (500 MHz, CDCl$_3$) d ppm 1.00 (d, J=6.71 Hz, 3H) 1.03 (d, J=6.71 Hz, 3H) 2.28-2.41 (m, 1H) 3.18 (s, 3H) 3.92 (s, 3H) 7.04 (d, J=8.85 Hz, 1H) 7.93 (d, J=2.14 Hz, 1H) 8.12 (dd, J=8.85, 2.14 Hz, 1H).

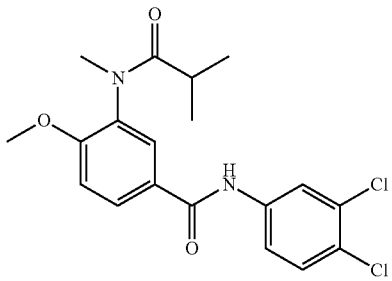 [SMILES: COc1ccc(C(=O)Nc2ccc(Cl)c(Cl)c2)cc1N(C)C(=O)C(C)C]

N-(3,4-dichlorophenyl)-4-methoxy-3-(N-methyl-isobutyramido) benzamide (65)

Prepared according to the general procedure described in Step g using 4-methoxy-3-(N-methylisobutyramido)benzoic acid 64a (520 mg, 2.069 mmol) and purified by flash column chromatography on silica gel (0-50% EtOAc in Hex) to afford N-(3,4-dichlorophenyl)-4-methoxy-3-(N-methyl-isobutyramido)benzamide 65 (400 mg, 48.9% yield) as a white solid. MS (ESI): mass calcd. for $C_{19}H_{20}C_{12}N_2O_3$, 394.09; m/z found, 395.40 [M+H]+; $^1$H NMR (500 MHz, Acetone) d ppm 0.91 (d, J=6.71 Hz, 3H) 0.93 (d, J=6.71 Hz, 3H) 2.30-2.41 (m, 1H) 3.10 (s, 3H) 3.98 (s, 3H) 7.30 (d, J=8.54 Hz, 1H) 7.53 (d, J=8.85 Hz, 1H) 7.74 (dd, J=8.85, 2.44 Hz, 1H) 7.99 (d, J=2.14 Hz, 1H) 8.08 (dd, J=8.70, 2.29 Hz, 1H) 8.18 (d, J=2.44 Hz, 1H) 9.66 (br. s., 1H). $^{13}$C NMR (126 MHz, Acetone) d ppm 19.75 (s, 1C) 20.42 (s, 1C) 31.82 (s, 1C) 36.24 (s, 1C) 56.72 (s, 1C) 113.13 (s, 1C) 120.86 (s, 1C) 120.94 (s, 1C) 122.51 (s, 1C) 122.60 (s, 1C) 129.78 (s, 1C) 130.22 (s, 1C) 131.49 (s, 1C) 132.68 (s, 1C) 133.85 (s, 1C) 140.48 (s, 1C) 159.52 (s, 1C) 165.28 (s, 1C) 177.44 (s, 1C).

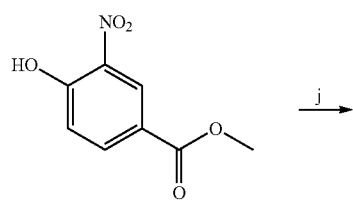

66

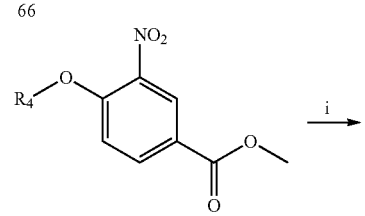

67, 68, 69

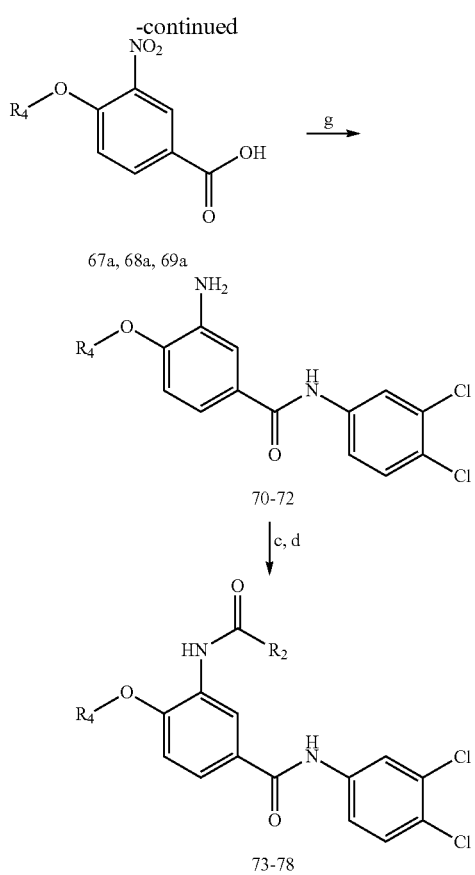

67a, 68a, 69a 70-72

73-78

Scheme 3.
Reagents and conditions: (j) R$_4$—Cl/R$_4$—Br, KI, K$_2$CO$_3$, DMF, 80° C., 12 h; (i) NaOH, MeOH, 60° C., 2 h; (g) EDCl, HOBt, 3,4-dichloroaniline, DCM, 12 h, rt; (c) SnCl$_2$.2H2O, EtOH, 78° C., 2 h; (d) R$_2$COCl, TEA, DCM, 0° C. to rt, 2 h.

Step j: General Procedure for the Synthesis of 4-Alkyl-3-Nitrobenzoates 67-69

A mixture of methyl 4-hydroxy-3-nitrobenzoate (1.0 equiv), K$_2$CO$_3$ (1.5 equiv) and alkyl halide R$_4$—I or R$_4$—Cl or R$_4$—Br, (1.5 equiv) in DMF (1.5 mL/mmol) was stirred at 75° C. for 12 h (catalytic amount of KI was added when using R4-Cl as the alkylating agent). The reaction was cooled and H$_2$O was added to the mixture. The precipitated solid was filtered and washed with cold H$_2$O then dried to give the respective 4-alkyl-3-nitrobenzoates.

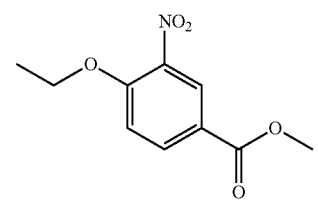 [SMILES: CCOc1ccc(C(=O)OC)cc1[N+](=O)[O-]]

Methyl 4-ethoxy-3-nitrobenzoate (67)

Prepared according to the general procedure described in Step j using methyl 4-hydroxy-3-nitrobenzoate 66 (0.300 g, 1.522 mmol) and ethyl iodide (0.184 ml, 2.283 mmol) to afford methyl 4-ethoxy-3-nitrobenzoate 67 (220 mg, 0.977 mmol, 64.2% yield) as a pale yellow solid. MS (ESI): mass calcd. for $C_{10}H_{11}NO_5$, 225.06; m/z found, 267.0 [M+ACN+H]+; $^1$H NMR (500 MHz, CDCl$_3$) d ppm 1.50 (t, J=7.02 Hz, 3H) 3.93 (s, 3H) 4.25 (q, J=7.02 Hz, 2H) 7.10 (d, J=8.85 Hz, 1H) 8.18 (dd, J=8.70, 2.29 Hz, 1H) 8.48 (d, J=2.14 Hz, 1H).

(166 mg, 0.786 mmol, 80% yield) as a white solid. MS (ESI): mass calcd. for C9H9NO5, 211.05; m/z found, 212.20 [M+H]+; $^1$H NMR (500 MHz, METHANOL-d4) d ppm 1.46 (t, J=7.02 Hz, 3H) 4.30 (q, J=7.02 Hz, 2H) 7.34 (d, J=8.85 Hz, 1H) 8.21 (dd, J=8.70, 2.29 Hz, 1H) 8.37 (d, J=2.14 Hz, 1H).

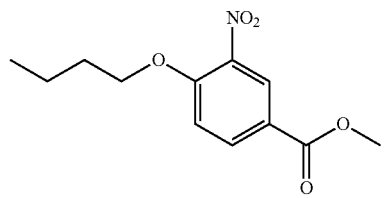 [SMILES: CCCCOc1ccc(C(=O)OC)cc1[N+](=O)[O-]]

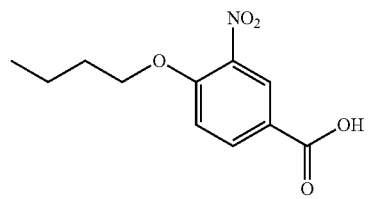

4-Butoxy-3-nitrobenzoic acid (68a)

Methyl 4-butoxy-3-nitrobenzoate (68): Prepared according to the general procedure described in Step j using methyl 4-hydroxy-3-nitrobenzoate 66 (0.300 g, 1.522 mmol) and 1-bromobutane (0.245 ml, 2.283 mmol) to afford methyl 4-butoxy-3-nitrobenzoate 68 (260 mg, 1.027 mmol, 67.5% yield) as a white solid. MS (ESI): mass calcd. for $C_{12}H_{15}NO_5$, 253.10; m/z found, 295.02 [M+ACN+H]+; $^1$H NMR (500 MHz, CDCl$_3$) d ppm 0.98 (t, J=7.32 Hz, 3H) 1.47-1.56 (m, 2H) 1.80-1.88 (m, 2H) 3.92 (s, 3H) 4.17 (t, J=6.41 Hz, 2H) 7.10 (d, J=8.85 Hz, 1H) 8.18 (dd, J=8.85, 2.14 Hz, 1H) 8.48 (d, J=2.14 Hz, 1H).

Prepared according to the general procedure described in using methyl 4-butoxy-3-nitrobenzoate 68 (200 mg, 0.790 mmol) to afford 4-butoxy-3-nitrobenzoic acid 68a (100 mg, 0.418 mmol, 52.9% yield) as a white solid. MS (ESI): mass calcd. for $C_{11}H_{13}NO_5$, 239.08; m/z found, 240.20 [M+H]+; $^1$H NMR (500 MHz, METHANOL-d4) d ppm 1.00 (t, J=7.32 Hz, 3H) 1.49-1.61 (m, 2H) 1.78-1.87 (m, 2H) 4.24 (t, J=6.26 Hz, 2H) 7.35 (d, J=8.85 Hz, 1H) 8.21 (dd, J=8.85, 2.14 Hz, 1H) 8.38 (d, J=2.14 Hz, 1H).

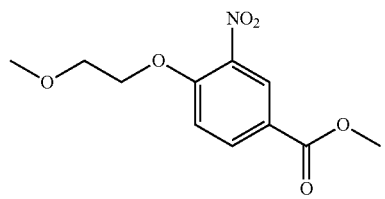

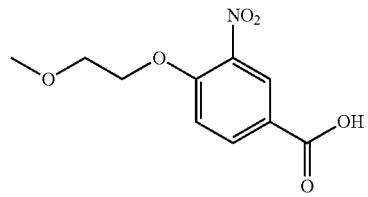

4-(2-Methoxyethoxy)-3-nitrobenzoic acid (69a)

Methyl 4-(2-methoxyethoxy)-3-nitrobenzoate (69): Prepared according to the general procedure described in Step j using methyl 4-hydroxy-3-nitrobenzoate 66 (0.300 g, 1.522 mmol) and 1-chloro-2-methoxyethane (0.208 ml, 2.283 mmol) to afford methyl 4-(2-methoxyethoxy)-3-nitrobenzoate 69 (280 mg, 1.097 mmol, 72.1% yield) as a white solid. MS (ESI): mass calcd. for $Cl_1H_{13}NO_6$, 255.07; m/z found, 255.95 [M+H]+; $^1$H NMR (500 MHz, CDCl$_3$) d ppm 3.45 (s, 3H) 3.78-3.84 (m, 2H) 3.92 (s, 3H) 4.28-4.35 (m, 2H) 7.15 (d, J=8.85 Hz, 1H) 8.19 (dd, J=8.70, 2.29 Hz, 1H) 8.49 (d, J=2.14 Hz, 1H).

Prepared according to the general procedure described in Step i using methyl 4-(2-methoxyethoxy)-3-nitrobenzoate 69 (280 mg, 1.097 mmol) to afford 4-(2-methoxyethoxy)-3-nitrobenzoic acid 69a (180 mg, 0.746 mmol, 68.0% yield) as a white solid. MS (ESI): mass calcd. for $C_{10}H_{11}NO_6$, 241.06; m/z found, 242.23 [M+H]+; $^1$H NMR (500 MHz, METHANOL-d4) d ppm 3.43 (s, 3H) 3.77-3.85 (m, 2H) 4.31-4.40 (m, 2H) 7.39 (d, J=8.85 Hz, 1H) 8.22 (dd, J=8.85, 2.14 Hz, 1H) 8.39 (d, J=2.14 Hz, 1H).

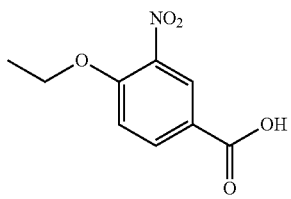

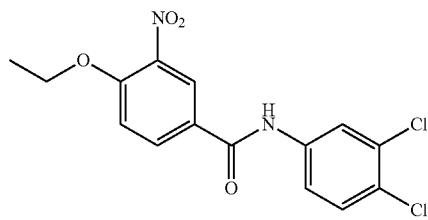 [SMILES: CCOc1ccc(C(=O)Nc2ccc(Cl)c(Cl)c2)cc1[N+](=O)[O-]]

4-Ethoxy-3-nitrobenzoic acid (67a)

N-(3,4-dichlorophenyl)-4-ethoxy-3-nitrobenzamide (70)

Prepared according to the general procedure described in Step i using methyl 4-ethoxy-3-nitrobenzoate 67 (220 mg, 0.977 mmol) to afford 4-ethoxy-3-nitrobenzoic acid 67a Prepared according to the general procedure described in Step g using 4-ethoxy-3-nitrobenzoic acid 68a (160 mg, 0.758 mmol) to afford N-(3,4-dichlorophenyl)-4-ethoxy-3-nitrobenzamide 70 (126 mg, 0.355 mmol, 46.8% yield) as a white solid. MS (ESI): mass calcd. for $C_{15}H_{12}C_{12}N_2O_4$, 354.02; m/z found, 355.20 [M+H]+; $^1$H NMR (500 MHz, CDCl$_3$) d ppm 1.51-1.54 (m, 3H) 4.28 (q, J=7.02 Hz, 2H) 7.19 (d, J=8.85 Hz, 1H) 7.41-7.49 (m, 2H) 7.78 (s, 1H) 7.90 (d, J=2.14 Hz, 1H) 8.11 (dd, J=8.85, 2.44 Hz, 1H) 8.32 (d, J=2.14 Hz, 1H).

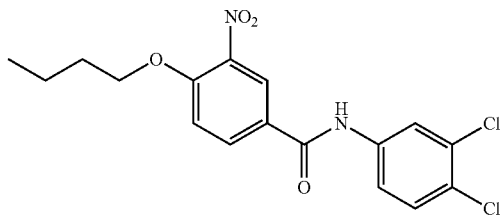 [SMILES: CCCCOc1ccc(C(=O)Nc2ccc(Cl)c(Cl)c2)cc1[N+](=O)[O-]]

4-butoxy-N-(3,4-dichlorophenyl)-3-nitrobenzamide (71)

Prepared according to the general procedure described in Step g using 4-butoxy-3-nitrobenzoic acid 68a (95 mg, 0.397 mmol) to afford 4-butoxy-N-(3,4-dichlorophenyl)-3-nitrobenzamide 71 (78 mg, 0.204 mmol, 51.3% yield) as a white solid. MS (ESI): mass calcd. for $C_{17}H_{16}C_{12}N_2O_4$, 382.05; m/z found, 383.14 [M+H]+; $^1$H NMR (500 MHz, CDCl$_3$) d ppm 1.00 (t, J=7.48 Hz, 3H) 1.52-1.55 (m, 2H) 1.86 (dd, J=8.39, 6.87 Hz, 2H) 4.20 (t, J=6.41 Hz, 2H) 7.19 (d, J=8.85 Hz, 1H) 7.41-7.50 (m, 2H) 7.83 (s, 1H) 7.90 (d, J=2.14 Hz, 1H) 8.10 (dd, J=8.85, 2.44 Hz, 1H) 8.32 (d, J=2.44 Hz, 1H).

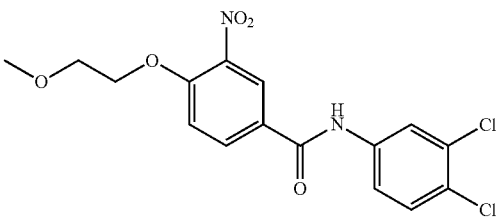 [SMILES: COCCOc1ccc(C(=O)Nc2ccc(Cl)c(Cl)c2)cc1[N+](=O)[O-]]

N-(3,4-dichlorophenyl)-4-(2-methoxyethoxy)-3-nitrobenzamide (72)

Prepared according to the general procedure described in Step g using 4-(2-methoxyethoxy)-3-nitrobenzoic acid 69a (153 mg, 0.634 mmol) to afford N-(3,4-dichlorophenyl)-4-(2-methoxyethoxy)-3-nitrobenzamide 72 (120 mg, 0.312 mmol, 49.1% yield) as a white solid. MS (ESI): mass calcd. for $C_{16}H_{14}C_{12}N_2O_5$, 384.03; m/z found, 385.30 [M+H]+; $^1$H NMR (500 MHz, CDCl$_3$) d ppm 3.46 (s, 3H) 3.79-3.88 (m, 2H) 4.30-4.42 (m, 2H) 7.24 (s, 1H) 7.39-7.51 (m, 2H) 7.80 (br. s., 1H) 7.90 (d, J=2.14 Hz, 1H) 8.11 (dd, J=8.85, 2.44 Hz, 1H) 8.34 (d, J=2.44 Hz, 1H).

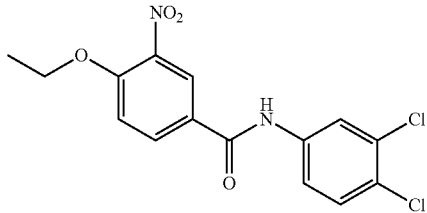 [SMILES: CCOc1ccc(C(=O)Nc2ccc(Cl)c(Cl)c2)cc1[N+](=O)[O-]]

3-amino-N-(3,4-dichlorophenyl)-4-ethoxybenzamide (70a)

Prepared according to the general procedure described in Step c using N-(3,4-dichlorophenyl)-4-ethoxy-3-nitrobenzamide 70 (120 mg, 0.338 mmol) to afford 3-amino-N-(3,4-dichlorophenyl)-4-ethoxybenzamide 70a (60 mg, 0.185 mmol, 54.6% yield) as an off-white solid. MS (ESI): mass calcd. for $C_{15}H_{14}C_{12}N_2O_2$, 324.04; m/z found, 365.96 [M+ACN+H]+; $^1$H NMR (500 MHz, CDCl$_3$) d ppm 1.47-1.50 (m, 3H) 3.98 (br. s., 1H) 4.14 (q, J=7.12 Hz, 2H) 6.81 (d, J=8.24 Hz, 1H) 7.17 (d, J=8.24 Hz, 1H) 7.24 (s, 1H) 7.38-7.42 (m, 1H) 7.43-7.47 (m, 1H) 7.68 (br. s., 1H) 7.87 (s, 1H).

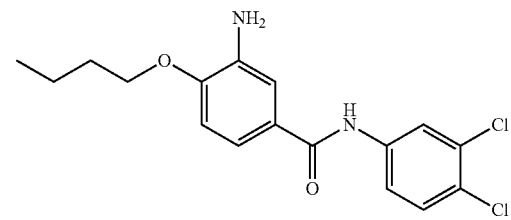

3-amino-4-butoxy-N-(3,4-dichlorophenyl)benzamide (71a)

Prepared according to the general procedure described in Step c using 4-butoxy-N-(3,4-dichlorophenyl)-3-nitrobenzamide 71 (75 mg, 0.196 mmol) to afford 3-amino-4-butoxy-N-(3,4-dichlorophenyl)benzamide 71a (45 mg, 0.127 mmol, 65.1% yield) as an light brown solid. MS (ESI): mass calcd. for $C_{17}H_{18}C_{12}N_2O_2$, 352.07; m/z found, 394.00 [M+ACN+H]+; $^1$H NMR (500 MHz, CDCl$_3$) d ppm 1.00 (t, J=7.48 Hz, 3H) 1.48-1.54 (m, 2H) 1.79-1.88 (m, 2H) 3.97 (br. s., 2H) 4.07 (t, J=6.41 Hz, 2H) 6.81 (d, J=8.54 Hz, 1H) 7.17 (dd, J=8.54, 2.14 Hz, 1H) 7.24 (d, J=1.83 Hz, 1H) 7.40 (d, J=8.54 Hz, 1H) 7.45 (dd, J=8.54, 2.44 Hz, 1H) 7.68 (s, 1H) 7.87 (d, J=2.44 Hz, 1H).

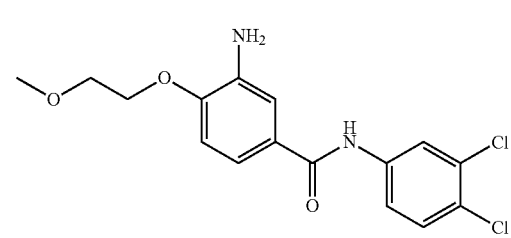

3-amino-N-(3,4-dichlorophenyl)-4-(2-methoxyethoxy)benzamide (72a)

Prepared according to the general procedure described in Step c using N-(3,4-dichlorophenyl)-4-(2-methoxyethoxy)-3-nitrobenzamide 72 (116 mg, 0.301 mmol) to afford 3-amino-N-(3,4-dichlorophenyl)-4-(2-methoxyethoxy)benzamide 72a (65 mg, 0.183 mmol, 60.8% yield) as an off-white solid. MS (ESI): mass calcd. for $C_{16}H_{16}C_{12}N_2O_3$, 354.05; m/z found, 355.00 [M+H]+; $^1$H NMR (500 MHz, CDCl$_3$) d ppm 3.44-3.47 (m, 3H) 3.76-3.82 (m, 2H) 4.02 (br. s., 2H) 4.19-4.24 (m, 2H) 6.84 (d, J=8.24 Hz, 1H) 7.16 (dd, J=8.24, 1.53 Hz, 1H) 7.23 (s, 1H) 7.40 (d, J=8.54 Hz, 1H) 7.45 (dd, J=8.54, 1.83 Hz, 1H) 7.70 (s, 1H) 7.87 (d, J=1.83 Hz, 1H).

3-(cyclobutanecarboxamido)-N-(3,4-dichlorophenyl)-4-ethoxy benzamide (73)

Prepared according to the general procedure described in Step d using 3-amino-N-(3,4-dichlorophenyl)-4-ethoxybenzamide 70a (20 mg, 0.062 mmol) and purified by flash column chromatography on silica gel (0-50% EtOAc in Hex) to afford 3-(cyclobutanecarboxamido)-N-(3,4-dichlorophenyl)-4-ethoxybenzamide 73 (10 mg, 0.025 mmol, 39.9% yield) as a white solid. MS (ESI): mass calcd. for C20H20Cl2N2O3, 406.09; m/z found, 407.0 [M+H]+; $^1$H NMR (500 MHz, CDCl$_3$) d ppm 1.50 (t, J=7.02 Hz, 3H) 1.91-1.98 (m, 1H) 2.02-2.09 (m, 1H) 2.23-2.32 (m, 2H) 2.34-2.44 (m, 2H) 3.24 (quin, J=8.54 Hz, 1H) 4.18 (q, J=7.02 Hz, 2H) 6.95 (d, J=8.54 Hz, 1H) 7.38 (d, J=8.85 Hz, 1H) 7.49 (dd, J=8.85, 2.44 Hz, 1H) 7.72-7.82 (m, 2H) 7.91 (d, J=2.44 Hz, 1H) 8.19 (s, 1H) 8.89 (d, J=2.14 Hz, 1H); $^{13}$C NMR (126 MHz, CDCl$_3$) d ppm 14.84 (s, 1C) 18.22 (s, 1C) 25.55 (s, 1C) 41.31 (s, 1C) 64.76 (s, 1C) 111.09 (s, 1C) 116.96 (s, 1C) 119.57 (s, 1C) 122.01 (s, 1C) 125.14 (s, 1C) 126.59 (s, 1C) 127.33 (s, 1C) 127.39 (s, 1C) 130.50 (s, 1C) 132.78 (s, 1C) 137.95 (s, 1C) 150.08 (s, 1C) 165.23 (s, 1C) 173.90 (s, 1C).

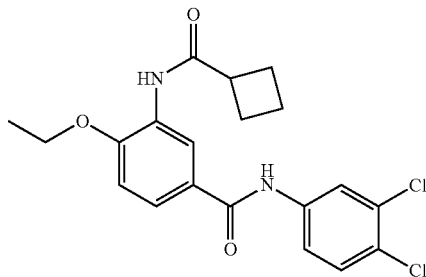 [SMILES: CCOc1ccc(C(=O)Nc2ccc(Cl)c(Cl)c2)cc1NC(=O)C1CCC1]

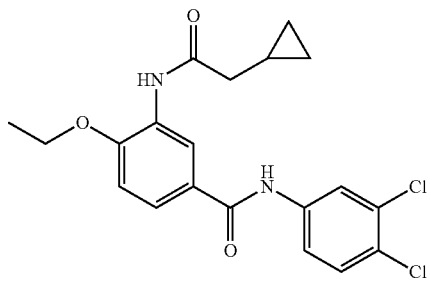 [SMILES: CCOc1ccc(C(=O)Nc2ccc(Cl)c(Cl)c2)cc1NC(=O)CC1CC1]

3-(2-cyclopropylacetamido)-N-(3,4-dichlorophenyl)-4-ethoxybenzamide (74)

Prepared according to the general procedure described in Step d using 3-amino-N-(3,4-dichlorophenyl)-4-ethoxybenzamide 70a (20 mg, 0.062 mmol) and purified by flash column chromatography on silica gel (0-50% EtOAc in Hex) to afford 3-(2-cyclopropylacetamido)-N-(3,4-dichlorophenyl)-4-ethoxybenzamide 74 (8 mg, 0.020 mmol, 31.9% yield) as a white solid. MS (ESI): mass calcd. for C20H20Cl2N2O3, 406.09; m/z found, 407.0 [M+H]+; $^1$H NMR (500 MHz, CDCl$_3$) d ppm 0.32-0.37 (m, 2H) 0.72-0.79 (m, 2H) 1.05-1.14 (m, 1H) 1.52 (t, J=7.02 Hz, 3H) 2.39 (d, J=7.32 Hz, 2H) 4.19 (q, J=6.92 Hz, 2H) 6.97 (d, J=8.54 Hz, 1H) 7.38 (d, J=8.85 Hz, 1H) 7.48 (dd, J=8.70, 2.59 Hz, 1H) 7.77 (dd, J=8.54, 2.14 Hz, 1H) 7.92 (d, J=2.44 Hz, 1H) 8.16 (s, 1H) 8.61 (s, 1H) 8.89 (d, J=2.44 Hz, 1H); $^{13}$C NMR (126 MHz, CDCl$_3$) d ppm 4.94 (s, 1C) 7.31 (s, 1C) 14.93 (s, 1C) 42.89 (s, 1C) 64.74 (s, 1C) 111.01 (s, 1C) 116.85 (s, 1C) 119.59 (s, 1C) 122.05 (s, 1C) 125.18 (s, 1C) 126.62 (s, 1C) 127.37 (s, 1C) 127.46 (s, 1C) 130.52 (s, 1C) 132.80 (s, 1C) 137.92 (s, 1C) 150.20 (s, 1C) 165.23 (s, 1C) 171.20 (s, 1C).

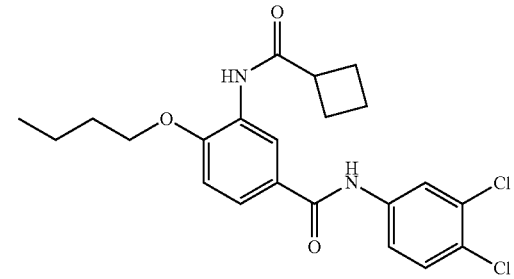 [SMILES: CCCCOc1ccc(C(=O)Nc2ccc(Cl)c(Cl)c2)cc1NC(=O)C1CCC1]

4-butoxy-3-(cyclobutanecarboxamido)-N-(3,4-dichlorophenyl) benzamide (75)

Prepared according to the general procedure described in Step d using 3-amino-4-butoxy-N-(3,4-dichlorophenyl)benzamide 71a (20 mg, 0.057 mmol) and purified by flash column chromatography on silica gel (0-50% EtOAc in Hex) to afford 4-butoxy-3-(cyclobutanecarboxamido)-N-(3,4-dichlorophenyl)benzamide 75 (6 mg, 0.014 mmol, 24.34% yield) as a white solid. MS (ESI): mass calcd. for C22H24Cl2N2O3, 434.12; m/z found, 435.16 [M+H]+; $^1$H NMR (500 MHz, CDCl$_3$) d ppm 1.02 (t, J=7.48 Hz, 3H) 1.53 (dd, J=15.11, 7.48 Hz, 2H) 1.83-1.89 (m, 2H) 1.94-2.00 (m, 1H) 2.06 (dt, J=11.14, 8.77 Hz, 1H) 2.27-2.33 (m, 2H) 2.35-2.44 (m, 2H) 3.20-3.30 (m, 1H) 4.12 (t, J=6.56 Hz, 2H) 6.98 (d, J=8.54 Hz, 1H) 7.41 (s, 1H) 7.49-7.51 (m, 1H) 7.75-7.81 (m, 2H) 7.93 (d, J=2.44 Hz, 1H) 8.07 (s, 1H) 8.89 (d, J=2.14 Hz, 1H); $^{13}$C NMR (126 MHz, CDCl$_3$) d ppm 13.99 (s, 1° C.) 18.20 (s, 1C) 19.42 (s, 1C) 25.56 (s, 1C) 31.18 (s, 1C) 41.30 (s, 1C) 68.89 (s, 1C) 111.20 (s, 1C) 116.74 (s, 1C) 119.58 (s, 1C) 122.05 (s, 1C) 125.11 (s, 1C) 126.54 (s, 1C) 127.60 (s, 1C) 130.58 (s, 1C) 132.88 (s, 1C) 134.80 (s, 1C) 137.86 (s, 1C) 165.17 (s, 1C) 173.87 (s, 1C).

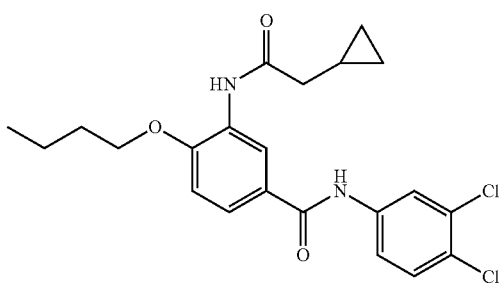 [SMILES: CCCCOc1ccc(C(=O)Nc2ccc(Cl)c(Cl)c2)cc1NC(=O)CC1CC1]

4-butoxy-3-(2-cyclopropylacetamido)-N-(3,4-dichlorophenyl) benzamide (76)

Prepared according to the general procedure described in Step d using 3-amino-4-butoxy-N-(3,4-dichlorophenyl)benzamide 71a (20 mg, 0.057 mmol) and purified by flash column chromatography on silica gel (0-50% EtOAc in Hex) to afford 4-butoxy-3-(2-cyclopropylacetamido)-N-(3,4-dichlorophenyl)benzamide 76 (6 mg, 0.014 mmol, 24.34% yield) as a white solid. MS (ESI): mass calcd. for C22H24Cl2N2O3, 434.12; m/z found, 435.16 [M+H]+; $^1$H NMR (500 MHz, CDCl$_3$) d ppm 0.34 (q, J=4.88 Hz, 2H) 0.71-0.78 (m, 2H) 1.02 (t, J=7.48 Hz, 3H) 1.09 (t, J=7.63 Hz, 1H) 1.49-1.58 (m, 2H) 1.82-1.92 (m, 2H) 2.40 (d, J=7.32 Hz, 2H) 4.13 (t, J=6.56 Hz, 2H) 6.99 (d, J=8.54 Hz, 1H) 7.40 (d, J=8.85 Hz, 1H) 7.49 (dd, J=8.85, 2.44 Hz, 1H) 7.78 (dd, J=8.54, 2.14 Hz, 1H) 7.93 (d, J=2.44 Hz, 1H) 8.07 (s, 1H) 8.59 (s, 1H) 8.90 (d, J=2.14 Hz, 1H); $^{13}$C NMR (126 MHz, CDCl$_3$) d ppm 4.96 (s, 1C) 7.28 (s, 1C) 13.94 (s, 1C) 19.39 (s, 1C) 31.34 (s, 1C) 42.97 (s, 1C) 68.84 (s, 1C) 111.08 (s, 1C) 116.82 (s, 1C) 119.59 (s, 1C) 122.07 (s, 1C) 125.19 (s, 1C) 126.55 (s, 1C) 127.45 (s, 1C) 127.55 (s, 1C) 130.57 (s, 1C) 132.86 (s, 1C) 137.89 (s, 1C) 150.34 (s, 1C) 165.21 (s, 1C) 171.19 (s, 1C).

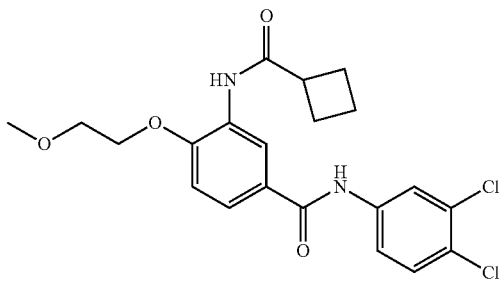 [SMILES: COCCOc1ccc(C(=O)Nc2ccc(Cl)c(Cl)c2)cc1NC(=O)C1CCC1]

3-(cyclobutanecarboxamido)-N-(3,4-dichlorophenyl)-4-(2-methoxyethoxy)benzamide (77)

Prepared according to the general procedure described in Step d using 3-amino-N-(3,4-dichlorophenyl)-4-(2-methoxyethoxy)benzamide 72a (20 mg, 0.056 mmol) and purified by flash column chromatography on silica gel (0-50% EtOAc in Hex) to afford 3-(cyclobutanecarboxamido)-N-(3,4-dichlorophenyl)-4-(2-methoxyethoxy)benzamide 77 (10 mg, 0.023 mmol, 40.6% yield) as a white solid. MS (ESI): mass calcd. for C21H22Cl2N2O4, 436.10; m/z found, 436.96 [M+H]+; $^1$H NMR (500 MHz, CDCl$_3$) d ppm 1.92-1.99 (m, 1H) 1.99-2.10 (m, 1H) 2.23-2.31 (m, 2H) 2.34-2.45 (m, 2H) 3.23 (dd, J=8.85, 8.24 Hz, 1H) 3.46 (s, 3H) 3.75-3.80 (m, 2H) 4.22-4.27 (m, 2H) 7.01 (d, J=8.54 Hz, 1H) 7.39 (d, J=8.54 Hz, 1H) 7.49 (dd, J=8.70, 2.59 Hz, 1H) 7.75 (dd, J=8.54, 2.14 Hz, 1H) 7.93 (d, J=2.44 Hz, 1H) 7.97 (s, 1H) 8.18 (br. s., 1H) 8.90 (d, J=2.44 Hz, 1H); $^{13}$C NMR (126 MHz, CDCl$_3$) d ppm 18.23 (s, 1C) 25.51 (s, 1C) 41.27 (s, 1C) 59.30 (s, 1° C.) 69.20 (s, 1C) 70.78 (s, 1C) 112.99 (s, 1C) 117.22 (s, 1C) 119.59 (s, 1C) 122.05 (s, 1C) 124.99 (s, 1C) 127.44 (s, 1C) 127.64 (s, 1C) 128.48 (s, 1C) 130.54 (s, 1C) 132.83 (s, 1° C.) 137.88 (s, 1C) 150.02 (s, 1C) 165.18 (s, 1C) 174.01 (s, 1C).

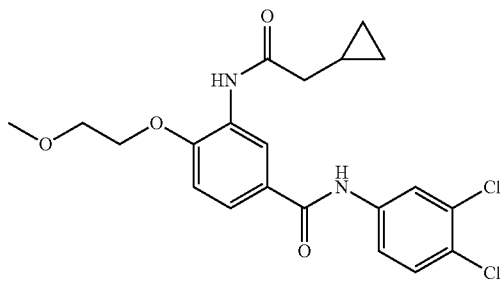 [SMILES: COCCOc1ccc(C(=O)Nc2ccc(Cl)c(Cl)c2)cc1NC(=O)CC1CC1]

3-(2-cyclopropylacetamido)-N-(3,4-dichlorophenyl)-4-(2-methoxyethoxy)benzamide (78)

Prepared according to the general procedure described in Step d using 3-amino-N-(3,4-dichlorophenyl)-4-(2-methoxyethoxy)benzamide 72a (20 mg, 0.056 mmol) and purified by flash column chromatography on silica gel (0-50% EtOAc in Hex) to afford 3-(2-cyclopropylacetamido)-N-(3,4-dichlorophenyl)-4-(2-methoxyethoxy)benzamide 78 (12 mg, 0.027 mmol, 48.7% yield) as a white solid. MS (ESI): mass calcd. for C21H22Cl2N2O4, 436.10; m/z found, 436.90 [M+H]+; $^1$H NMR (500 MHz, CDCl$_3$) d ppm 0.34 (q, J=4.88 Hz, 2H) 0.72-0.79 (m, 2H) 1.05-1.14 (m, 1H) 2.38 (d, J=7.32 Hz, 2H) 3.44 (s, 3H) 3.74-3.83 (m, 2H) 4.22-4.32 (m, 2H) 7.01 (d, J=8.54 Hz, 1H) 7.39 (d, J=8.54 Hz, 1H) 7.48 (dd, J=8.54, 2.44 Hz, 1H) 7.77 (dd, J=8.54, 2.14 Hz, 1H) 7.93 (d, J=2.44 Hz, 1H) 8.12 (s, 1H) 8.68 (s, 1H) 8.90 (d, J=2.14 Hz, 1H); $^{13}$C NMR (126 MHz, CDCl$_3$) d ppm 4.86 (s, 1C) 7.32 (s, 1C) 42.89 (s, 1C) 59.16 (s, 1C) 68.62 (s, 1C) 70.81 (s, 1C) 112.07 (s, 1C) 117.15 (s, 1C) 119.61 (s, 1C) 122.07 (s, 1C) 125.11 (s, 1C) 127.37 (s, 1C) 127.42 (s, 1C) 128.06 (s, 1C) 130.54 (s, 1C) 132.82 (s, 1C) 137.92 (s, 1C) 150.07 (s, 1C) 165.21 (s, 1C) 171.36 (s, 1C).

Example 2

Biological Activity of Synthesized Compounds

Introduction

A3G is among the most strongly selected of human genes (11), likely because it blocks retrotransposition of endogenous retroelements. Chronically infected HIV patients have increased levels of cellular LINE-1 and HERV-K (HML-2) retroelements (12-17). In a rare congenital disorder (Aicardi-Goutieres' Syndrome) and a subset of lupus cases, cytoplasmic sensors recognize excess retroelement nucleic acid to induce a pathologic cellular interferon stimulated gene (ISG) response that causes pathologic systemic inflammation (18). A role for abortive HIV reverse transcripts in "bystander" CD4+ T cell depletion (19) suggests that similar mechanisms may also contribute to HIV pathogenesis.

A3G is upregulated by interferons (20-32). Several separate lines of evidence indicate that A3G activity acutely increases after HIV infection starts inducing an interferon response. However, evidence suggests A3G decreases at some point after HIV is acquired, despite an ongoing interferon response. Two studies have each reported A3G-mediated G-to-A hypermutation in about half the transmitted/founder viruses sequenced from plasma HIV RNA from acutely infected subjects (33, 34). In contrast, three independent reports did not find any evidence of A3G-mediated hypermutation in plasma virus RNA sequenced from 35 chronically infected subjects (4, 35, 36). Taken together, the data suggest A3G activity decreases at some soon after HIV acquisition in most HIV infected subjects.

The concept that A3 activity decreases after HIV infection is also supported by recent work showing HIV Vif adaptation to A3H, closely related to A3G, in acutely infected subjects and in cell culture (37). HIV Vif adaptation to A3G was also found in the Vif proteins of all SIVmac strains, relative to the Vif of SIVsm, and thought to cause cross-species transmission of SIVsm to rhesus macaques in the 1970s (38).

Figure 1:
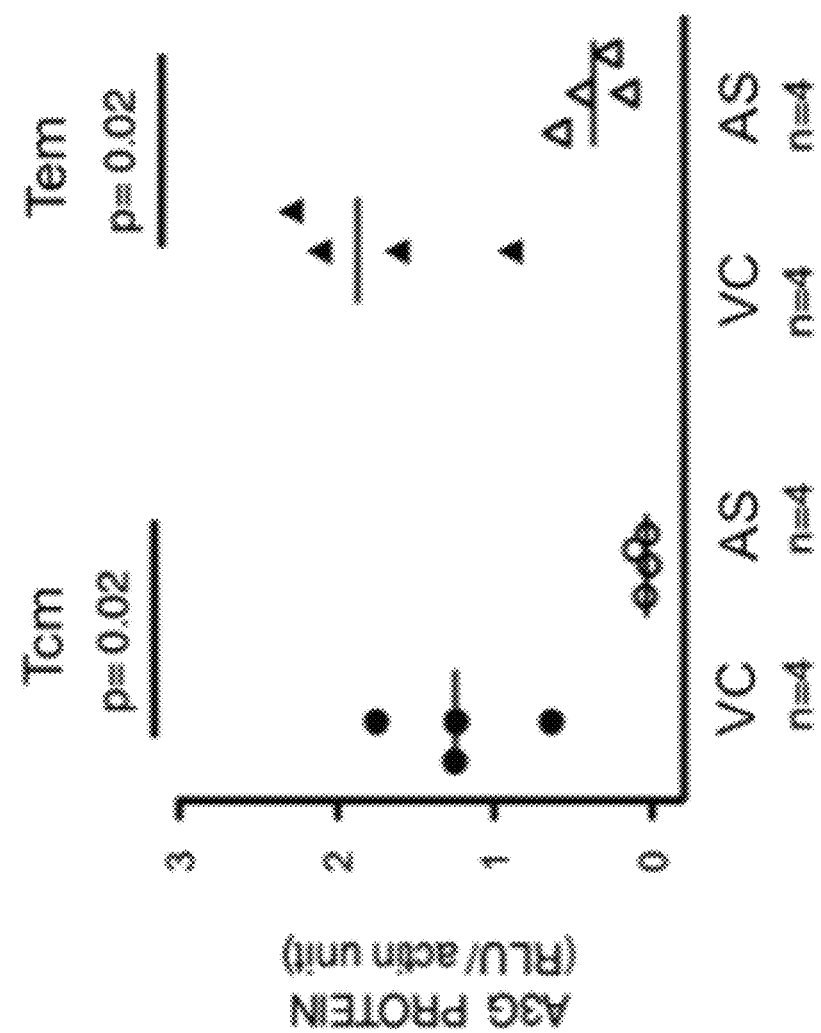
FIG. 1. APOBEC3G protein (quantified from immunoblots stained with anti-APOBEC3G antibody using Licor Odyssey as relative light units, RLU, per actin unit) blood resting memory CD4+ T central memory (Tcm) and T effector memory (Tem) cells from chronically-infected HLA B-27/57-positive controllers (viremic controllers, VC) and non-controllers (antiretroviral suppressed, AS) (5).

There are increasing data indicating that higher levels of APOBEC3s in the physiological range contribute the unusual phenotype of control of Vif-positive HIV in vivo in the absence of antiretroviral treatment seen in many infected persons with certain HLA types (including HLA B57 and B27). Plasma HIV-1 RNA levels in vivo were inversely associated with the A3 signature hypermutation index above a certain level in proviruses in peripheral blood mononuclear cells (PBMC) from HLA B57/27 controllers (4), indicating that A3G activity above a threshold level was needed to decrease Vif-positive virus replication in vivo. This work compared untreated non-controllers to untreated HLA B57/27 controllers with the latter having much lower levels of viremia. In a subsequent paper, untreated HLA B57/27 controllers were compared to ART-suppressed non-controllers (5). The associations of both increased A3G and decreased provirus level with control were again seen; thus, it is not simply a by-product of better viremia suppression as both groups in (5) had suppressed viremia. HLA-linked HIV control was associated with less provirus and more A3G protein in resting CD4+ T central memory (Tcm) and effector memory (Tem) lymphocytes (FIG. 1, from 5). Resting memory T cells with the highest A3G protein levels (>0.5 RLU per unit of actin) had the lowest levels of HIV provirus in vivo (p=0.03, Fisher's exact test) (22). Vif-positive viruses with more virion A3G were found to have decreased virion infectivity ex vivo (5). Thus, increased cellular A3G that can be packaged into Vif-positive virions appears to add a "second line of defense" to previously described immune mechanisms for HLA-restricted HIV control. While controllers' HLA-restricted CD8+ cytotoxic T lymphocyte (CTL) recognition of essential, conserved epitopes in HIV's gag protein provides early control of viremia, HIV often escapes this within months by selection of mutations in targeted epitopes. This, and the fact that some controllers lack these HLA alleles, indicates that additional mechanisms contribute to durable control. It is hypothesized that higher A3G protein levels in controllers' cells are a "back-up" defense mechanism not able to be evaded by antigenic epitope escape that contributes to durable control (5). Further, it is hypothesized that cellular A3G does not decrease after infection in controllers, as some evidence suggests happens in non-controllers.

EXPERIMENTS AND RESULTS

Figure 2B:
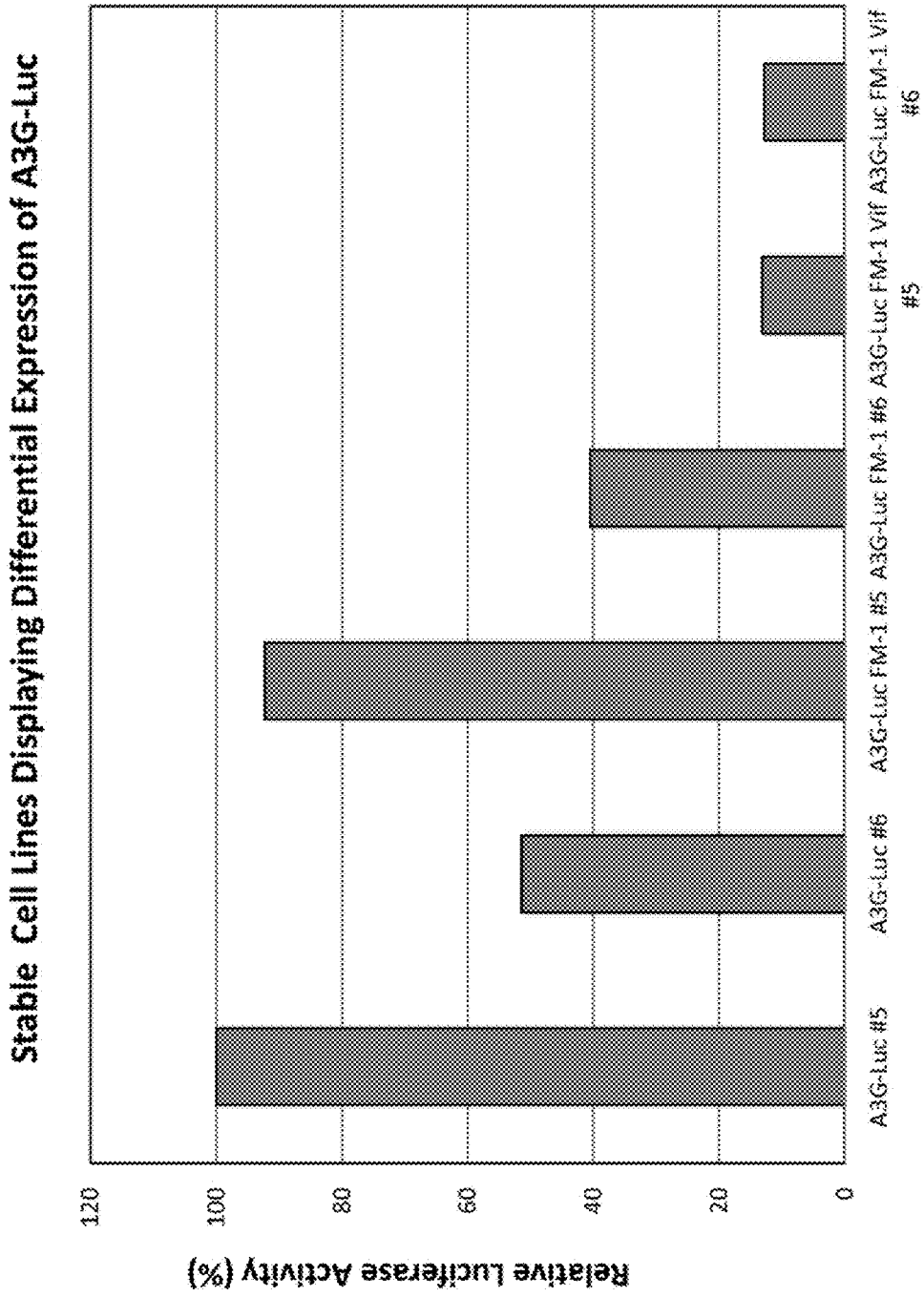

This background led to construction of cell lines to use in a search for compounds that might boost levels of A3s in the HIV target cells of the majority of HIV-infected persons who are non-controllers. The goal is to test a strategy of using such a booster in acute/early infection to prevent the hypothesized decrease of A3G and related A3s in an effort to increase "control" in persons lacking HLA B57/27-associated control. Adherent monolayer HEK293T (hereafter called 293T) cells that do not express any endogenous A3G (or other A3) were chosen to assess increases in exogenous A3G from either antagonism of its Vif-mediated degradation or Vif-independent boosting of cellular expression/stability. 293T and TZM-bl cells were maintained in DMEM (containing 4.5 g/liter glucose, L-glutamine, and sodium pyruvate) medium plus 10% fetal bovine serum, 50 IU/ml penicillin, and 50 µg/ml streptomycin at 37° C. and 5% $CO_2$ throughout the experiments. An A3G-luciferase (A3G-Luc) fusion was cloned into either pCDNA behind a CMV promoter or into a simple retroviral vector, pMSCV-I/Puro. 293T cells were co-transfected with pMSCV-I/Puro-A3G-Luc and pCL-Ampho as well as pCMV-VSV-G plasmids to generate infectious viral particles. After collecting viral supernatant, 293T cells were infected with viral particles harboring the A3G-Luc expressing vector and selected with puromycin (0.75 µg/ml) for three days. Ten single cell clones of stable cells were isolated and tested for expression of A3G-Luc protein by both immunoblotting using antibody against A3G and measuring luciferase activity. Expressions in cell lines used for subsequent experiments are depicted in FIG. 2, upper panel. The A3G-Luc fusion protein was sensitive to Vif-mediated degradation (FIG. 3). Similar cells lines stably expressing A3F were constructed with the same methods (not shown).

To generate a stable cell line expressing both A3G-Luc and Vif proteins, stable cell lines expressing A3G-Luc were infected with viral particle generated by co-transfecting 293T cells with Vif expression lentiviral vector, FM-1-Vif, and delta 8.9 as well as pCMV-VSV-G. Since the FM-1-Vif vector also encodes a GFP reporter gene, the infected cells were sorted for GFP positive cells using FACS analysis. After sorting, expression of both A3G-Luc and Vif was confirmed by immunoblotting using antibody against both A3G and Vif. Expressions in cell lines used for subsequent experiments are shown in FIG. 2, lower panel.

The A3G-Luc fusion protein has anti-HIV activity (FIG. 4). This allowed testing of compounds that increased cellular levels of A3G-Luc for anti-HIV activity.

Others described the bis-amide compound IMB-26 (FIG. 5) to directly bind to A3G and prevent its degradation by Vif. (39). IMB-26 was synthesized and found to be toxic to 293T cells. Interestingly, this series of compounds has been developed for anti-cancer applications due to the cytotoxicity of its analogs (40-43). It was found that the type of halogen determined the in vitro cytotoxicity with iodo being the most toxic and fluoro being approximately 1000-fold less toxic, with the bromo analog being intermediate. The large variation between fluoro and iodo suggests that this compound is acting as an alkylating agent, making it inappropriate as an anti-HIV therapeutic. Because of the toxic nature of IMB-26, we synthesized analogs and screened them for reduced cytotoxicity and retained A3G boosting activity.

To screen compounds that can boost A3G levels, 293T cells (25,000 cells per well in 96-well plate) stably expressing A3G-Luc protein or A3G-Luc/Vif proteins were plated. After 24 hrs post plating culture medium was replaced with 100 µl of new medium containing either DMSO as a control or various compounds (10 µM concentration). After 48 hrs of incubation with compounds culture medium was removed from each well and replaced with 100 µl of Britelite Plus luciferase assay substrate (PerkinElmer). Following 5 min. of incubation at room temperature, 75 μl of each cell lysate was transferred to a 96-well OptiPlate 96 (PerkinElmer) and luminescence was measured in a VICTOR X2 Multilabel Reader (PerkinElmer). Relative activity of compounds for their boosting capability A3G-Luc activity was calculated by plotting DMSO-treated A3G-Luc or A3G-Luc/Vif cells as 100%. Cellular cytotoxicity was measured by counting number of cells after 48 hrs of incubation with compounds compared to DMSO treated cells.

To test the effect of compounds shown to boost A3G-Luc levels in our screening systems on inhibition of wild-type HIV-1 replication by A3G or A3F, 293T cell lines stably expressing A3G or A3F were plated (750,000 cells per well in 6-well plate). At 24 hrs post plating, 1.5 μg of a wild-type (Vif-positive) HIV-1 proviral vector, NL4.3, was transfected into the 293T stable cell lines expressing either A3G or A3F. At 4 hrs post transfection, either DMSO as a control or an individual compound from series described below was added into the culture medium at a 10 μM concentration. At 1 day post transfection, supernatant fluids containing viral particles were filtered through 0.45 μM filter to remove cellular debris. To test the effect of compound on HIV-1 replication, TZM-bl indicator cells were plated at a density of 10,000 cells/well in a 96 well culture plate 24 hrs prior to infection. TZM-bl indicator cells express luciferase gene under the control of HIV LTR promoter and are routinely used to measure HIV-1 replication capability. On the day of infection, the culture medium was removed and the cells inoculated with equal amount of HIV-1 particles in triplicate with 100 μl of viral supernatants in culture medium containing 20 μg/ml DEAE-dextran. After 24 hrs of incubation, culture medium was removed from each well and replaced with 100 μl of Britelite Plus luciferase assay substrate. Following 5 min. of incubation at room temperature, 75 μl of each cell lysate was transferred to a 96-well OptiPlate 96 and luminescence was measured in a VICTOR X2 Multilabel Reader as described above. Relative infectivity was calculated by plotting luciferase activity from viral particle from DMSO treated A3G or A3F cell lines as 100%. We only tested effect A3F- or A3G mediated restriction of HIV-1 replication by compounds boosting luciferase activity by more than 160% compared to DMSO control sample.

To test the effect of the compounds described below on cancer cell death, cell lines derived from different types of cancer were studied in vitro. MCF10A, MCF7, T47D, MDA-MB-157 and MDA-MB-231 are breast cancer cell lines. NHPrE, BHPrE, RWPE1, DU145, and PC3 cells are prostate cell lines. HeLa is cervical cancer cell line. HEK293 is human embryonic kidney cell line lacking A3B expression. There are differences among these cancer cell lines in p53 expression (44-46). MCF10A, MCF7, NHPrE, BHPrE and HEK293 cells have wild-type and functional p53. RWPE1 and HeLa cells have wild-type p53 but the p53 protein in these cell line is not functional because of effects of human papilloma virus E6 protein. T47D, MDA-MB-231, and DU145 cell lines have mutant p53, while MDA-MB-157 and PC3 cells have no p53 expression. 25,000 cells per well were plated in 6 well plates. In the case of HEK293 cells. 500,000 cells per well in 6-well plates were used instead. After 24 hrs, culture medium was replaced with new medium containing either DMSO as control or one of the compounds described below (6 μM per well concentration). After 8 days incubation with compounds, cell numbers were counted from each well and plotted with number of cells from DMSO treated sample as 100%. We performed the experiments at least twice. HEK293, MCF7 and T47D cells they were maintained for 16 days with compounds instead of 8 days.

Lead compounds that increase A3G at concentrations lacking effects on cell death or proliferation were discovered. NU-52 increases A3G in 293T cell lines stably expressing A3G-Luc, with or without Vif, about 3-fold (FIG. 6). This is similar in magnitude to the difference in A3G between HLA B57/27 controller and non-controller cells (22) and more than induced by some other compounds reported earlier in the literature (called RN-18) (47, 48). In 293T cells that were transiently transfected with A3 vectors, NU-52 more markedly increased expression of wild type A3G, mutant Y124A A3G and wild type A3F (FIG. 7). NU-52 also decreased infectivity of virions produced after co-transfection of 293T cells with HIV NL4-3 (encoding a functional Vif) and either A3G or A3F (FIG. 8). Experiments using multiple compounds are summarized in Tables 1-3.

TABLE 1

Increase in Cellular A3G Levels by Compounds

| Compound No. | Concentration (μM) | A3G-Luc Activity (% of Relative Light Units compared to DMSO treated control) | Vif-A3G-Luc Activity (% of RLUs compared to DMSO treated control) |
| --- | --- | --- | --- |
| NU-49 | 10 | | |
| NU-50 | 10 | 115 | 145 |
| NU-51 | 10 | 57 | 55 |
| NU-52 | 10 | 178 | 135 |
| NU-53 | 10 | 172 | 142 |
| NU-54 | 30 | 137 | 116 |
| NU-55 | 5 | 56 | 74 |
| NU-56 | 30 | 114 | 93 |
| NU-57 | 30 | 87 | 74 |
| NU-58 | 30 | 123 | 93 |
| NU-59 | 2 | 49 | 75 |
| NU-60 | 30 | 70 | 69 |
| NU-61 | 30 | 77 | 68 |
| NU-302 | 10 | 196 | 167 |
| NU-303 | 10 | 90 | 71 |
| NU-304 | 10 | 124 | 138 |
| NU-305 | 10 | 121 | 109 |
| NU-306 | 10 | 96 | 84 |
| NU-307 | 10 | 102 | 91 |
| NU-308 | 10 | 92 | 113 |
| NU-309 | 10 | 100 | 94 |
| NU-452 | 10 | 140 | 110 |
| NU-453 | 10 | 169 | 95 |
| NU-454 | 10 | 86 | 84 |
| NU-455 | 10 | 188 | 131 |
| NU-456 | 10 | 148 | 113 |
| NU-457 | 10 | 120 | 93 |
| NU-458 | 10 | 189 | 123 |
| NU-459 | 10 | 106 | 69 |
| NU-460 | 10 | 254 | 119 |
| NU-461 | 10 | 124 | 70 |
| NU-462 | 10 | 282 | 170 |
| NU-463 | 10 | 287 | 178 |
| NU-464 | 10 | 288 | 170 |
| NU-465 | 10 | 193 | 106 |
| NU-466 | 10 | 318 | 202 |
| NU-467 | 10 | 194 | 146 |
| NU-468 | 10 | 213 | 147 |
| NU-469 | 10 | 100 | 82 |
| NU-470 | 10 | 100 | 85 |
| NU-471 | 10 | 238 | 175 |
| NU-472 | 10 | 238 | 146 |
| NU-473 | 10 | 110 | 84 |
| NU-474 | 10 | 105 | 71 |
| NU-564 | 10 | 162 | 102 |
| NU-565 | 10 | 66 | 55 |
| NU-566 | 10 | 106 | 80 |
| NU-567 | 10 | 93 | 76 |

TABLE 1-continued

Increase in Cellular A3G Levels by Compounds

| Compound No. | Concentration (μM) | A3G-Luc Activity (% of Relative Light Units compared to DMSO treated control) | Vif-A3G-Luc Activity (% of RLUs compared to DMSO treated control) |
|---|---|---|---|
| NU-568 | 10 | 96 | 87 |
| NU-569 | 10 | 98 | 85 |
| NU-570 | 10 | 96 | 87 |
| NU-571 | 10 | 116 | 104 |
| NU-572 | 10 | 98 | 91 |
| NU-573 | 10 | 117 | 80 |
| NU-611 | 10 | 67 | 75 |
| NU-612 | 10 | 202 | 178 |
| NU-613 | 10 | 186 | 158 |
| NU-614 | 10 | 96 | 99 |
| NU-615 | 10 | 102 | 105 |
| NU-616 | 10 | 171 | 152 |
| NU-617 | 10 | 191 | 182 |
| NU-124 | 10 | 25 | |
| NU-125 | 10 | 25 | |
| NU-126 | 10 | 4.8 | |
| NU-127 | 10 | 68 | |
| NU-128 | 10 | 141 | |

TABLE 2

Cytotoxicity of Compounds

| Compound No. | Cytotoxicity |
|---|---|
| NU-49 | Cell Death at 10 μM |
| NU-51 | Cell Death at 25 μM |
| NU-52 | Cell Death at 30 μM |
| NU-53 | Cell Death at 20 μM |
| NU-55 | Cell Death at 25 μM |
| NU-59 | Cell Death at 5 μM |
| NU-124 | Cell Proliferation Blocked at 10 μM |
| NU-125 | Cell Proliferation Blocked at 10 μM |
| NU-126 | Cell Proliferation Blocked at 10 μM |
| NU-127 | Cell Proliferation Blocked at 10 μM |

TABLE 3

A3G- and A3F-Mediated Restriction by Compounds

| Compound No. | Concentration (μM) | A3G-mediated Restriction by Compounds on Wild-type HIV-1 (% of HIV replication relative to DMSO treated Control) | A3F-mediated Restriction by Compounds on Wild-type HIV-1 (% of HIV replication relative to DMSO treated Control) |
|---|---|---|---|
| NU-52 | 10 | 57 | 57 |
| NU-302 | 10 | 60 | 58 |
| NU-458 | 10 | 54 | 45 |
| NU-460 | 10 | 34 | 34 |
| NU-462 | 10 | 62 | 53 |
| NU-463 | 10 | 64 | 67 |
| NU-464 | 10 | 77 | 77 |
| NU-465 | 10 | 47 | 53 |
| NU-466 | 10 | 72 | 59 |
| NU-467 | 10 | 79 | 64 |
| NU-468 | 10 | 58 | 48 |
| NU-471 | 10 | 66 | 65 |
| NU-472 | 10 | 61 | 49 |
| NU-564 | 10 | 72 | ND |
| NU-612 | 10 | 81 | 96 |
| NU-613 | 10 | 98 | 85 |
| NU-616 | 10 | 95 | ND |
| NU-617 | 10 | 74 | ND |
| NU-128 | 10 | 62 | ND |

Selected lead compounds (NU52, NU302, NU466) were also found to kill some breast cancer cell lines tested (T47D, MDA-MB-157 and MDA-MB-231), some prostate cancer cell lines tested (RWPE1, DU145, and PC3), and the one cervical cancer cell line tested (HeLa). Some of the cell lines tested were not killed (MCF10A, MCF7, NHPrE, BHPrE, HEK293). (See FIGS. 9A and 9b). All the cancer cell lines killed by the compounds had a non-functional, null, or mutant p53 phenotype. Compounds NU 52, NU 302, NU 466, and NU 611 also were observed to inhibit BC-1 cell proliferation. (See FIG. 10).

Summary: Data shows that NUCC-54052 (aka NU 52, FIG. 1) increased levels of A3G in the A3G-luciferase screening assay (FIG. 2), and in cells transiently transfected with A3G (as well as increasing Y124A A3G and APOBEC3F) (FIG. 3). HIV-1 virions made from cells with NU-52-boosted A3s had decreased infectivity (FIG. 4). Small benzamide molecules (see FIG. 5 for core structure) were observed to increase levels of A3G in cells (FIG. 6). NU52 was observed to increase levels of A3G, A3G mutant Y124A, and A3F in cells (FIG. 7). NU52 was observed to decrease infectivity of HIV-1. In addition, several of the compounds disclosed herein (52, 302, 466) killed or inhibited proliferation of cancer cells lacking functional p53 (FIGS. 9A, 9B, and 10).

REFERENCES

1. Simon V, Zennou V, et al. Natural variation in Vif: differential impact on APOBEC3G/3F and a potential role in HIV-1 diversification. PLoS Pathog. 2005; 1(1): e6.
2. Vetter M L, Johnson M E, et al. Differences in APOBEC3G expression in CD4+ T helper lymphocyte subtypes modulate HIV-1 infectivity. PLoS Pathog. 2009; 5(2): e1000292.
3. Vetter, M. L., and D'Aquila, R. T. Cytoplasmic APOBEC3G restricts incoming Vifpositive human immunodeficiency virus type 1 and increases two-long terminal repeat circle formation in activated T-helper-subtype cells. J Virol 2009; 83: 8646-8654.
4. Kourteva, Y., De Pasquale, et al. APOBEC3G expression and hypermutation are inversely associated with human immunodeficiency virus type 1 (HIV-1) burden in vivo. Virology 2012; 430: 1-9.
5. De Pasquale, M., Kourteva, Y., et al. Lower HIV provirus levels are associated with more APOBEC3G protein in blood resting memory CD4+ T lymphocytes of controllers in vivo. PLOS ONE 2013; 8(10): e76002. doi:10.1371/journal.pone.0076002
6. Jin X, Brooks A, Chen H, et al. APOBEC3G/CEM15 (hA3G) mRNA levels associate inversely with human immunodeficiency virus viremia. J Virol. 2005; 79(17): 11513-6.
7. Jin X, Wu H, Smith H. APOBEC3G levels predict rates of progression to AIDS. Retrovirology. 2007; 4: 20.

8. Swanton C, McGranahan N, Starrett G J, Harris R S. APOBEC Enzymes: Mutagenic Fuel for Cancer Evolution and Heterogeneity. Cancer Discov. 2015 July; 5(7): 704-12. doi: 10.1158/2159-8290.CD-15-0344. Epub 2015 Jun. 19

9. Burns M B, Leonard B, Harris R S. APOBEC3B: pathological consequences of an innate immune DNA mutator. Biomed J. 2015 March-April; 38(2):102-10. doi: 10.4103/2319-4170.148904.

10. Fox E J, Loeb L A. Lethal mutagenesis: targeting the mutator phenotype in cancer. Semin Cancer Biol. 2010 October; 20(5):353-9. doi: 10.1016/j.semcancer.2010.10.005.

11. Sawyer S L, Emerman M, Malik H S. Ancient adaptive evolution of the primate antiviral DNA-editing enzyme APOBEC3G. PLoS Biol. 2004; 2(9): E275.

12. Gonzalez-Hernandez M J, Swanson M D, et al. Expression of human endogenous retrovirus type K (HML-2) is activated by the Tat protein of HIV-1. J Virol. 2012; 86(15): 7790-805.

13. Contreras-Galindo, R., Kaplan, M. H., et al. Characterization of human endogenous retroviral elements in the blood of HIV-1-infected individuals. J Virol 2012; 86: 262-276.

14. Ormsby, C. E., Sengupta, D., et al. Human endogenous retrovirus expression is inversely associated with chronic immune activation in HIV-1 infection. PLoS One 2012; 7: e41021.

15. Jones, R. B., Garrison, K. E., et al. HERV-K-specific T cells eliminate diverse HIV-1/2 and SIV primary isolates. J Clin Invest 2012; 122: 4473-4489.

16. Jones, R. B., Song, H., et al. LINE-1 Retrotransposable Element DNA Accumulates in HIV-1-infected Cells. J Virol 2013; 87(24): 13307-20.

17. Coffin J, personal communication, abstract presented at 2013 Cold Spring Harbor Retrovirus Meeting.

18. Crow Y J, Rehwinkel J. Aicardi-Goutieres syndrome and related phenotypes: linking nucleic acid metabolism with autoimmunity. Hum Mol Genet. 2009; 18(R2): R130-6.

19. Doitsh G, Cavrois M, et al. Abortive HIV infection mediates CD4 T cell depletion and inflammation in human lymphoid tissue. Cell. 2010; 143(5): 789-801.

20. Mussil B, Sauermann U, et al. Increased APOBEC3G and APOBEC3F expression is associated with low viral load and prolonged survival in simian immunodeficiency virus infected rhesus monkeys. Retrovirology. 2011; 8: 77.

21. Mohanram V, Skild A E, et al. IFN-α induces APOBEC3G, F, and A in immature dendritic cells and limits HIV-1 spread to CD4+ T cells. J Immunol. 2013; 190(7): 3346-53.

22. Chen H, Wang L W, et al. Interferon-alpha Induces High Expression of APOBEC3G and STAT-1 in Vitro and in Vivo. Int J Mol Sci. 2010; 11(9): 3501-12.

23. Wang Y J, Wang X, et al. Expression and regulation of antiviral protein APOBEC3G in human neuronal cells. J Neuroimmunol. 2009; 206(1-2): 14-21.

24. Trapp S, Derby N R, et al. Double-stranded RNA analog poly(I:C) inhibits human immunodeficiency virus amplification in dendritic cells via type I interferon-mediated activation of APOBEC3G. J Virol. 2009; 83(2): 884-95.

25. Wang F X, Huang J, et al. APOBEC3G upregulation by alpha interferon restricts human immunodeficiency virus type 1 infection in human peripheral plasmacytoid dendritic cells. J Gen Virol. 2008; 89(Pt 3): 722-30.

26. Argyris E G, Acheampong E, et al. The interferon-induced expression of APOBEC3G in human blood-brain barrier exerts a potent intrinsic immunity to block HIV-1 entry to central nervous system. Virology. 2007; 367(2): 440-51.

27. Ying S, Zhang X, et al. Cell-specific regulation of APOBEC3F by interferons. Acta Biochim Biophys Sin (Shanghai). 2007; 39(4): 297-304.

28. Sarkis P T, Ying S, et al. STAT1-independent cell type-specific regulation of antiviral APOBEC3G by IFN-alpha. J Immunol. 2006; 177(7): 4530-40.

29. Chen K, Huang J, et al. Alpha interferon potently enhances the anti-human immunodeficiency virus type 1 activity of APOBEC3G in resting primary CD4 T cells. J Virol. 2006; 80(15): 7645-57.

30. Bonvin M, Achermann F, et al. Interferon-inducible expression of APOBEC3 editing enzymes in human hepatocytes and inhibition of hepatitis B virus replication. Hepatology. 2006; 43(6): 1364-74.

31. Tanaka Y, Marusawa H, et al. Anti-viral protein APOBEC3G is induced by interferon-alpha stimulation in human hepatocytes. Biochem Biophys Res Commun. 2006; 341(2): 314-9.

32. Peng G, Lei K J, et al. Induction of APOBEC3 family proteins, a defensive maneuver underlying interferon-induced anti-HIV-1 activity. J Exp Med. 2006; 203(1): 41-6.

33. Wood, N., et al., HIV evolution in early infection: selection pressures, patterns of insertion and deletion, and the impact of APOBEC. PLoS Pathog, 2009. 5(5): e1000414.

34. Abrahams, M. R., et al., Rapid, complex adaptation of transmitted HIV-1 full-length genomes in subtype C-infected individuals with differing disease progression. AIDS, 2013; 27(4): 507-18.

35. Kieffer T L, Kwon P, et al. G→A hypermutation in protease and reverse transcriptase regions of human immunodeficiency virus type 1 residing in resting CD4+ T cells in vivo. J Virol. 2005; 79(3): 1975-80.

36. Land, A. M., Ball, T. B., et al. Human immunodeficiency virus (HIV) type 1 proviral hypermutation correlates with CD4 count in HIV-infected women from Kenya. J Virol 2008; 82: 8172-8182.

37. Ooms M, Brayton B, et al. HIV-1 Vif adaptation to human APOBEC3H haplotypes. Cell Host Microbe. 2013; 14(4): 411-21.

38. Krupp A, McCarthy K R, et al. APOBEC3G polymorphism as a selective barrier to cross-species transmission and emergence of pathogenic SIV and AIDS in a primate host. PLoS Pathog. 2013; 9(10): e1003641.

39. Cen, S.; Peng, Z. G.; Li, X. Y.; Li, Z. R.; Ma, J.; Wang, Y. M.; Fan, B.; You, X. F.; Wang, Y. P.; Liu, F.; Shao, R. G.; Zhao, L. X.; Yu, L. Y.; Jiang, J. D., Small Molecular Compounds Inhibit HIV-1 Replication through Specifically Stabilizing APOBEC3G. *Journal of Biological Chemistry* 2010, 285 (22), 16546-16552.

40. Jiang, J. D.; Roboz, J.; Weisz, I.; Deng, L.; Ma, L. H.; Holland, J. F.; Bekesi, J. G., Synthesis, cancericidal and antimicrotubule activities of 3-(haloacetamido)-benzoylureas. *Anti-Cancer Drug Des* 1998, 13 (7), 735-747.

41. Jiang, J. D.; Davis, A. S.; Middleton, K; Ling, Y. H.; Perez-Soler, R.; Holland, J. F.; Bekesi, J. G., 3-(iodoacetamido)-benzoylurea: A novel cancericidal tubulin ligand that inhibits microtubule polymerization, phosphorylates bcl-2, and induces apoptosis in tumor cells. *Cancer Research* 1998, 58 (23), 5389-5395.

42. Li, J. N.; Song, D. Q.; Lin, Y. H.; Hu, Q. Y.; Yin, L.; Bekesi, G.; Holland, J. F.; Jiang, J. D., Inhibition of microtubule polymerization by 3-bromopropionylamino benzoylurea (JIMB01), a new cancericidal tubulin ligand. *Biochemical pharmacology* 2003, 65 (10), 1691-1699.
43. Hu, L.; Li, Z. R.; Li, J. N.; Qu, J.; Jiang, J. D.; Boykin, D. W., 3-(2'-Bromopropionylamino)-benzamides as novel S-phase arrest agents. *Bioorganic & medicinal chemistry letters* 2007, 17 (24), 6847-52.
44. http://p53.free.fr/Database/Cancer_cell_lines/53_cell_lines.html (Accessed Aug. 12, 2015)
45. Bello D, Webber M M, Kleinman H K, Wartinger D D, Rhim J S. Androgen responsive adult human prostatic epithelial cell lines immortalized by human papillomavirus 18. Carcinogenesis. 1997 June; 18(6):1215-23.
46. Jiang M, Strand D W, Fernandez S, He Y, Yi Y, Birbach A, Qiu Q, Schmid J, Tang D G, Hayward S W. Functional remodeling of benign human prostatic tissues in vivo by spontaneously immortalized progenitor and intermediate cells. Stem Cells. 2010 February; 28(2):344-56. doi: 10.1002/stem.284.
47. Nathans R, Cao H, et al. Small-molecule inhibition of HIV-1 Vif. Nat Biotechnol. 2008 October; 26(10): 1187-92.
48. Ali A, Wang J, et al. Synthesis and structure-activity relationship studies of HIV-1 virion infectivity factor (Vif) inhibitors that block viral replication. ChemMedChem. 2012; 7(7): 1217-29.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula:

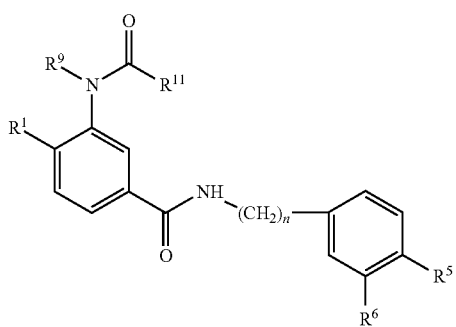

wherein:

n is 0 or 1;

$R^1$ is hydroxyl, C1-C6-alkoxy, or

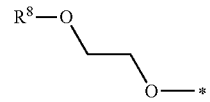

wherein $R^8$ is C1-C6-alkyl,

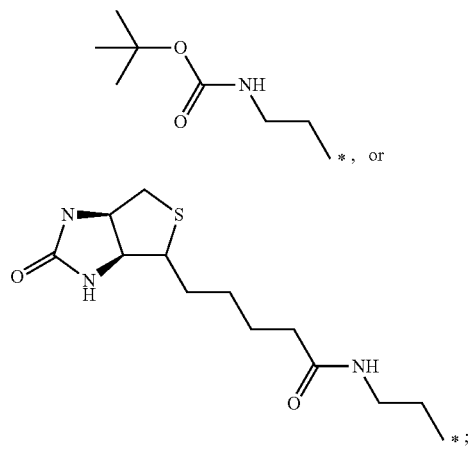

$R^9$ is H, or C1-C6-alkyl;

$R^{11}$ is H, C3-C6-alkyl optionally substituted with C1-C6-alkoxy, hydroxyl, C1-C6-alkylamino, C1-C6-dialkyl amino, phenyl, benzyl, benzo[1,3] diox-8-yl, pyridin-2-yl, pyridin-3-yl, pyridin-4-yl, C3-C6-cycloalkyl optionally substituted with methyl, C1-C6-alkoxy, N-piperidinyl, tetrahydrofuran-2-yl, adamantan-7-yl, or

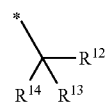

wherein $R^{12}$ and $R^{13}$ are independently selected from 4 C1-C6-alkyl optionally substituted with C1-C6-alkoxy, C1-C6-alkoxy, C1-C6 cycloalkyl, phenyl, C1-C6-alkylamino, C1-C6-dialkyl amino, or $R^{12}$ and $R^{13}$ together form a C3-C6 homocycle or a C3-C6 heterocycle, which optionally is unsaturated at one or more bonds;

$R^{14}$ is H or C1-C6-alkyl;

$R^5$ is halo; and $R^6$ is halo.

2. The compound of claim 1, wherein n is 0.

3. The compound of claim 1, wherein $R^1$ is methoxy.

4. The compound of claim 1, having a formula:

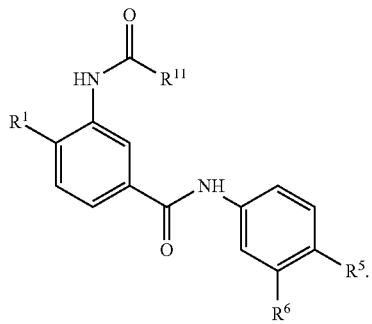

5. The compound of claim 4, wherein $R^1$ is C1-C6-alkoxy.

6. The compound of claim 4, wherein $R^{11}$ is H, C3-C6-alkyl optionally substituted with C1-C6-alkoxy, hydroxyl, C1-C6-alkylamino, C1-C6 dialkylamino, phenyl, benzyl, benzo[1,3]diox-8-yl, pyridin-2-yl, pyridin-3-yl, pyridin-4-yl, C3-C6-cycloalkyl optionally substituted with methyl, C1-C6-alkoxy, N-piperidinyl, and tetrahydrofuran-2-yl.

7. The compound of claim 1, wherein one or both of $R^5$ and $R^6$ are chloro.

8. The compound of claim 1 having a formula:

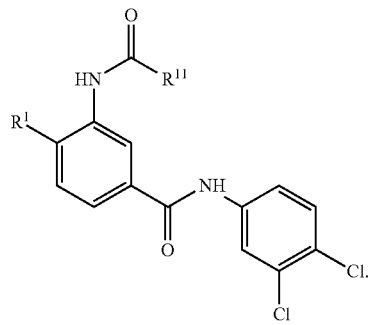

9. A compound having a formula selected from:

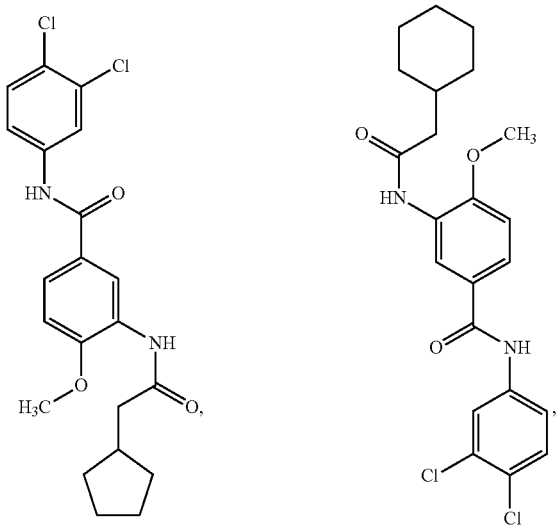

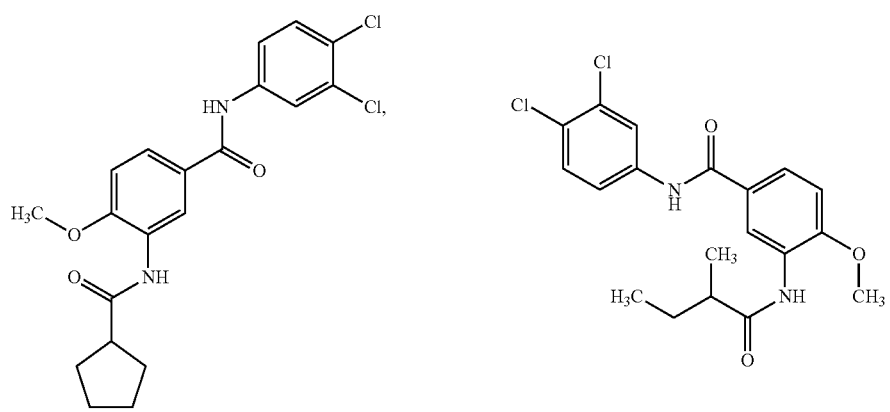

111
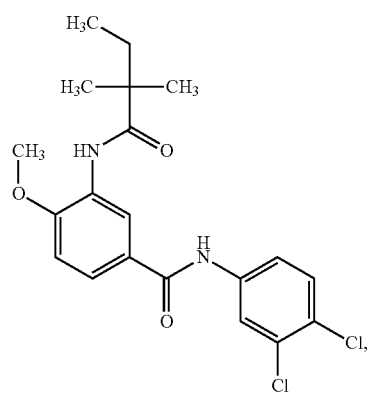
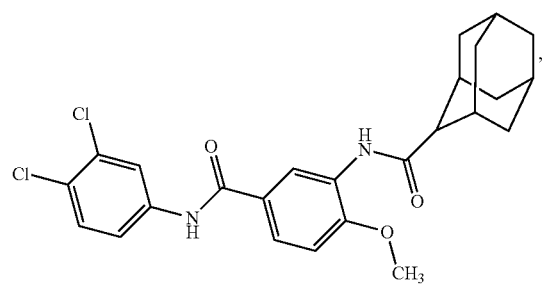
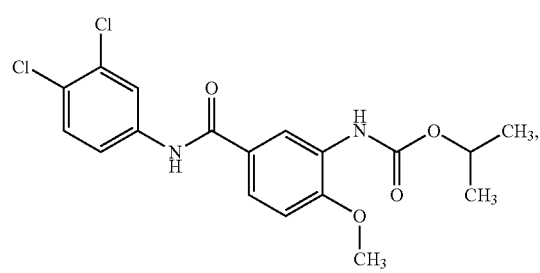
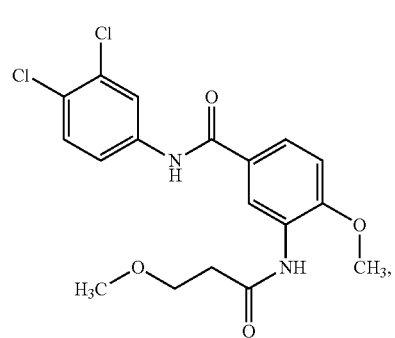
112
-continued
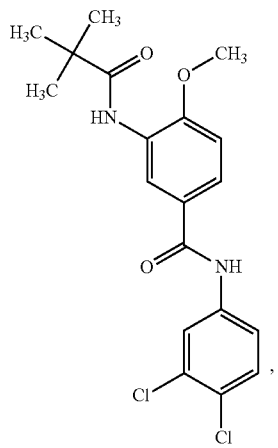
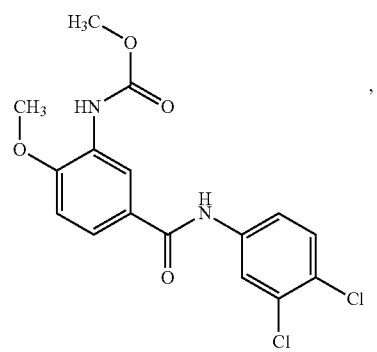
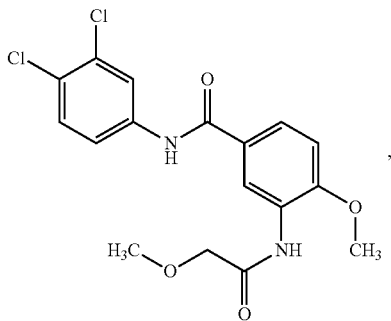
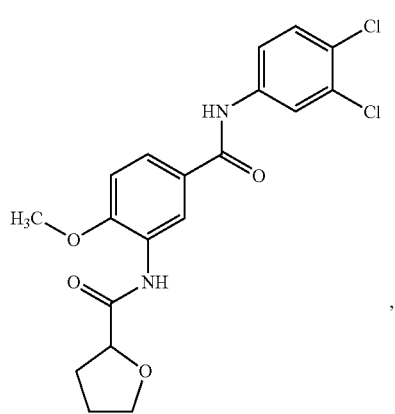

113
-continued
114
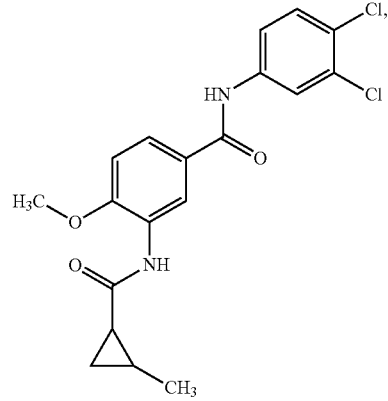
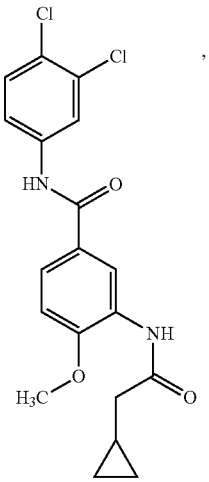
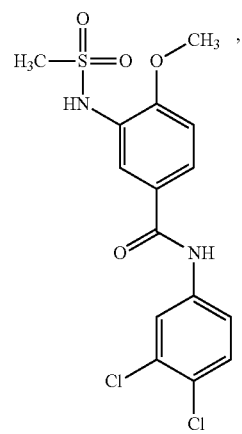
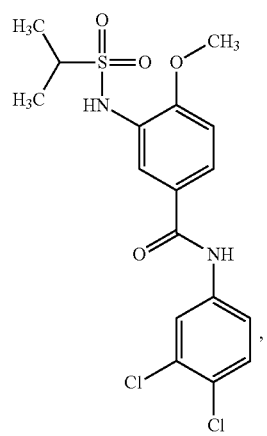
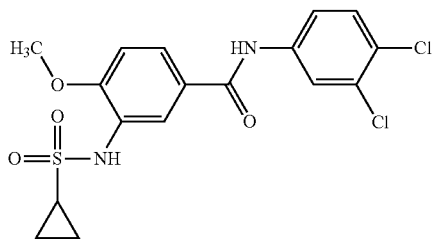
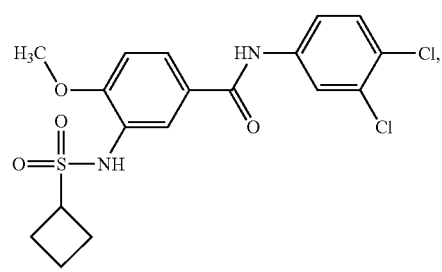
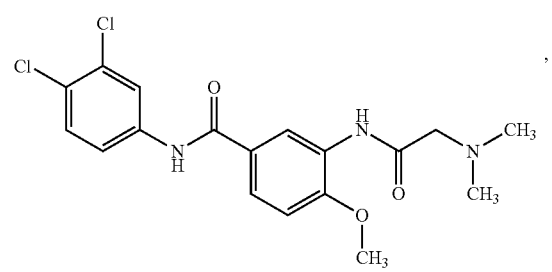
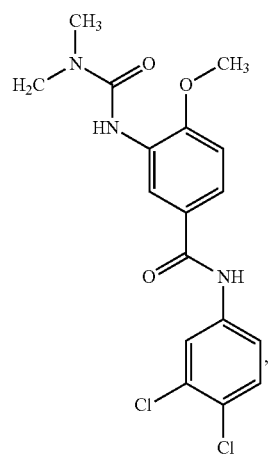
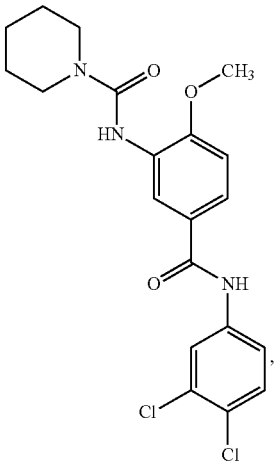
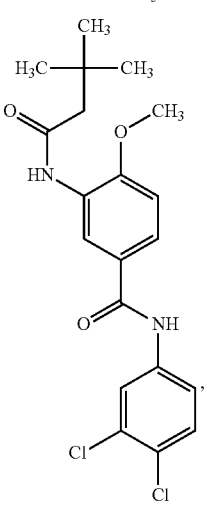

115
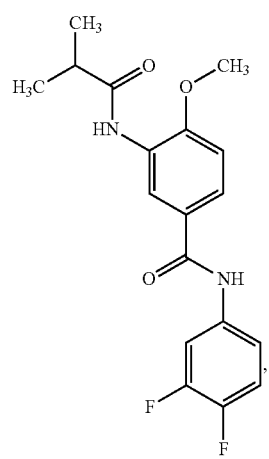
-continued
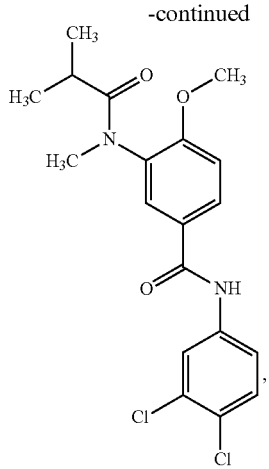
116
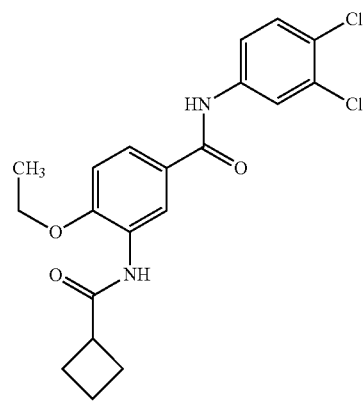
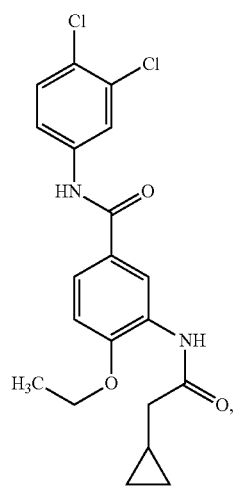
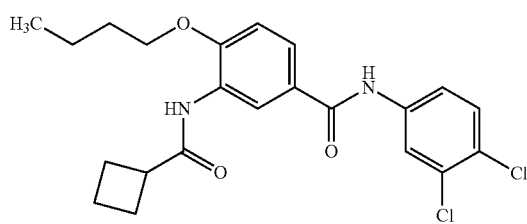
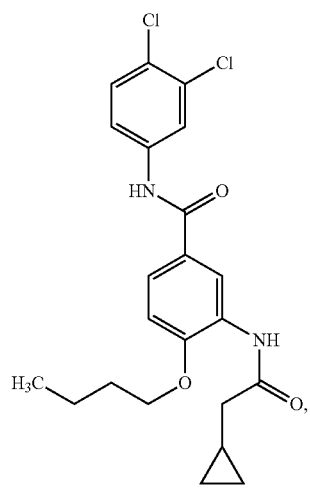
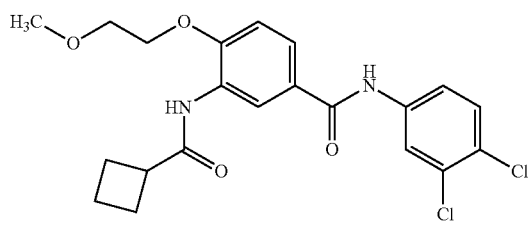

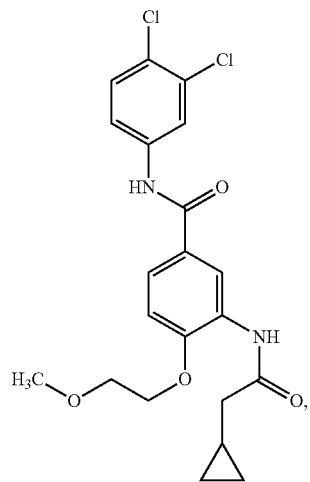
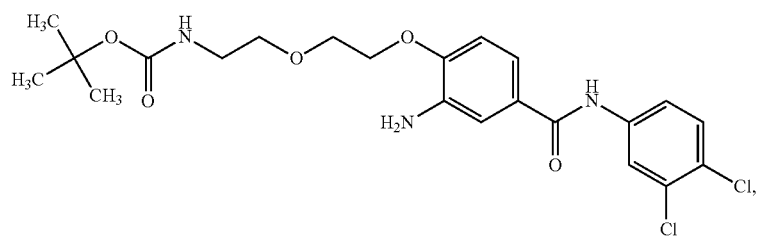
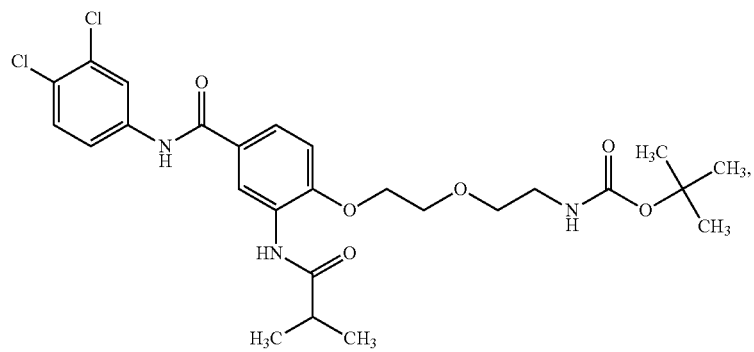
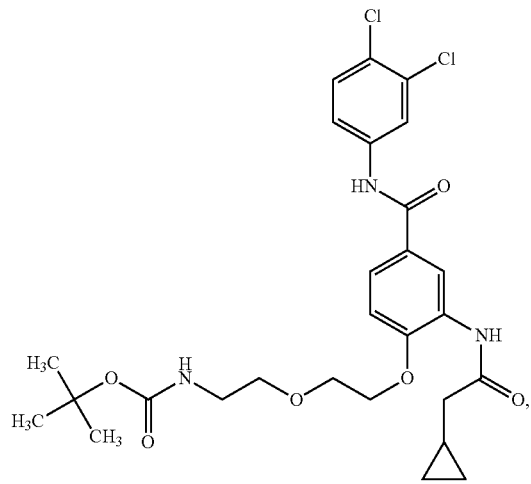

-continued
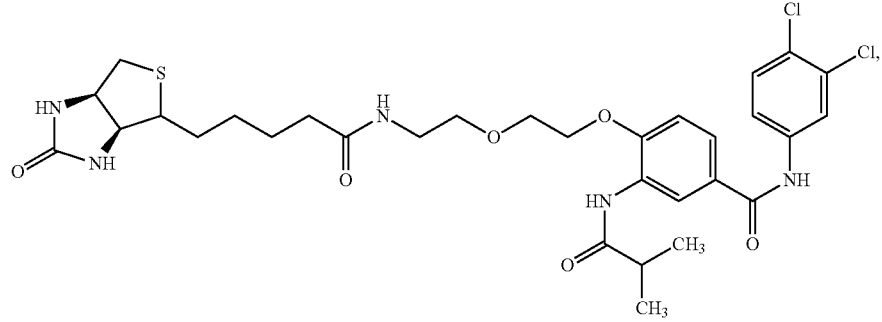
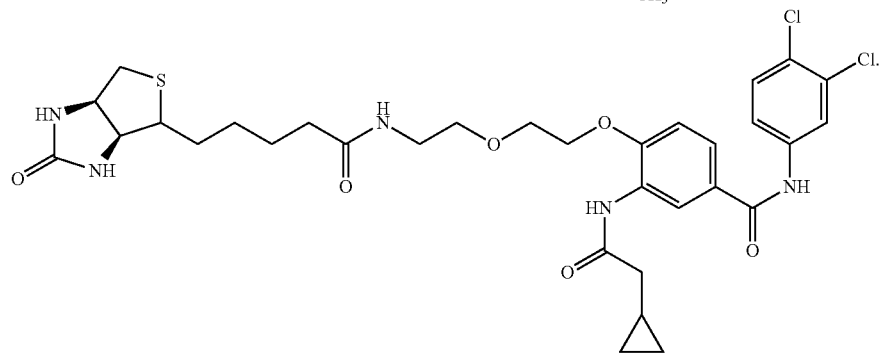
10. The compound of claim 9 having a formula:
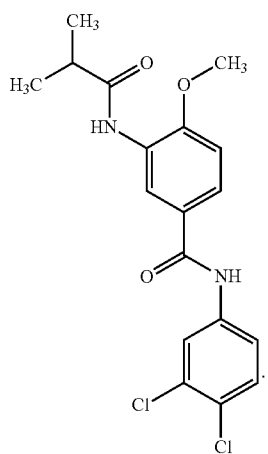 [SMILES: COc1ccc(C(=O)Nc2ccc(Cl)c(Cl)c2)cc1NC(=O)C(C)C]
11. The compound of claim 9 having a formula:
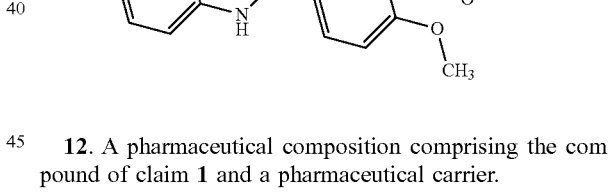
12. A pharmaceutical composition comprising the compound of claim 1 and a pharmaceutical carrier.
13. A pharmaceutical composition comprising the compound of claim 9 and a pharmaceutical carrier.
* * * * *